(12) United States Patent
McDaniel et al.

(10) Patent No.: US 9,393,160 B2
(45) Date of Patent: Jul. 19, 2016

(54) TAMPON WITH CONTACT ELEMENTS

(75) Inventors: Mary Lou McDaniel, Appleton, WI (US); John David Amundson, Greenville, WI (US); Steven Craig Gehling, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 282 days.

(21) Appl. No.: 13/537,138

(22) Filed: Jun. 29, 2012

(65) Prior Publication Data

US 2014/0005627 A1 Jan. 2, 2014

(51) Int. Cl.
*A61F 13/20* (2006.01)
*A61F 13/22* (2006.01)

(52) U.S. Cl.
CPC ........... *A61F 13/2068* (2013.01); *A61F 13/206* (2013.01)

(58) Field of Classification Search
CPC . A61F 13/202; A61F 13/206; A61F 13/2068; A61F 13/2028; A61F 13/2065; A61F 13/2034; A61F 13/2031; A61F 13/2037; A61F 13/208
USPC ............................................. 604/385.17, 904
See application file for complete search history.

(56) References Cited

U.S. PATENT DOCUMENTS

| | | | | |
|---|---|---|---|---|
| 2,073,410 | A | * | 3/1937 | Thomas ........................ 604/374 |
| 2,905,175 | A | | 9/1959 | Schwartz |
| 3,085,574 | A | * | 4/1963 | Penksa ............................ 604/15 |
| 3,610,243 | A | * | 10/1971 | Jones, Sr. ...................... 604/375 |
| 3,624,746 | A | | 11/1971 | Grad et al. |
| 3,794,029 | A | | 2/1974 | Dulle |
| 4,185,631 | A | | 1/1980 | McConnell |
| 4,212,301 | A | | 7/1980 | Johnson |
| 4,288,884 | A | * | 9/1981 | Bahls ........................... 15/244.1 |
| 4,335,720 | A | | 6/1982 | Glassman |
| 4,816,100 | A | | 3/1989 | Friese |
| 5,004,467 | A | | 4/1991 | Hinzmann et al. |
| 5,047,024 | A | | 9/1991 | Glassman et al. |
| 5,112,348 | A | | 5/1992 | Glassman |
| 5,514,158 | A | * | 5/1996 | Kanesaka ...................... 606/213 |
| 5,584,827 | A | * | 12/1996 | Korteweg et al. ............. 604/369 |
| 6,039,716 | A | | 3/2000 | Jessup et al. |
| 6,177,608 | B1 | | 1/2001 | Weinstrauch |
| 6,186,994 | B1 | | 2/2001 | Bowles et al. |

(Continued)

FOREIGN PATENT DOCUMENTS

EP 0 685 213 A2 12/1995
WO WO 95/16423 A2 6/1995

(Continued)

OTHER PUBLICATIONS

Co-Pending U.S. Appl. No. 13/333,150, filed Dec. 21, 2011, by Mary Lou McDaniel for "Tampon."

(Continued)

*Primary Examiner* — Lynne Anderson
*Assistant Examiner* — Kathryn E Ditmer
(74) *Attorney, Agent, or Firm* — Kimberly-Clark Worldwide, Inc.

(57) ABSTRACT

A pledget for a tampon having improved leakage prevention of bodily fluid after the tampon is inserted in the vagina. The pledget can have an absorbent structure having two layers. At least one of the layers of the absorbent structure can have one contact element at least partially separated from a second contact element.

18 Claims, 30 Drawing Sheets

(56) References Cited

U.S. PATENT DOCUMENTS

| | | |
|---|---|---|
| 6,419,777 B1 | 7/2002 | Achter et al. |
| 6,458,072 B1 | 10/2002 | Zunker |
| 6,511,451 B1 | 1/2003 | Schoelling et al. |
| 6,558,370 B2 | 5/2003 | Moser |
| 6,719,743 B1 | 4/2004 | Wada |
| 6,743,212 B1 | 6/2004 | Cole et al. |
| 6,773,423 B2 | 8/2004 | Osborn, III et al. |
| 6,840,927 B2 | 1/2005 | Hasse et al. |
| 7,192,421 B2 | 3/2007 | Hasse et al. |
| 7,338,462 B2 | 3/2008 | Minoguchi et al. |
| 7,845,055 B1 | 12/2010 | Kimball et al. |
| 7,845,380 B2 | 12/2010 | Binner et al. |
| 2003/0097106 A1 | 5/2003 | Hasse et al. |
| 2003/0229328 A1 | 12/2003 | Costa |
| 2004/0030316 A1 | 2/2004 | Gubernick et al. |
| 2005/0027275 A1* | 2/2005 | Wasson et al. ........... 604/385.01 |
| 2005/0256482 A1 | 11/2005 | Minoguchi et al. |
| 2005/0256484 A1 | 11/2005 | Chase et al. |
| 2005/0277866 A1 | 12/2005 | Minoguchi et al. |
| 2006/0247592 A1 | 11/2006 | Schmidt-Forst et al. |
| 2007/0073257 A1 | 3/2007 | Buck et al. |
| 2007/0260211 A1 | 11/2007 | Schmidt-Forst et al. |
| 2008/0154174 A1 | 6/2008 | Costa |
| 2008/0154222 A1 | 6/2008 | Chaffringeon |
| 2008/0221502 A1 | 9/2008 | Binner et al. |
| 2008/0262463 A1 | 10/2008 | Noet et al. |
| 2009/0036859 A1 | 2/2009 | Dougherty, Jr. et al. |
| 2009/0281474 A1 | 11/2009 | Dougherty, Jr. et al. |
| 2011/0077612 A1 | 3/2011 | Jorgensen et al. |
| 2012/0053544 A1 | 3/2012 | Drevik |

FOREIGN PATENT DOCUMENTS

| | | | |
|---|---|---|---|
| WO | WO 98/46182 A1 | | 10/1998 |
| WO | WO 2006/016933 A1 | | 2/2006 |
| WO | WO 2010117309 A1 | * | 10/2010 |
| WO | WO 2013/093675 A1 | | 6/2013 |

OTHER PUBLICATIONS

Co-pending U.S. Appl. No. 13/333,311, filed Dec. 21, 2011, by Mary Lou McDaniel for "Tampon Method of Manufacture."

Co-pending U.S. Appl. No. 13/537,153, filed Jun. 29, 2012, by Mary Lou McDaniel for "Tampon Method of Manufacture."

* cited by examiner

TAMPON WITH CONTACT ELEMENTS

BACKGROUND

Currently, there are two basic types of tampons used for feminine hygiene. The first type is a digitally insertable tampon which is designed to be inserted directly by the user's fingers. The second type is an applicator style tampon which is designed to be inserted with the aid of an applicator. Both types are usually made by folding or rolling rectangular strips of absorbent material into a blank and then compressing the blank into a cylindrically-shaped pledget. The pledget may or may not have a cover. In both types, a withdrawal string can be attached to the pledget. The combination of a pledget and a withdrawal string is considered a useable tampon product. The tampon can then be wrapped and packaged for sale. In the applicator style tampon, the tampons can be assembled into an applicator prior to being wrapped and packaged.

Tampons work by acquiring vaginal fluids, including menses, at the interface between the tampon and vaginal wall. To ensure this contact, current tampons alter the vagina immediately upon insertion. This alteration contributes to early premature, "by-pass" leakage. After the tampon absorbs the vaginal fluids, including menses, most tampons begin to expand uniformly and globally, further contributing to this leakage. At the same time, the tampon begins to become more flexible and conformable to allow for a better global/macro fit to the vagina. This predetermined and uniform tampon response that drives this global/macro expansion is governed by the tampon construction and materials.

Even when fluid is acquired locally and the deformational forces on the tampon by the vaginal environment are applied locally, with current tampons the construction or materials of the tampons inhibits or constrains their capacity to expand or adapt to give a local/micro fit. These constructions and materials force the entire tampon to respond to these local fluid acquisition and deformational forces through material connectivity or material stiffness.

When attempts are made to allow for more local adaptation in tampon constructions, the constructions do not acquire the fluids well because of inadequate contact area because they cannot match the local contours of the vaginal wall or are not conformable enough to adapt to the women's individual local contours (e.g. folds and convolutions) found on the vaginal wall. In addition, these attempts create integrity issues with the tampons that lead to portions of the tampon remaining within the vagina after tampon removal. This inadequate contact is especially true during the wiping action of the vagina by the tampon when the tampon is inserted and removed.

Current tampon construction processes construct these inadequate tampons that have this predetermined and uniform tampon response. They create these constraints, inadequate contact area, and integrity issues in order to drive this predetermined and uniform tampon response and, therefore, limit the tampon from effectively responding locally. New construction processes will be needed to construct tampons that overcome the inadequacy of current tampons.

There remains a need for a tampon that responds locally to meet the individual protection needs of women and processes to make such tampons. There remains a need for a tampon that prevents leakage of body fluid after being inserted into a woman's vagina. There remains a need for a tampon that provides efficient utilization of the entire tampon structure during use. There remains a need for a tampon that provides a customized fit to the anatomy of a woman's vaginal cavity. There remains a need for a tampon that can deform and come into contact with the folds and convolutions of the walls of the vaginal cavity and acquire any contacted fluid.

SUMMARY

In an embodiment, a pledget can have an absorbent structure which can have a first layer having a first surface, a second surface, a first contact element, and a second contact element at least partially separated from the first contact element and a second layer having a first surface and a second surface wherein at least one of the first surface and the second surface of the first layer can be in a face to face relationship with at least one of the first surface and the second surface of the second layer. In an embodiment, the first contact element and the second contact element can be at least partially separated by a slit. In an embodiment, the first contact element and the second contact element can be at least partially separated by an amplitude of an arc. In an embodiment, the first layer can have a fold. In an embodiment, the first layer can have a first portion of at least one of the first surface and the second surface in communication with a second portion of at least one of the first surface and the second surface of the first layer. In an embodiment, the first layer can have a first transverse edge and a second transverse edge and the second layer can have a first transverse edge and a second transverse edge. In an embodiment, at least one of the first and second contact elements of the first layer can be associated with at least one of the first transverse edge and the second transverse edge of the first layer. In an embodiment, at least one of the first transverse edge and the second transverse edge of the first layer can substantially align with at least one of the first transverse edge and the second transverse edge of the second layer. In an embodiment, at least one of the first transverse edge and the second transverse edge of the first layer can extend beyond at least one of the first transverse edge and the second transverse edge of the second layer.

In an embodiment, a pledget can have an absorbent structure which can have a first layer radially wound with a second layer and a first contact element incorporated in the first layer at least partially separated from a second contact element incorporated in the first layer. In an embodiment, the first contact element and the second contact element can be at least partially separated by a slit. In an embodiment, the first contact element and the second contact element can be at least partially separated by an amplitude of an arc. In an embodiment, the first layer further can have a fold. In an embodiment, the first layer can have a first transverse edge and a second transverse edge and the second layer can have a first transverse edge and a second transverse edge. In an embodiment, at least one of the first and second contact elements of the first layer can be associated with at least one of the first transverse edge and the second transverse edge of the first layer. In an embodiment, at least one of the first transverse edge and the second transverse edge of the first layer can substantially align with at least one of the first transverse edge and the second transverse edge of the second layer. In an embodiment, at least one of the first transverse edge and the second transverse edge of the first layer can extend beyond at least one of the first transverse edge and the second transverse edge of the second layer.

DETAILED DESCRIPTION

The tampon of the current disclosure can be inserted above the introital region of a woman's vagina, can intercept the fluid flow of menses, blood, and other body fluids, and can prevent the fluid from exiting the vagina. While the pledgets and tampons of the current disclosure are described for use as a menstrual device, it will be readily apparent that the pledgets and tampons can also be used as any other suitable vaginal insert, such as a pessary. Likewise, while the pledgets and tampons of the current disclosure are generally described as being "absorbent," it will be readily apparent that the pledgets and tampons may be coated or otherwise treated to be partially or completely non-absorbent.

In an embodiment, the pledget and tampon of the current disclosure can have a contact element. In an embodiment, the contact element can allow the pledget and the tampon to respond locally to the changes in the vaginal environment and can effectively acquire fluid locally to accommodate the uniqueness of a woman's vaginal environment and her period.

Figure 1:
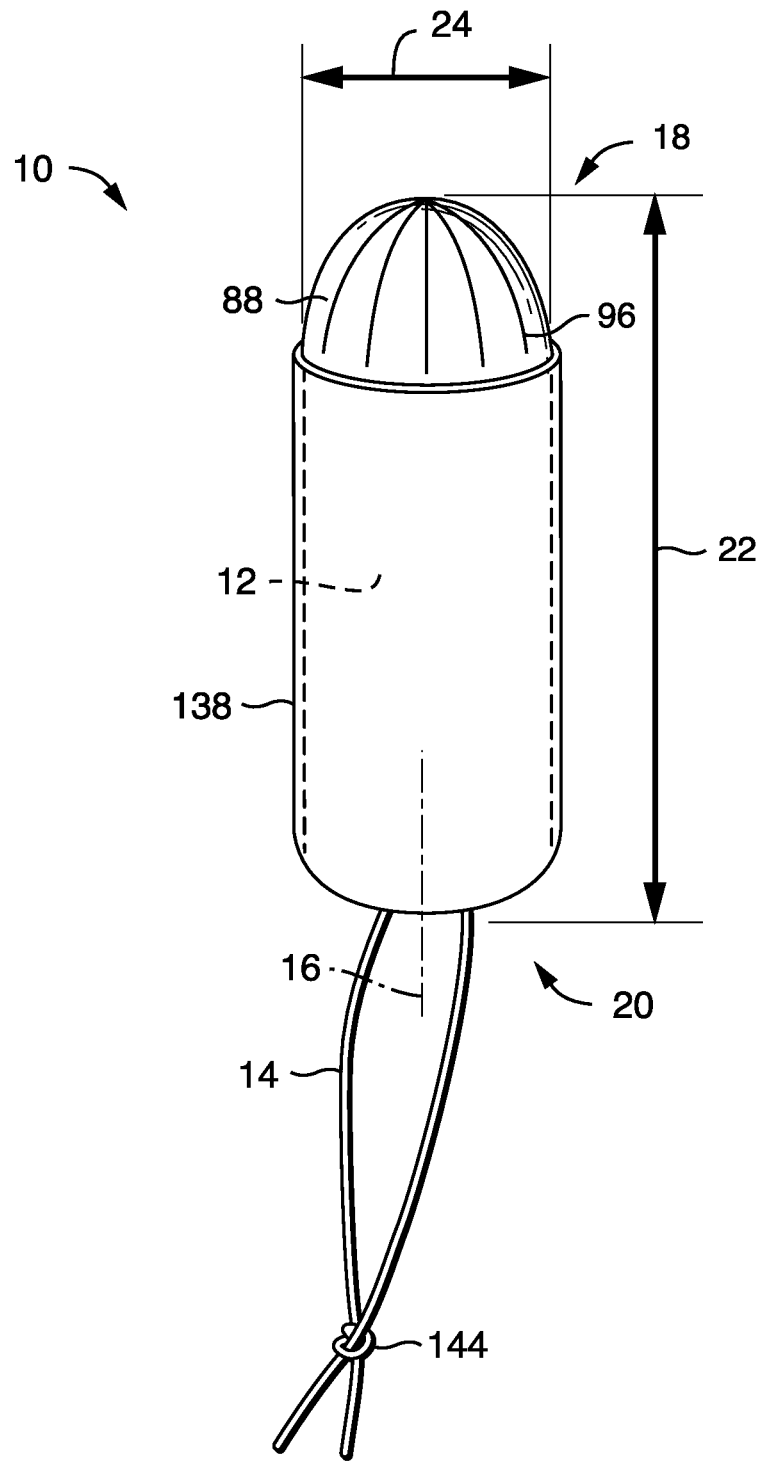
FIG. 1 is a perspective view of an embodiment of a tampon in a compressed configuration.

A non-limiting embodiment of a tampon 10 of the current disclosure is illustrated in FIG. 1. The tampon 10 can be inserted into a woman's vaginal cavity to prevent menses from exiting the vaginal opening by contacting and absorbing the flow of menses. The term "menses," as used herein, includes blood, tissue debris, and other bodily fluids emitted from the vaginal opening. The tampon 10 can have a compressed, generally cylindrical shaped pledget 12 and a withdrawal aid 14. In some embodiments, the generally cylindrical shape of the pledget 12 can have a cross-section that can be at least one of an oval, circle, square, rectangle, or any other cross-sectional shape known in the art. The term "cross-section" refers herein to the plane which extends laterally through the tampon 10, and which is orthogonal to the longitudinal axis 16 of the pledget 12, and consequently, of the tampon 10. The tampon 10 can have an insertion end 18 and a withdrawal end 20. The tampon 10 can have a length 22 wherein the length 22 is the measurement of the tampon 10 along the longitudinal axis 16 originating at one end (insertion or withdrawal) of the tampon 10 and ending at the opposite end (insertion or withdrawal) of the tampon 10. In some embodiments, the tampon 10 can have a length 22 from about 30 mm to about 80 mm. The tampon 10 can have a width 24, which unless otherwise stated herein, can correspond to the greatest cross-sectional dimension along the longitudinal axis 16 of the tampon 10. In some embodiments, the tampon 10 can have a compressed width 24 prior to usage from about 2, 5, 8, 10, 12, or 14 mm to about 20 or 30 mm. The tampon 10 may be straight or non-linear in shape, such as curved along the longitudinal axis 16.

As noted above, the tampon 10 can have a pledget 12. The pledget 12 can be formed from a blank 28, such as a softwind, wherein the blank 28 can be formed from a fleece 30. The fleece 30 can have an absorbent structure 34 which can be a single layer of a fibrous material or can be multiple layers of fibrous material. In an embodiment, an absorbent structure 34 can be formed of at least two layers of fibrous materials. The absorbent structure 34 can be manufactured via processes such as, for example, a multi-bank laydown, bonding preformed layers together, or a combination thereof. Such processes can produce a nonwoven ribbon 32 having an absorbent structure 34 of a single layer or multiple layers of fibrous materials. In an embodiment, the nonwoven ribbon 32 can be separated into individual units of fleece 30, wherein each unit of fleece 30 can have the absorbent structure 34.

In an embodiment in which the absorbent structure 34 is multi-layered, the absorbent structure 34 can have at least 2, 3, 4, 5, 6, or 7 layers of fibrous material. In an embodiment in which the absorbent structure 34 is multi-layered, a layer can be identical to another layer, can be different from another layer, or can be identical to at least one other layer and can be different from at least one other layer. In an embodiment in which an absorbent structure 34 is multi-layered and at least one layer is different from another layer, the layers can be different from each other by at least 1, 2, 3, 4 or 5 aspects.

Non-limiting examples of aspects of differences can include density, thickness, type of fibrous material in a layer, amount of fibrous material in a layer, hydrophilic/hydrophobic characteristics, and strength/integrity characteristics (which can include reinforcing fibrous materials).

In an embodiment in which the absorbent structure 34 is multi-layered, the absorbent structure 34 can be manufactured by bonding at least two pre-formed layers together. In such an embodiment, the pre-formed layers can be brought into contact with each other and bonded together by any suitable method. In such an embodiment, the bonded layers can then be bonded to at least one additional layer. The at least one additional layer can be pre-formed or can be a laid down fibrous material.

In an embodiment in which the absorbent structure 34 is multi-layered, the absorbent structure 34 can be manufactured via a process such as a multi-bank fibrous material laydown. In such a process, fibrous material in a first bank can be laid down to form a first layer and fibrous material in a second bank can be laid down onto the first layer and formed into a second layer. The second layer can then, if desired, be bonded to the first layer. In an embodiment, fibrous material in at least one additional bank can be laid down onto the prior layers and formed into at least one additional layer if so desired. The additional layer(s) can be bonded to the prior formed and bonded layers. In an embodiment, a pre-formed layer can be bonded to the formed and bonded layers.

Figure 2:
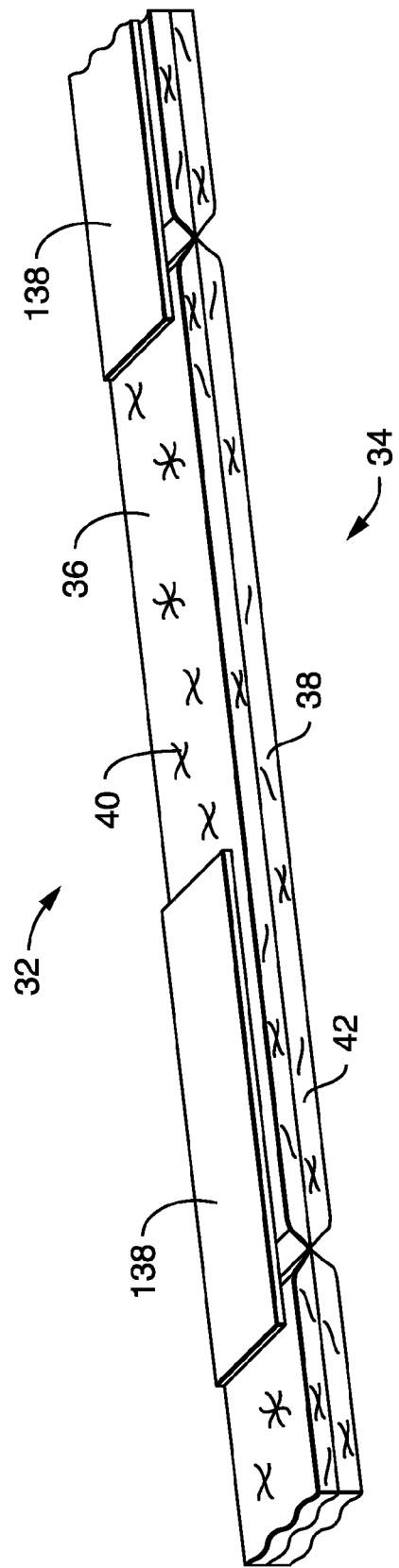
FIG. 2 is a perspective view of an embodiment of a nonwoven ribbon.

FIG. 2 provides a non-limiting illustration of a nonwoven ribbon 32 which can have a multi-layer absorbent structure 34 of at least two layers, such as layers 36 and 38. The nonwoven ribbon 32 can be manufactured via either a multi-bank fibrous material laydown method, via bonding of pre-formed layers, or via a combination of the described methods. It is to be understood that while the description and figures herein generally illustrate a nonwoven ribbon 32, an absorbent structure 34 and/or a fleece 30 having two layers, such as layers 36 and 38, a nonwoven ribbon 32, an absorbent structure 34 and/or a fleece 30 can have more than two layers and the description herein is applicable to a nonwoven ribbon 32, an absorbent structure 34 and/or a fleece 30 having more than two layers.

In an embodiment, the nonwoven ribbon 32 can have more than two layers. In an embodiment, a layer(s), such as layer(s) 36 and/or 38, can be hydrophobic or hydrophilic. In an embodiment, a layer(s), such as layer(s) 36 and/or 38, can be treated with a surfactant or other material to make the layer(s) hydrophilic or to make the layer(s) more hydrophilic. As will be described herein, in a nonwoven ribbon 32 having more than one layer, the layers, such as layers 36 and 38, can be in communication with each other. In an embodiment, the layers, such as layers 36 and 38, can be in communication with each other and can be bonded to each other. The terms "bonded" or "bonding" refer herein to the joining, adhering, connecting, attaching or the like of two elements. Two elements will be considered bonded together when they are joined, adhered, connected, or attached directly to one another or indirectly to one another, such as when each is directly joined, adhered, connected or attached to intermediate elements. The bonding can occur by any method deemed suitable including, but not limited to, adhesives, heat bonding, vibration energy, mechanical bonding, chemical bonding, vacuum bonding, ultrasonic bonds, thermal bonds, pressure bonds, mechanical entanglement, hydroentanglement, microwave bonds, or any other conventional technique. The bonding can be continuous or it can be intermittent.

Each layer, such as layers 36 and 38, can be constructed from fibrous materials, such as fibrous materials 40 and 42, respectively. In an embodiment, the fibrous materials can include absorbent fibers. The fibrous materials can include, but are not limited to, natural and synthetic fibers such as, but not limited to, polyester, acetate, nylon, cellulosic fibers such as wood pulp, cotton, rayon, viscose, LYOCELL® such as from Lenzing Company of Austria, or mixtures of these or other cellulosic fibers. Natural fibers can include, but are not limited to, wool, cotton, flax, hemp and wood pulp. Wood pulps can include, but are not limited to, standard softwood fluffing grade such as CR-1654 (US Alliance Pulp Mills, Coosa, Ala.) Pulp may be modified in order to enhance the inherent characteristics of the fibers and their processability. Crimping can be imparted to the fibers by any means deemed suitable by one of ordinary skill. Curl may be imparted to the fibers by suitable methods such as, for example, chemical treatment or mechanical twisting. Curl can be imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Pulp may also be stiffened by the use of heat or caustic treatments such as mercerization. Examples of these types of fibers include NHB416, which is a chemically cross-linked southern softwood pulp fiber which enhances wet modulus, available from Weyerhaeuser Corporation of Tacoma, Wash. Other non-limiting examples of useful pulps are debonded pulp (NF405) and non-debonded pulp (NB416) also from Weyerhaeuser. HPZ3 from Buckeye Technologies, Inc. of Memphis, Tenn., is an example of a fiber that has a chemical treatment that sets in a curl and twist, in addition to imparting added dry and wet stiffness and resilience to the fiber. Another suitable pulp is Buckeye HP2 pulp and still another is IP Supersoft from International Paper Corporation. The fibrous materials can include any suitable blend of fibers. For example, the fibrous materials can be formed from cellulose fibers such as cotton and rayon. The fibrous materials can be 100 wt % cotton, 100 wt % rayon, or a blend of cotton and rayon. In some embodiments, the cellulose fibers may be modified for super-absorbency. In an embodiment, a layer, such as layer 36 or 38, can have substantially the same fibrous material composition as another layer, such as layer 36 or 38. In an embodiment, a layer, such as layer 36 or 38, can have a fibrous material composition different from another layer, such as layer 36 or 38.

In an embodiment, the fibrous materials can have a staple length of from about 5, 10, 15 or 20 mm to about 30, 40 or 50 mm. In an embodiment, the fibrous materials can have a fiber size of from about 15 microns to about 28 microns. In an embodiment, the fibrous materials can have a denier of from about 1 or 2 to about 6. Denier is a unit of fineness of yarn based on a standard of 50 milligrams (mg) for 450 meters of yarn. The fibrous materials can have a circular, bi-lobal or tri-lobal cross-sectional configuration or any other configuration known to those skilled in the art. A bi-lobal configuration can have a cross-sectional profile which can look like a dog bone while a tri-lobal configuration can have a cross-sectional profile which can look like a "Y." In an embodiment, the fibrous materials can be bleached. In an embodiment, the fibrous materials can have a color.

In an embodiment, a layer(s), such as layer(s) 36 and/or 38, can contain fibrous materials such as binder fibers. In an embodiment, the binder fibers can have a fiber component which can bond or fuse to other fibers in the layer. Binder fibers can be natural fibers or synthetic fibers. Synthetic fibers can include, but are not limited to, those made from polyolefins, polyamides, polyesters, rayon, acrylics, viscose, super-absorbents, LYOCELL® regenerated cellulose and any other suitable synthetic fiber known to those skilled in the art. Non-limiting examples of polyolefins can include, but are not limited to, polyethylene such as Dow Chemical's ASPUN® 6811A linear low density polyethylene, 2553 LLDPE and 25355 and 12350 high density polyethylene. The polyethylenes can have melt flow rates, respectively, of about 26, 40, 25, and 12. Non-limiting examples of fiber forming polypropylenes can include, but are not limited to, Exxon Chemical Company's ESCORENE® PD 3445 polypropylene and Montell Chemical Company's PF304. Another example of a fiber can be a bi-component polyethylene sheath and polyester core known as T255 made by Trevira of Germany. Other non-limiting examples of meltable bicomponent fibers can include, but are not limited to, fibers available from Unitika of Japan, such as, for example, Unitika MELTY 4080, and 6080 fibers, having either polyester sheaths or cores and polyethylene sheaths or cores. Another example can include, but is not limited to, fibers available from Fibervisions under the designation ETC Bounce fiber line, such as PET/PE fibers of about 2.2 decitex and about 40 mm staple fiber length. Non-limiting examples of rayon fibers include 1.5 denier Merge 18453 fibers from Accordis Cellulose Fibers Inc. of Axis, Ala. The fibrous materials can be treated by conventional compositions and/or processes to enable or enhance wettability.

In an embodiment, a layer(s), such as layer(s) 36 and/or 38, can contain fibrous materials such as cellulosic fibers, such as cotton and rayon. In an embodiment, a layer(s), such as layer(s) 36 and/or 38, can be 100% cotton, 100% rayon, or a blend of cotton and rayon fibers. In an embodiment, a blend of cotton and rayon fibers can be a blend of about 15% cotton and about 85% rayon; about 70% cotton and about 30% rayon; about 60% cotton and about 40% rayon; about 25% cotton and about 75% rayon; or a blend of about 6% cotton and about 94% rayon. The blend of cotton and rayon can be any blend as deemed suitable. In an embodiment, additional fibers such as polyester or other synthetic fibers can be added to the blend of cotton and rayon to add resilient features or bondability to a layer(s), such as layer(s) 36 and/or 38.

In an embodiment, a layer(s), such as layer(s) 36 and/or 38, can have a blend of viscose and binder fibers. In an embodiment, a blend of viscose and binder fibers can be a blend of from about 70% viscose to about 95% viscose with the remainder from about 30% to about 5% binder fiber. In an embodiment, a blend of viscose and binder fibers can be a blend of from about 85-90% viscose and the remainder from about 15-10% binder fiber. The blend of viscose and binder fibers can be any blend as deemed suitable.

Various methods known to those skilled in the art can be used to prepare each layer, such as layers 36 and 38. Such methods can include, but are not limited to, airlaying, carding, wetlaying, needlepunching, mechanical entanglement, hydroentangling, and any other known method deemed suitable by one of ordinary skill In an embodiment, a bonded carded web can be made from staple fibers. In such an embodiment, the fibers can be longer than about 20, 30 or 35 mm. The fibers can be purchased in bales which can be placed in a picker to separate the fibers. The fibers can then be sent through a combing or carding unit, which can further break apart and align the staple fibers in the machine direction to form a generally machine direction-oriented fibrous nonwoven web. Once the web is formed, it can then be bonded by one or more of several known bonding methods, such as through air bonding or pattern bonding. In an embodiment, a dry laid web can be made from staple fibers. In such an embodiment, the fibers can be about 20 mm or longer. In dry laying, fibers or tufts of fibers of a first type (e.g., absorbent fibers and/or binder fibers) can be fed to a first rotating vacuum drum and fibers or tufts of fibers of a second type (e.g., absorbent fibers and/or binder fibers) can be fed to a second rotating vacuum drum. The fibers can then be laid down by suction to form mats of fibers. The mats of fibers can be doffed from the vacuum drums and combed via rotating lickerins. The lickerins can have peripheral teeth which can comb the fibers from the mat. The combed fibers can be doffed from the lickerins via centrifugal force and placed into a fiber mixing and expansion chamber. The mixed fibers can be placed on a vacuum screen to form a random fiber web comprising the first and second fiber types. The flow and velocity of each independent fiber stream can be controlled to provide the desired quantity of each fiber type. It is to be understood that a layer, such as layer 36 or 38, can be prepared using the same method as another layer, such as layer 36 or 38, or using a method different than another layer, 36 or 38.

In an embodiment, at least one of the layers, such as layers 36 and/or 38, can be prepared using an airlaying process. In such an embodiment, the airlaid fibers can contain a first fiber and a second fiber, wherein the first fiber can be a binder fiber and the second fiber can be an absorbent fiber.

In an embodiment in which binder fibers are present, the binder fibers can be activated to create a three-dimensional fiber matrix. In such an embodiment, the activation can be completed by any suitable heating step including, but not limited to, convection heating, through air heating, superheated steam, microwave heating, radiant heating, radio frequency heating, and the like, and combinations thereof. In some embodiments, the activation can be accomplished by heating the layer(s), such as layer(s) 36 and/or 38, containing the binder fibers at a temperature of from about 240° F. to about 330° F. (about 115 to about 165° C.) to activate the binder fibers. It is to be understood that the bonding temperature selected should be selected based upon the fibrous materials which are being bonded together. Without being bound by theory, it is believed that during activation, the binder fibers can soften and become tacky and, therefore, bind to adjacent fibers creating a three-dimensional fiber matrix. It is believed that the three-dimensional fiber matrix can stabilize the layer(s), such as layer(s) 36 and/or 38, and can create a liquid stable network. It is to be understood that an additional component or finish can be added to the fibers to facilitate bonding of fibrous materials which are not necessarily compatible.

In an embodiment, the activation can be followed by a cooling step which can utilize any suitable means for reducing the temperature of the layer(s), such as layer(s) 36 and/or 38. In an embodiment, the layer(s), such as layer(s) 36 and/or 38, can be cooled by allowing the layer(s), such as layer(s) 36 and/or 38, to return to ambient temperature over a period of time. In an embodiment, the layer(s), such as layer(s) 36 and/or 38, can be cooled by chill rolls, cooling chambers, blowing conditioned air, or the like, and combinations thereof. In an embodiment, the cooling step can occur prior to compression of the layer(s), such as layer(s) 36 and/or 38, to establish a wet-stable three-dimensional structure.

In some embodiments, a layer(s), such as layer(s) 36 and/or 38, can be further manipulated such as, for example, being folded, corrugated, or otherwise processed.

The nonwoven ribbon 32 can be separated into individual units of fleece 30. The separation of the nonwoven ribbon 32 into individual units of fleece 30 can occur by any suitable method such as stretching, perforating, cutting such as with the use of a die cutter or a knife cutter, and the like. The individual units of fleece 30 can then be rolled, stacked, folded, or otherwise manipulated into blanks 28. The blanks 28 can then be formed into pledgets 12 in any manner deemed suitable. As a non-limiting example, the blanks 28 can undergo compression to form the pledgets 12.

In various embodiments, the fleece 30 and the resultant pledget 12 can have any suitable combination and ratio of fibrous material. In an embodiment, the fleece 30 and the resultant pledget 12 can have from about 70 to about 95 wt % absorbent fibers and from about 5 to about 30 wt % binder fibers. In an embodiment, the fleece 30 and the resultant pledget 12 can have from about 80 to about 90 wt % absorbent fibers and from about 10 to about 20 wt % binder fibers. In an embodiment, the fleece 30 and the resultant pledget 12 can have about 85 wt % absorbent fibers and about 15 wt % binder fibers. In an embodiment, the fleece 30 and the resultant pledget 12 can have from about 80 to about 90 wt % trilobal viscose rayon fibers and from about 10 to about 20 wt % bicomponent binder fibers. In an embodiment, the fleece 30 and the resultant pledget 12 can have about 85wt % trilobal viscose rayon fibers and about 15 wt % bicomponent binder fibers. In an embodiment, the fleece 30 and the resultant pledget 12 can have greater than about 50, 55, 60, 65, 70, 80, 90, 95, 97, or 99 wt % absorbent fibers.

The fleece 30 can be any size and thickness that can ultimately be compressed into a pledget 12 having a vaginally insertable shape. In an embodiment, the size of the fleece 30 can range from about 40 mm to about 100, 200, 250 or 300 mm in width and from about 30 mm to about 80 mm in length. As described herein, the width of the fleece 30 can be measured as the distance between longitudinal edges of the fleece 30 and the length of the fleece 30 can be measured as the distance between transverse edges of the fleece 30. As described herein, the transverse edges of the fleece 30 can be located at the insertion and withdrawal ends, 18 and 20, respectively, of a resultant tampon 10. In an embodiment, the overall basis weight of the fleece 30 can range from about 15, 20, 25, 50, 75, 90, 100, 110, 120, 135 or 150 gsm to about 1,000, 1,100, 1,200, 1,300, 1,400, or 1,500 gsm.

Figure 3:
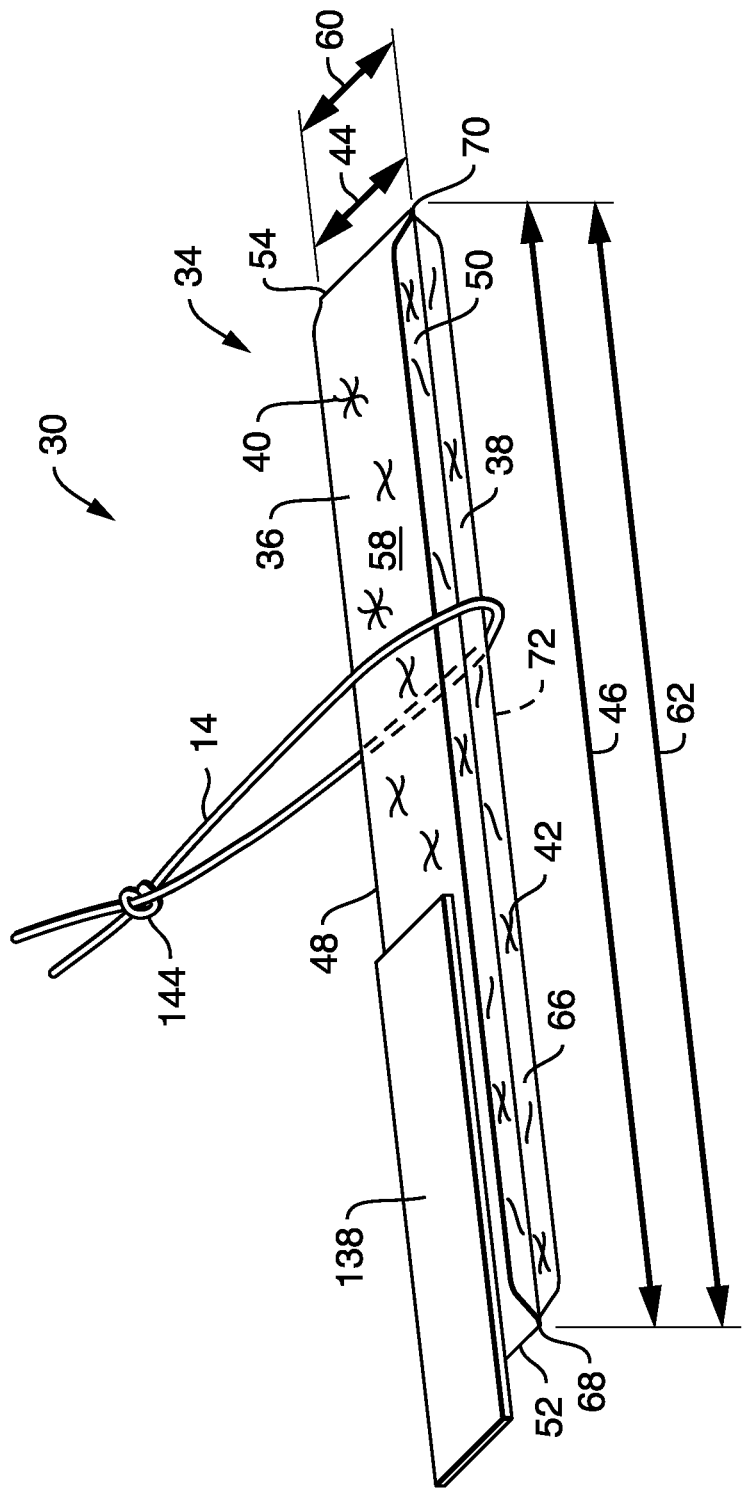
FIG. 3 is a perspective view of an embodiment of a fleece.

Referring to FIG. 3, a non-limiting example of a fleece 30 is illustrated in which the fleece 30 can have a multi-layer absorbent structure 34 of two layers, 36 and 38. In the non-limiting example illustrated, the first layer 36 can have a first length 44 and a first width 46. The first length 44 can extend from a first transverse edge 48 to a second transverse edge 50 of the first layer 36. The first width 46 can extend from a first longitudinal edge 52 to a second longitudinal edge 54 of the first layer 36. The first layer 36 can have a first surface 56 (illustrated in FIG. 4) and a second surface 58. Similarly, the second layer 38 can have a second length 60 and a second width 62. The second length 60 can extend from a first transverse edge 64 (illustrated in FIG. 4) to a second transverse edge 66 of the second layer 38. The second width 62 can extend from a first longitudinal edge 68 to a second longitudinal edge 70 of the second layer 38. The second layer 38 can have a first surface 72 and a second surface 74 (illustrated in FIG. 4). In a resultant tampon 10, the transverse edges of each layer, 36 and 38, can be located at the insertion end 18, the withdrawal end 20 or, as described herein, a location between the insertion end 18 and the withdrawal end 20. As a non-limiting example with regards to the fleece 30 illustrated in FIG. 3, transverse edges 50 and 66 can be located at the insertion end 18 of a resultant tampon 10 and transverse edges 48 and 64 can be located at the withdrawal end 20 of a resultant tampon 10.

The absorbent structure 34 can be constructed such that one of the surfaces, 56 or 58, of the first layer 36 can be at least partially in a face to face relationship with one of the surfaces, 72 or 74, of the second layer 38. In an embodiment, at least about 25% of one of the surfaces, 72 or 74, of the second layer 38 can be in a face to face relationship with one of the surfaces, 56 or 58, of the first layer 36. In an embodiment, at least about 25, 30, 35, 40, 45, 50, 55, 60, 65, 70, 75, 80, 85, 90, 95 or 100% of one of the surfaces, 72 or 74, of the second layer 38 can be in a face to face relationship with one of the surfaces, 56 or 58, of the first layer 36. In an embodiment, less than 100% of one of the surfaces, 72 or 74, of the second layer 38 can be in a face to face relationship with one of the surfaces, 56 or 58, of the first layer 36. In an embodiment, from about 25, 30, 35, 40, 45, or 50% to about 55, 60, 65, 70, 75, 80, 85, 90, 95 or 100% of one of the surfaces, 72 or 74, of the second layer 38 can be in a face to face relationship with one of the surfaces, 56 or 58, of the first layer 36.

In the exemplary illustration of FIG. 3, the first and second layers, 36 and 38, are illustrated as being substantially coextensive with each other. In such an embodiment, the first length 44 of the first layer 36 can be substantially the same as the second length 60 of the second layer 38. The first width 46 of the first layer 36 can be substantially the same as the second width 62 of the second layer 38. In the exemplary illustration of FIG. 3, about 100% of the first surface 56 of the first layer 36 can be in a face to face relationship with the second surface 74 of the second layer 38. As described herein, a withdrawal aid 14 and a cover 138 can be associated with the fleece 30.

In an embodiment, the fleece 30 can have a multi-layer absorbent structure 34 in which one of the layers, 36 or 38, can have a length and/or width different from the other layer, 36 or 38. Referring to FIGS. 4-8, non-limiting examples of embodiments of absorbent structures 34 are illustrated in which one layer, 36 or 38, can have a length and/or width different from the other layer, 36 or 38.

Figure 4:
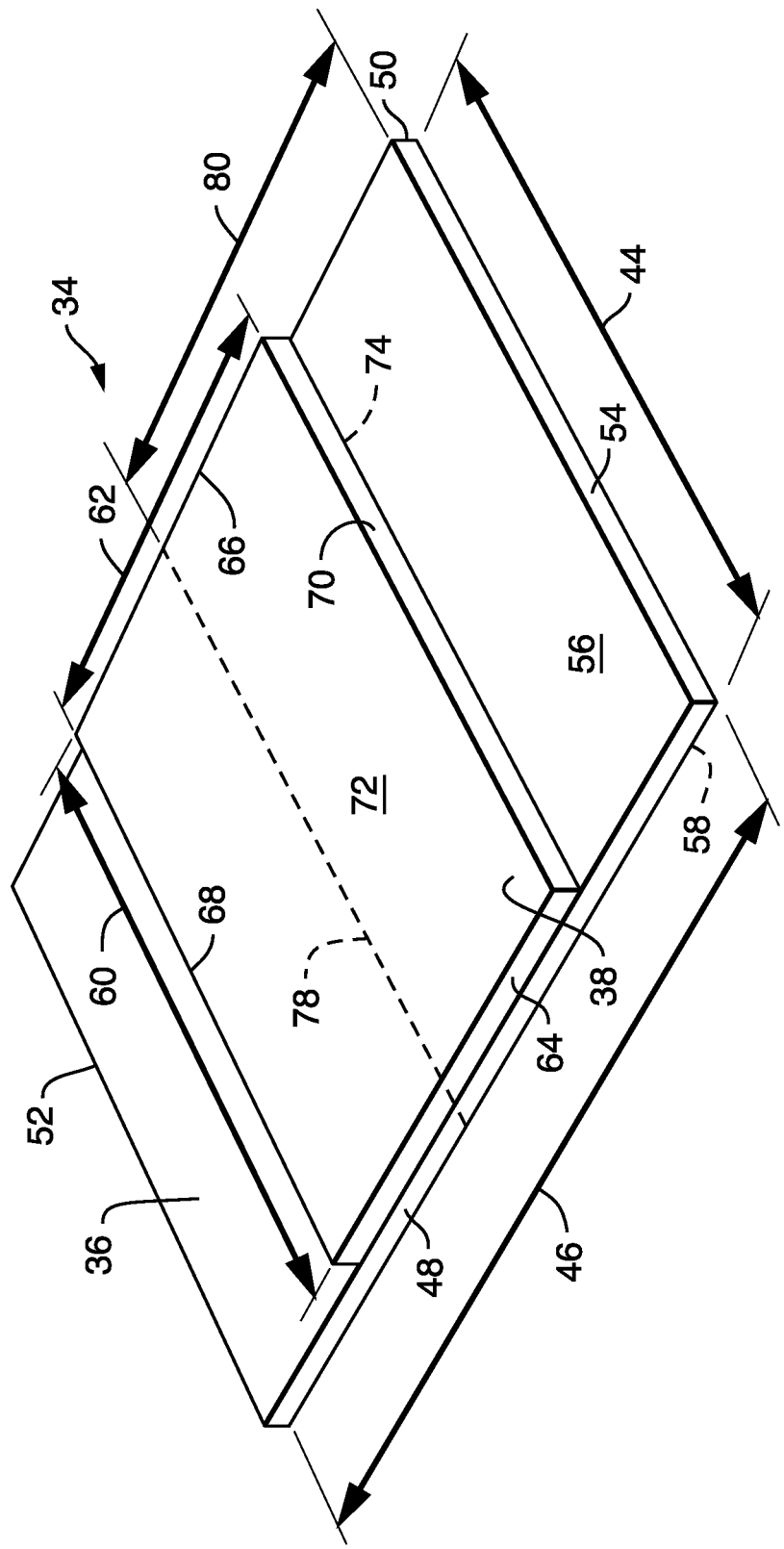
FIG. 4 is a perspective view of an embodiment of an absorbent structure.

FIG. 4 provides an illustration of a non-limiting example of an embodiment of a multi-layer absorbent structure 34 in which the first layer 36 can have a first width 46 greater than the second width 62 of the second layer 38. As illustrated in FIG. 4, the first length 44 of the first layer 36 can be substantially similar to the second length 60 of the second layer 38. In the non-limiting example illustrated in FIG. 4, the second layer 38 can be bonded to the central region of the first width 46 of the first layer 36. The central region of the first width 46 can be the area adjacent a center line 78 of the first width 46 of the first layer 36 of the absorbent structure 34. It is to be understood that the central region of the first width 46 does not need to be the exact center of the first layer 36, but can be located generally around the center line 78 of the first width 46. In an embodiment, the central region of the first width 46 of the first layer 36 can be a position along the first width 46 which is a distance 80 that is about 0.35 to about 0.65 times the first width 46, as measured from either longitudinal edge, 52 or 54, of the first layer 36. It is to be understood that the second layer 38 does not have to be bonded to the first layer 36 in the central region of the first width 46, but rather could be bonded to the first layer 36 in an area adjacent to one of the longitudinal edges, 52 or 54, or at any other position along the first width 46 of the first layer 36 as deemed suitable.

Figure 5:
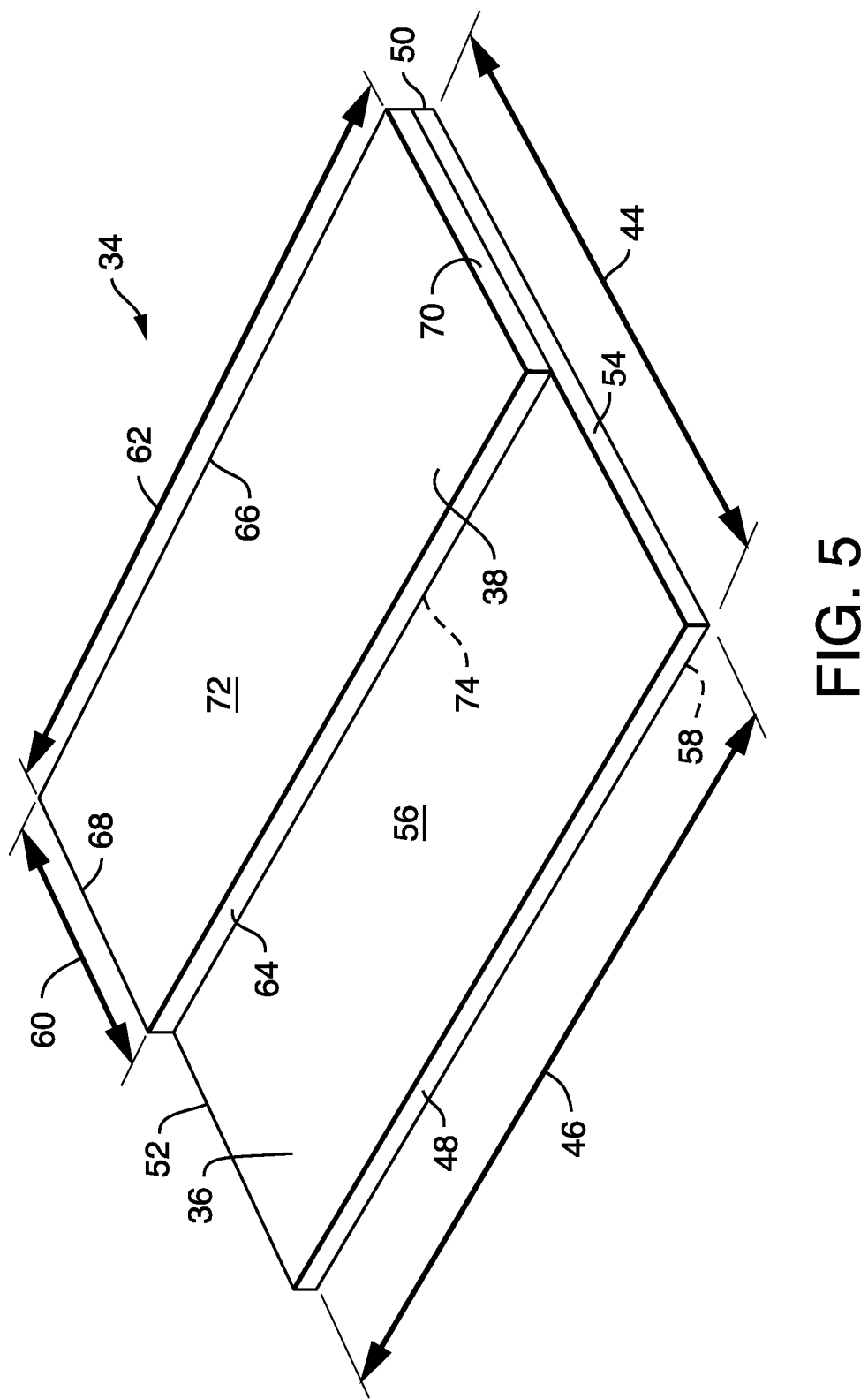
FIG. 5 is a perspective view of an embodiment of an absorbent structure.

FIG. 5 provides an illustration of a non-limiting example of an embodiment of a multi-layer absorbent structure 34 in which the first layer 36 can have a first length 44 greater than the second length 60 of the second layer 38. As illustrated in FIG. 5, the first width 46 of the first layer 36 can be substantially similar to the second width 62 of the second layer 38. In the non-limiting example illustrated in FIG. 5, the second layer 38 can be bonded adjacent to one of the transverse edges, 48 or 50, such as transverse edge 50, of the first layer 36. It is to be understood that the second layer 38 can be bonded to the first layer 36 at any position along the first length 44 of the first layer 36 as deemed suitable.

Figure 6:
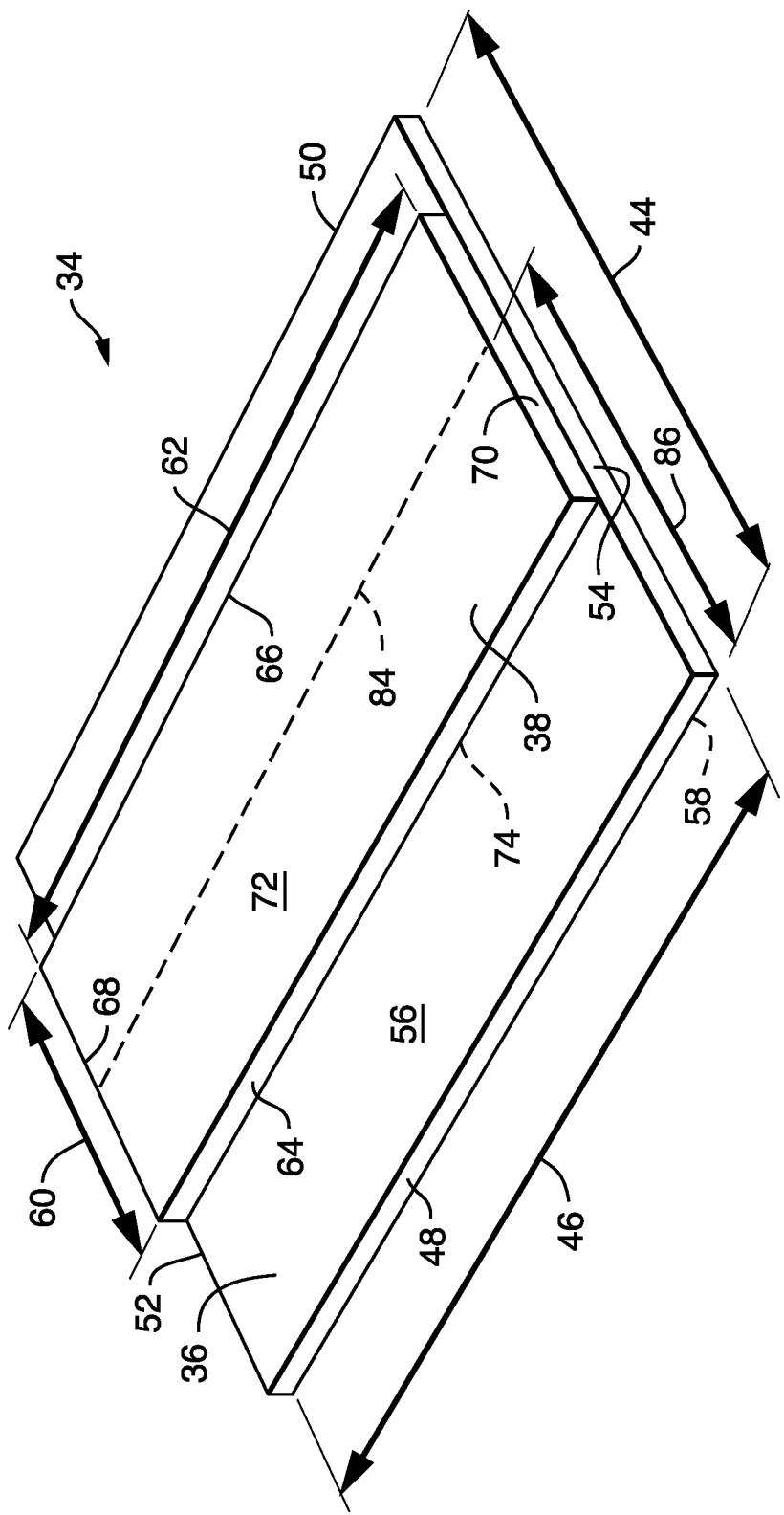
FIG. 6 is a perspective view of an embodiment of an absorbent structure.

FIG. 6 provides an illustration of a non-limiting example of an embodiment of an absorbent structure 34 in which the first layer 36 can have a first length 44 greater than the second length 60 of the second layer 38. As illustrated in FIG. 6, the first width 46 of the first layer 36 can be substantially similar to the second width 62 of the second layer 38. In the non-limiting example illustrated in FIG. 6, the second layer 38 can be bonded in the central region of the first length 44 of the first layer 36. The central region of the first length 44 can be the area adjacent a center line 84 of the first length 44 of the first layer 36 of the absorbent structure 34. It is to be understood that the central region of the first length 44 does not need to be the exact center of the first layer 36, but can be located generally around the center line 84 of the first length 44. In an embodiment, the central region of the first layer 36 can be a position along the first length 44 which can be a distance 86 that can be about 0.35 to about 0.65 times the first length 44, as measured from either transverse edge, 48 or 50, of the first layer 36. In an embodiment, the second layer 38 does not have to be bonded to the first layer 36 in the central region of the first length 44, but rather could be bonded to the first layer 36 in an area adjacent to one of the transverse edges, 48 or 50, or at any other position along the first length 44 of the first layer 36 as deemed suitable.

Figure 7:
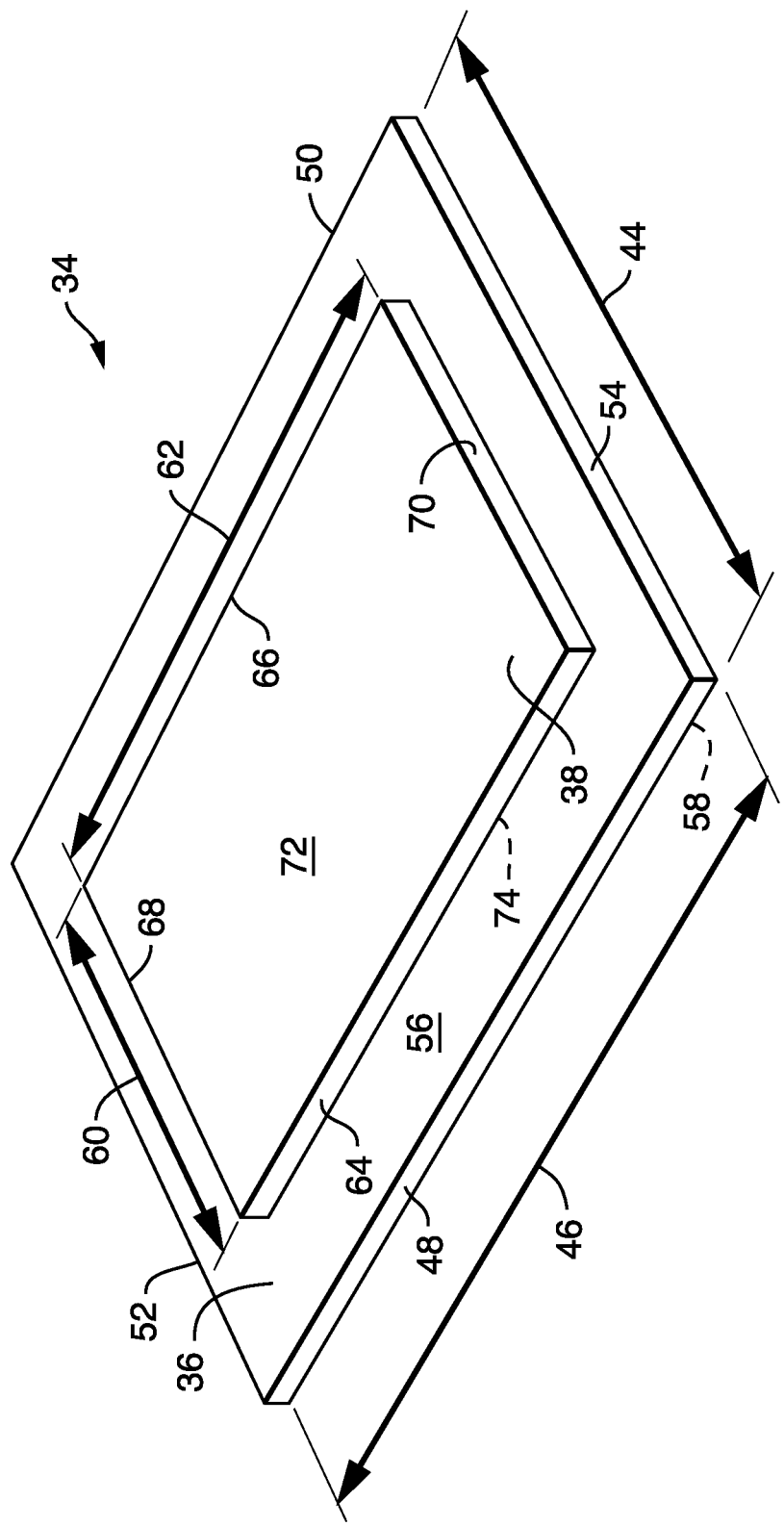
FIG. 7 is a perspective view of an embodiment of an absorbent structure.
Figure 8:
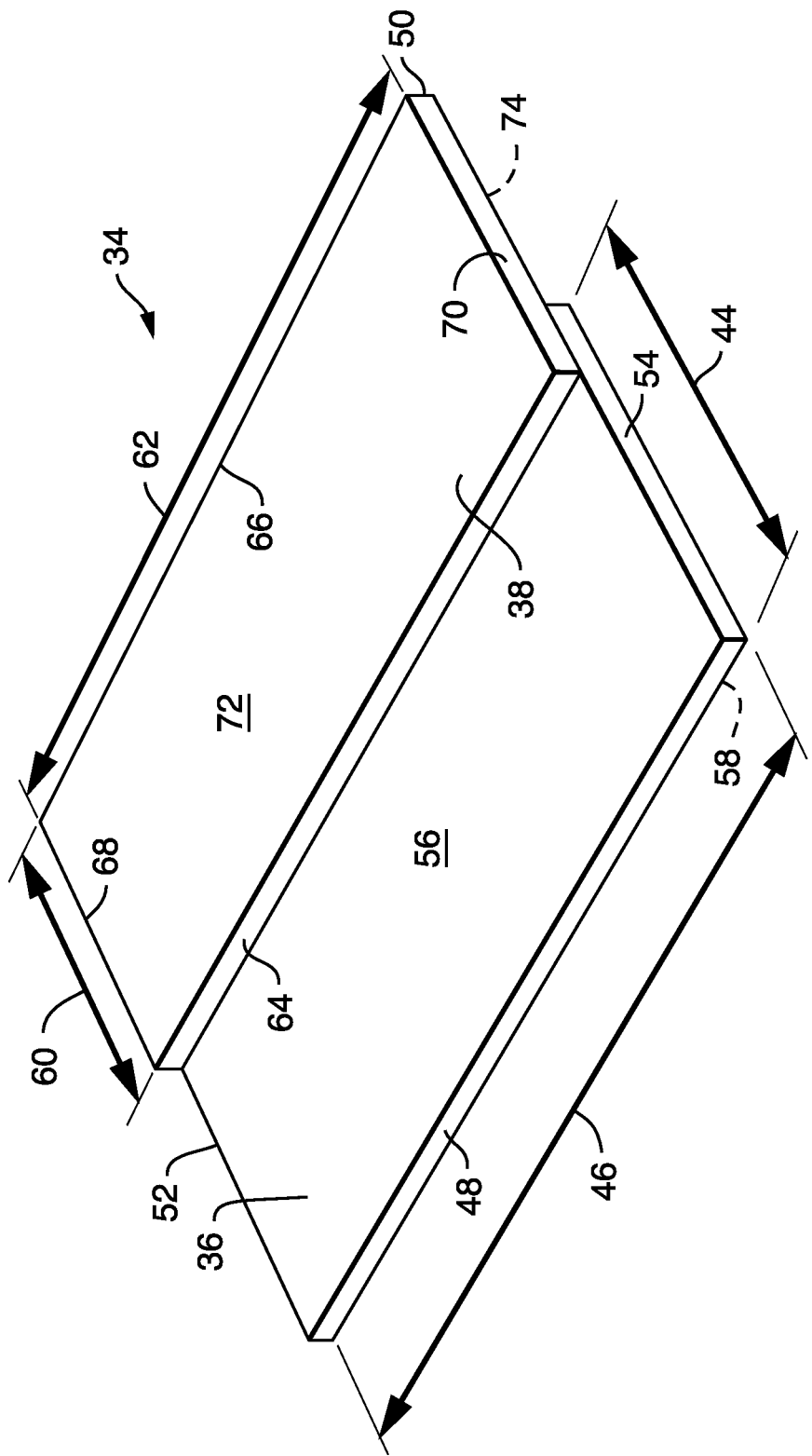
FIG. 8 is a perspective view of an embodiment of an absorbent structure.

FIG. 7 provides an illustration of a non-limiting example of an embodiment of an absorbent structure 34 in which the first layer 36 is illustrated as having a first length 44 and a first width 46 that are each greater than the second length 60 and the second width 62 of the second layer 38. FIG. 8 provides an illustration of a non-limiting example of an absorbent structure 34 in which less than 100% of surface 74 of second layer 38 can be in a face to face relationship with surface 56 of first layer 36. First width 46 can be substantially similar to second width 62, however it should be realized that first width 46 can be greater than or less than second width 62. First length 44 can be greater than, less than, or substantially similar to second length 60.

In an embodiment in which a layer, such as layer 36 or 38, has a length and/or width smaller than a length and/or width of another layer, such as layer 36 or 38, the layer with the smaller dimension can be bonded to the layer with the larger dimension in any location as deemed suitable.

Figure 9:
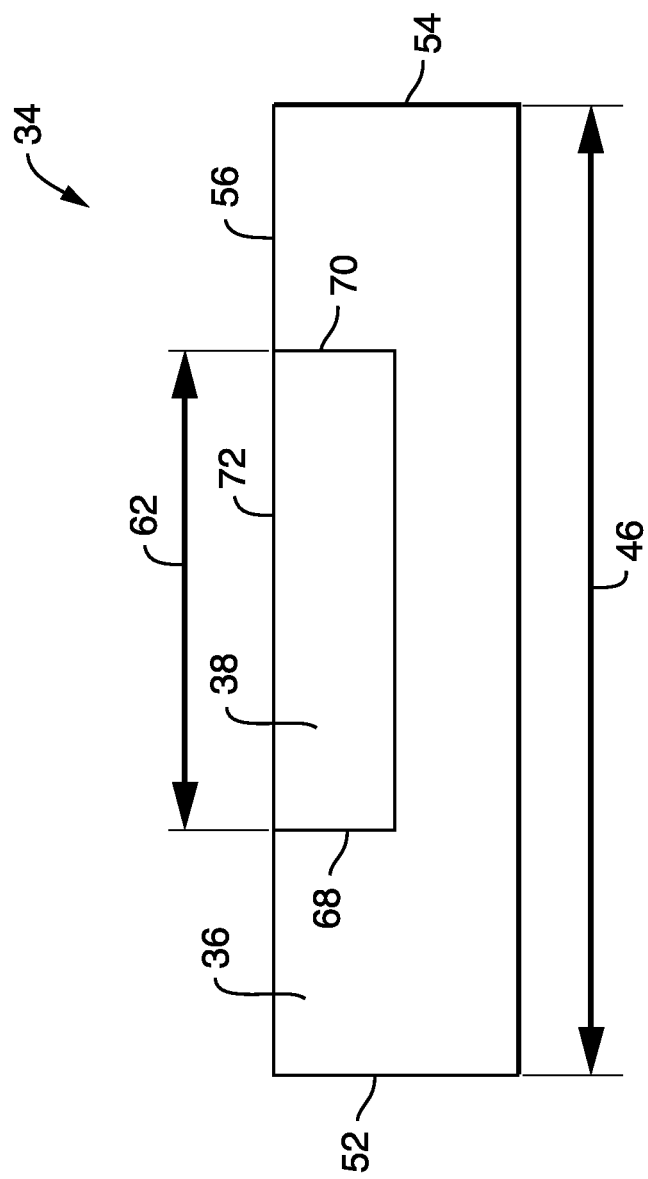
FIG. 9 is a side view of an embodiment of an absorbent structure.

FIGS. 4-8 provide non-limiting illustrations in which the second layer 38 can be positioned on top of the first layer 36. In an embodiment, the first layer 36 can be positioned on top of the second layer 38. In an embodiment, at least a portion of a layer, such as layer 36 or 38, can be inset into another layer, such as layer 36 or 38. In an embodiment, all of a layer, such as layer 36 or 38, can be inset into another layer, such as layer 36 or 38. FIG. 9 provides a non-limiting example of an embodiment of an absorbent structure 34 in which at least a portion of the second layer 38 can be at least partially inset into the first layer 36.

As described herein, each layer, such as layers 36 and 38, can have transverse edges, such as transverse edges 48 and 50 of layer 36 and transverse edges 64 and 66 of layer 38. In an embodiment, each transverse edge(s), 48, 50, 64 and/or 66, can be linear, non-linear, arcuate, and any combination thereof as deemed suitable. Such an edge can be produced in any manner as deemed suitable, such as, but not limited to, knife cutting, die cutting, or any other method known to one skilled in the art. As described herein, a transverse edge can be located at the insertion end 18, the withdrawal end 20 or a location between the insertion and withdrawal ends, 18 and 20, of a resultant tampon 10.

In an embodiment, at least one layer, such as layer(s) 36 and/or 38, of the absorbent structure 34 can have at least one contact element 88. Without being bound by theory, it is believed that when the tampon 10 is in use the contact element 88 can at least partially expand outwardly from the tampon 10 when contacted by bodily fluids. It is believed that such expansion of the contact element 88 can reduce or prevent leakage of bodily fluids from the woman's vagina.

In an embodiment, a tampon 10 can have at least one contact element 88 located at the insertion end 18 of the tampon 10. In an embodiment, a tampon 10 can have at least one contact element 88 located at the withdrawal end 20 of the tampon. In an embodiment, a tampon 10 can have at least one contact element 88 located at both the insertion end 18 and the withdrawal end 20 of the tampon 10. In an embodiment, a tampon 10 can have at least one contact element 88 at a location of the tampon 10 between the insertion end 18 and the withdrawal end 20. In an embodiment, a tampon 10 can have at least one contact element 88 at a location of the tampon 10 between the insertion end 18 and the withdrawal end 20 and at least one contact element 88 located at at least one of the insertion end 18 and/or the withdrawal end 20 of the tampon 10.

Figure 10:
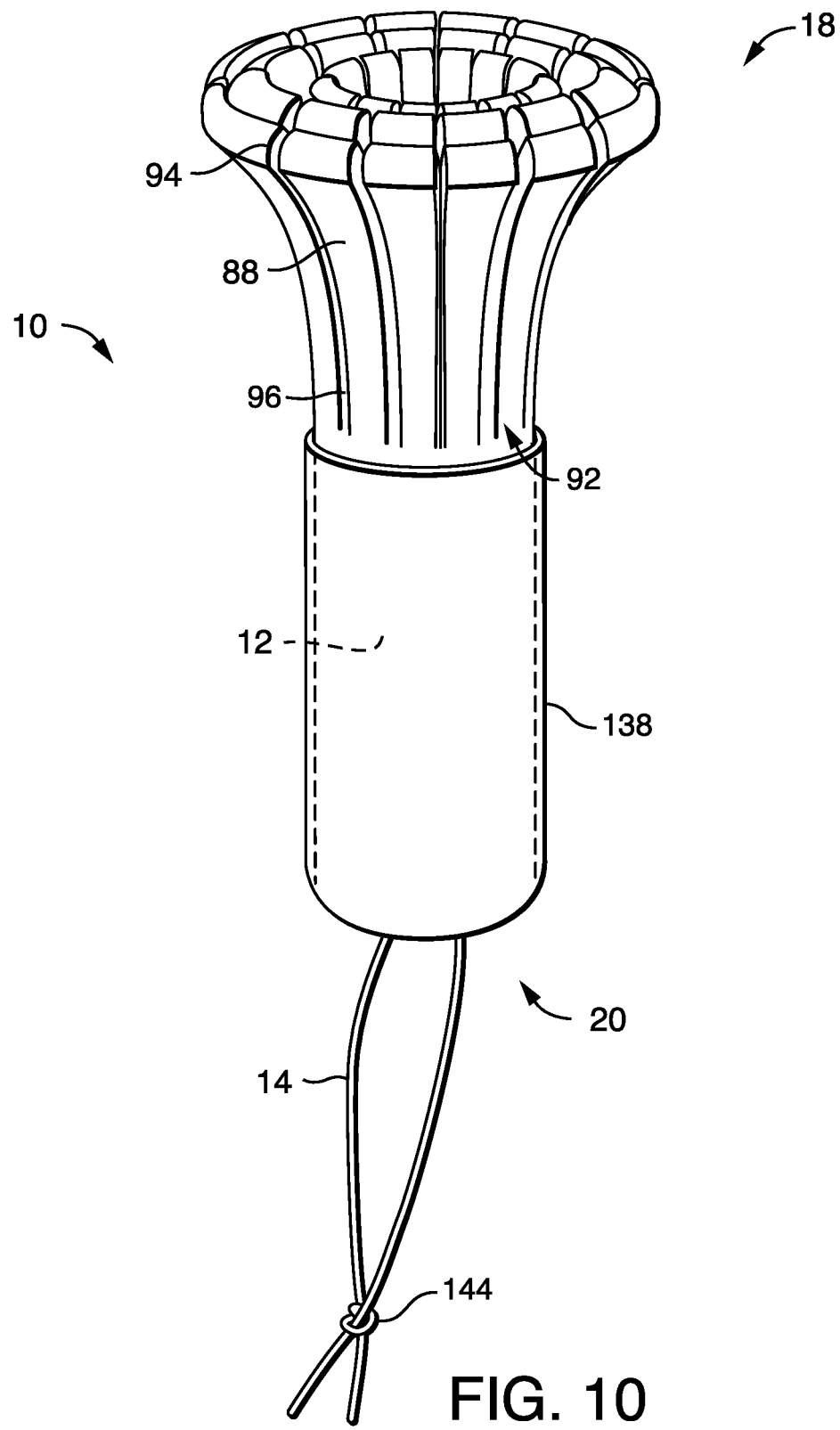
FIG. 10 is a perspective view of an embodiment of a tampon in an activated configuration.

In an embodiment, a contact element 88 can at least partially expand outwardly from the tampon 10 when contacted by body fluids. Without being bound by theory, it is believed that, while the entire tampon 10 may expand from a compressed configuration into a less compressed configuration when contacted by body fluids, when a contact element 88 is contacted by body fluids and at least partially expands away from the tampon 10 as a result of such contact, the expansion of a contact element 88 away from the tampon 10 can result in an expanded contact element 88 region having a cross-sectional diameter that is greater than a cross-sectional diameter of the remaining expanded tampon 10. FIG. 1 provides a non-limiting illustration of a compressed tampon 10 of the current disclosure. As illustrated in FIG. 1, the tampon 10 can have at least one contact element 88 located at the insertion end 18 of the tampon 10. FIG. 10 provides a non-limiting example of an activated tampon 10, i.e., an expanded tampon 10, wherein the contact elements 88 can expand away from the tampon 10 and the region of the contact elements 88 can have a greater cross-sectional diameter than the remainder of the tampon 10. As a contact element 88 expands outwardly from the tampon 10, the contact element 88 can deform and follow the folds and convolutions of the walls of the vaginal cavity in order to respond locally to the changes in the vaginal environment.

A contact element 88 can have a base 92. In an embodiment, a base 92 of at least one contact element 88 can be located at the insertion end 18 of a tampon 10. In an embodiment, a base 92 of at least one contact element 88 can be located at the withdrawal end 20 of a tampon 10. In an embodiment, a base 92 of at least one contact element 88 can be located at the insertion end 18 of a tampon 10 and a base 92 of at least one contact element 88 can be located at the withdrawal end 20 of a tampon 10. In an embodiment, a base 92 of at least one contact element 88 can be at a location between the insertion end 18 and the withdrawal end 20 of a tampon 10. In an embodiment, a base 92 of at least one contact element 88 can be at a location between the insertion end 18 and the withdrawal end 20 of a tampon 10 and a base 92 of a contact element 88 can be located at at least one of the insertion end 18 and/or the withdrawal end 20 of a tampon 10.

In an embodiment, a contact element 88 can be at least partially bounded by a free edge 94 and at least partially bounded by a base 92. In an embodiment, a portion of a free edge 94 of a contact element 88 can at least partially align with the insertion end 18 of a tampon 10. In an embodiment, a portion of a free edge 94 of a contact element 88 can at least partially align with the withdrawal end 20 of a tampon 10. In an embodiment, substantially all of the contact element 88 can be located between the insertion end 18 and the withdrawal end 20 of a tampon 10. In an embodiment, a portion of a free edge 94 of a contact element 88 can be at least partially aligned with the insertion end 18 of a tampon 10 and a portion of a free edge 94 of a contact element 88 can be at least partially aligned with the withdrawal end 20 of a tampon 10. In an embodiment, substantially all of a contact element 88 can be located between the insertion end 18 and the withdrawal end 20 and a portion of a free edge 94 of a contact element 88 can be at least partially aligned with at least one of the insertion end 18 and/or the withdrawal end 20 of a tampon 10.

In an embodiment, at least one contact element 88 can be oriented towards the insertion end 18 of the tampon 10. In an embodiment, at least one contact element 88 can be oriented towards the withdrawal end 20 of the tampon 10. In an embodiment, at least one contact element 88 can be oriented towards the insertion end 18 of the tampon 10 and at least one contact element 88 can be oriented towards the withdrawal end 20 of the tampon 10.

In an embodiment, each layer, such as layer 36 and 38, can have at least one contact element 88 located at the insertion end 18, the withdrawal end 20, or at a location between the insertion end 18 and the withdrawal end 20 of a tampon 10. In such an embodiment, a contact element 88 of a layer, such as layer 36, can be, but does not have to be, located in the same location (i.e., insertion end 18, withdrawal end 20, or a location between the insertion end 18 and the withdrawal end 20) as a contact element 88 of another layer, such as layer 38. In an embodiment, each layer, such as layer 36 and 38, can have at least one contact element 88 located at the insertion end 18 of a tampon 10. In an embodiment, each layer, such as layer 36 and 38, can have at least one contact element 88 located at the withdrawal end 20 of a tampon 10. In an embodiment, one of the layers, such as layer 36 or 38, can have at least one contact element 88 located at the insertion end 18 of a tampon 10 and another layer, such as layer 36 or 38, can have at least one contact element 88 located at the withdrawal end 20 of the tampon 10. In an embodiment, each of the layers, such as layers 36 and 38, can each have at least one contact element 88 located at each of the insertion end 18 and the withdrawal end 20 of a tampon 10. In an embodiment, one of the layers, such as layer 36 or 38, can have a contact element 88 located at at least one of the insertion end 18 and/or the withdrawal end 20 and another layer, such as layer 36 or 38, can have a contact element 88 located at a location between the insertion end 18 and the withdrawal end 20 of a tampon 10.

In an embodiment in which each of the layers, such as layers 36 and 38, have at least one contact element 88, the at least one contact element 88 of each layer, such as layers 36 and 38, can be in any overlapping relationship to each other as desired. In an embodiment, a contact element 88 of layer 36 can substantially overlap a contact element 88 of layer 38. In an embodiment, a contact element 88 of layer 36 can partially overlap a contact element 88 of layer 38. In an embodiment, a contact element 88 of layer 36 can have minimal or no overlap with a contact element 88 of layer 38.

In an embodiment, at least one of the layer(s), such as layer(s) 36 and/or 38, can have at least one contact element 88. In an embodiment, at least one of the layer(s), such as layer(s) 36 and/or 38, can have at least 1, 2, 3, 4, 5, 6, 7, 8, 9, or 10 contact elements 88. In an embodiment, at least one of the layer(s), such as layer(s) 36 and/or 38, can have from 1, 2, 3, 4, 5, 6, 7, 8, 9, or 10 to 11, 12, 13, 14, 15, 16, 17, 18, 19, or 20 contact elements 88. In an embodiment, each of the layers, such as layers 36 and 38, can each have at least one contact element 88. In an embodiment, each of the layers, such as layers 36 and 38, can have at least 1, 2, 3, 4, 5, 6, 7, 8, 9, or 10 contact elements 88. In an embodiment, each of the layers, such as layers 36 and 38, can have from 1, 2, 3, 4, 5, 6, 7, 8, 9, or 10 to 11, 12, 13, 14, 15, 16, 17, 18, 19, or 20 contact elements 88.

In an embodiment, at least one layer(s), such as layer(s) 36 and/or 38, can have at least one contact element 88 at least partially separated from another contact element 88. In an embodiment, the partial separation of one contact element 88 from another contact element 88 can occur via an amplitude of an arc, a slit, or combination thereof.

FIGS. 11-24 illustrate various non-limiting examples of embodiments of an absorbent structure 34 in which at least one layer, such as layer 36 and/or 38, can have at least one contact element 88. It is to be understood that the configurations of absorbent structures 34 and contact elements 88 described and illustrated herein are non-limiting and additional configurations are contemplated by this disclosure.

Figure 11:
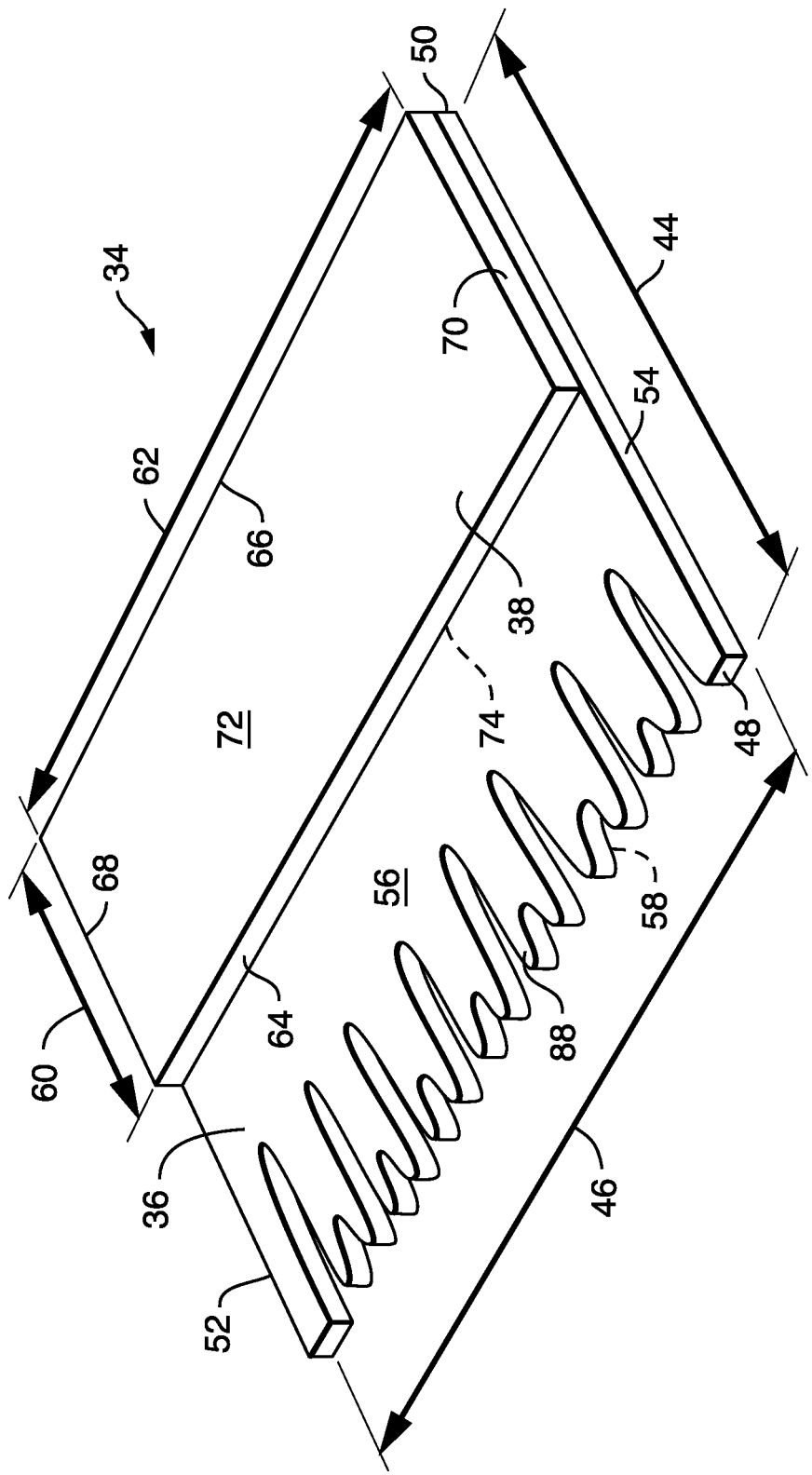
FIG. 11 is a perspective view of an embodiment of an absorbent structure with at least one contact element.

In an embodiment, a layer(s), such as layer 36 and/or 38, of an absorbent structure 34 can have a transverse edge which can have an undulating arcuate pattern. In such an embodiment, the undulating arcuate pattern can produce at least one contact element 88. The amplitude of each arc can be any amplitude as deemed suitable. In such an embodiment, a contact element 88 can be at least partially separated from another contact element 88 by the amplitude of the arc. FIG. 11 illustrates a non-limiting example of an absorbent structure 34 which can have two layers, 36 and 38. As illustrated in FIG. 11, layer 36 can have a first width 46 which can be substantially the same as the second width 62 of layer 38. As illustrated in FIG. 11, layer 36 can have a first length 44 which can be longer than a second length 60 of layer 38. Layer 36 can have two transverse edges, 48 and 50, in which transverse edge 48 can have an undulating arcuate pattern. Such an undulating arcuate pattern can produce contact elements 88 which can be at least partially separated from each other by the amplitude of an arc between each contact element 88. In an embodiment, a transverse edge having an arcuate pattern can be located at the insertion end 18 of a resultant tampon 10. In an embodiment, a transverse edge having an arcuate pattern can be located at the withdrawal end 20 of a resultant tampon 10. In an embodiment, a transverse edge having an arcuate pattern can be located at a location between the insertion end 18 and the withdrawal end 20 of a resultant tampon 10. In an embodiment, transverse edges having an arcuate pattern can be located at both the insertion end 18 and the withdrawal end 20 of a resultant tampon 10. In an embodiment, a layer(s), 36 and/or 38, can have a transverse edge having an arcuate pattern at a location between the insertion end 18 and the withdrawal end 20 and a layer(s), 36 and/or 38, can have a transverse edge having an arcuate pattern at at least one of the insertion end 18 and/or the withdrawal end 20 of the tampon 10.

In an embodiment, the free edge 94 of a contact element 88 can be generated via a slit 96. A slit 96 can extend through a layer(s), such as layer(s) 36 and/or 38, from a first surface and through to a second surface of the layer(s), such as layer(s) 36 and/or 38. For example, a slit 96 can be incorporated into layer 36, extending from a first surface 56 of layer 36 through to a second surface 58 of layer 36 to form a free edge 94 of a contact element 88. In an embodiment, a layer(s), such as layer(s) 36 and/or 38, can have at least one slit 96. In an embodiment, a layer(s), such as layer(s) 36 and/or 38, can have at least 1, 2, 3, 4, 5, 6, 7, 8, 9, or 10 slits 96. In an embodiment, a layer(s), such as layer(s) 36 and/or 38, can have from about 1, 2, 3, 4, 5, 6, 7, 8, 9, or 10 to about 11, 12, 13, 14, 15, 16, 17, 18, 19, or 20 slits 96. In an embodiment, a layer(s), such as layer(s) 36 and/or 38, can have the appropriate number of slits 96 to provide the desired number of contact elements 88.

In an embodiment, a slit 96 can be linear, arcuate, any other shape, or combination thereof. In an embodiment, a slit 96 can have any length 98 as desired. The length 98 can be measured as the distance between the terminal ends of the slit 96. In an embodiment in which the slit 96 contains an arc, the arc length can be determined by any manner deemed suitable by one of ordinary skill in order to determine the length 98 of the slit 96. In an embodiment, the length 98 of a slit 96 can range from about 1, 2, 3, 4, 5, 6, 7, 8, 9, 10, 11, 12, 13, 14 or 15 mm to about 16, 17, 18, 19, 20, 21, 22, 23, 24, 25, 26, 27, 28, 29 or 30 mm. In an embodiment, the length 98 of a slit 96 can be greater than about 1, 2, 3, 4, 5, 6, 7, 8, 9, 10, 11, 12, 13, 14 or 15 mm. In an embodiment, the length 98 of a slit 96 can be less than about 30, 29, 28, 27, 26, 25, 24, 23, 22, 21, 20, 19, 18, 17, 16, or 15 mm.

In an embodiment in which a layer, such as layer 36 or 38, has more than one slit 96, each slit 96 can have the same length 98. In an embodiment in which a layer, such as layer 36 or 38, has more than one slit 96, a slit 96 can have a length 98 that differs from the length 98 of at least one other slit 96. In an embodiment, at least about 20, 25, 40, 45, 50, 55, 70, 75, 80 or 85% of the slits 96 in a layer, such as layer 36 or 38, can have substantially the same length 98. In an embodiment, about 25, 50, or 75% of the slits in a layer, such as layer 36 or 38, can have substantially the same length, such as a first slit length, and about 25, 50, or 75% of the slits in the same layer, such as layer 36 or 38, can have substantially the same length, such as a second slit length, and the second slit length can be different from the first slit length. In an embodiment in which the slits 96 incorporated into a layer, such as layer 36 or 38, have varying slit lengths, the slits 96 can be incorporated into the layer, such as layer 36 or 38, in any pattern of slit lengths as desired.

In an embodiment, an absorbent structure 34 can have two layers, such as layers 36 and 38, in which each layer, such as layers 36 and 38, can have more than one slit 96. In an embodiment, each slit 96 in the absorbent structure 34 can have the same length 98. In an embodiment, the absorbent structure 34 can have a slit 96 that can have a length 98 that differs from the length 98 of at least one other slit 96 located within the absorbent structure 34. In an embodiment, at least about 20, 25, 40, 45, 50, 55, 70, 75, 80 or 85% of the slits 96 in the absorbent structure 34 can have substantially the same length 98. In an embodiment, about 25, 50, or 75% of the slits 96 in the absorbent structure 34 can have substantially the same length, such as a first slit length, and about 25, 50, or 75% of the slits 96 in the absorbent structure 34 can have substantially the same length, such as a second slit length, and the second slit length can be different from the first slit length. In an embodiment in which the slits 96 incorporated into the absorbent structure 34 have varying slit lengths, the slits 96 can be incorporated into the absorbent structure 34 in any pattern of slit lengths as desired.

In an embodiment, a slit 96 can be incorporated into at least one layer(s), such as layer(s) 36 and/or 38, when the layer(s), such as layer(s) 36 and/or 38, is in a flat, unfolded configuration or when the layer(s), such as layer(s) 36 and/or 38, has a folded configuration. In an embodiment, a slit 96 can be a continuous or intermittent cut. In an embodiment, a slit 96 can be a line of weakness.

In an embodiment, a slit 96 can be incorporated into a layer(s), such as layer(s) 36 and/or 38, in any location of the layer(s), such as layer(s) 36 and/or 38, as deemed suitable. For example, a slit 96 can be incorporated into a layer(s), such as layer(s) 36 and/or 38, between the transverse edges of the layer(s), such as layer(s) 36 and/or 38, in association with a transverse edge of the layer(s), such as layer(s) 36 and/or 38, and combinations thereof.

In an embodiment, a slit 96 can be incorporated into at least one layer(s), such as layer(s) 36 and/or 38, and can be located in any desired location between the transverse edges of the layer(s), such as layer(s) 36 and/or 38. In such an embodiment, the slit 96 need not be associated with transverse edges of the layer(s), such as layer(s) 36 and/or 38. In such an embodiment, the slit 96 can be linear, arcuate, any other shape as desired, or combination thereof and can have any length 98 as desired. In such an embodiment, more than one slit 96 can be incorporated into the at least one layer(s), such as layer(s) 36 and/or 38, and each slit 96 can be separated from any other slit 96 by any distance as deemed suitable. In such an embodiment, the slit 96 can create a contact element 88 that can be at least partially bounded by a free edge 94 and at least partially bounded by a base 92.

Figure 12:
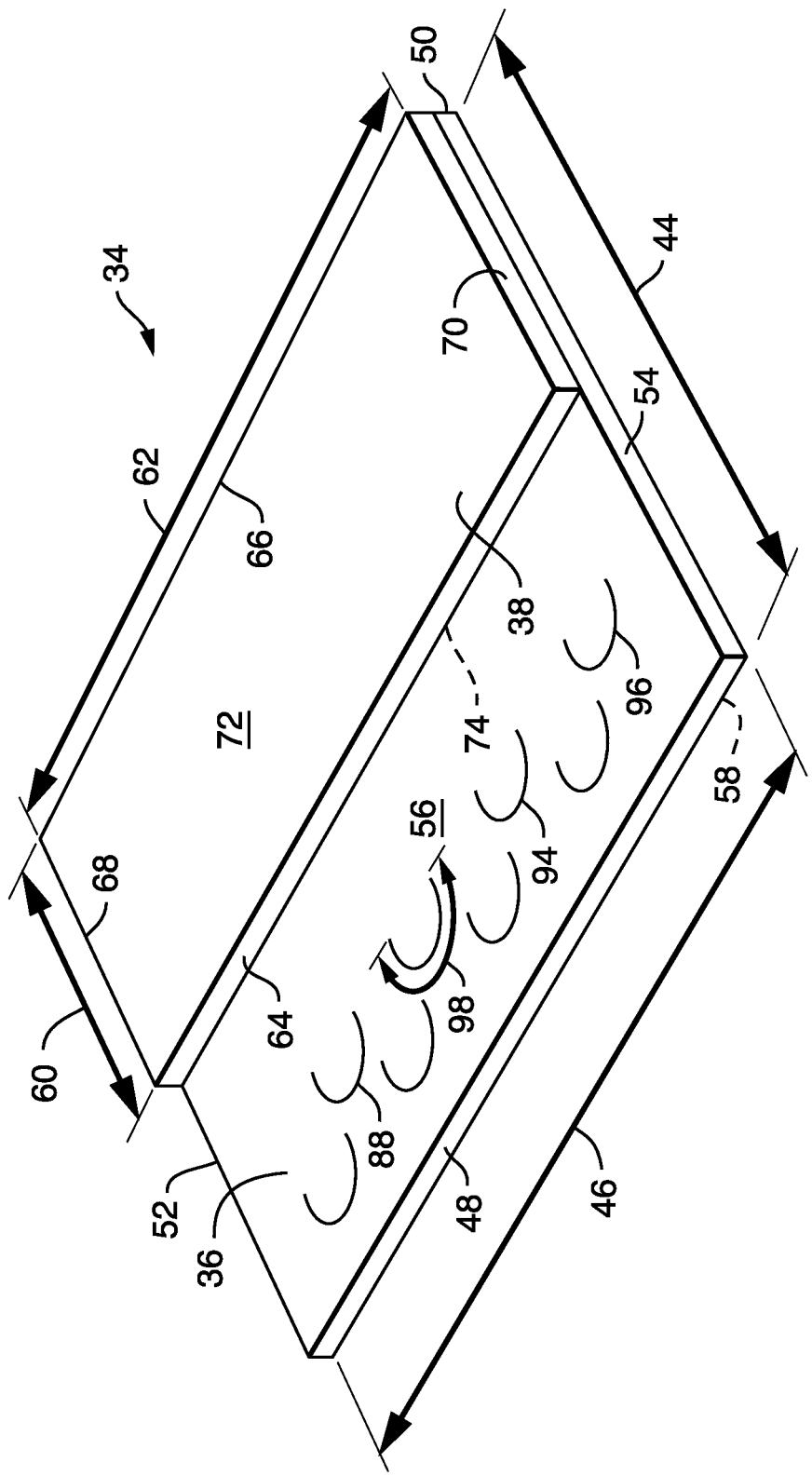
FIG. 12 is a perspective view of an embodiment of an absorbent structure with at least one contact element.

FIG. 12 provides a non-limiting example of an absorbent structure 34 which can have two layers, 36 and 38. The first layer 36 of the absorbent structure 34 can have a first length 44 which can be greater than the second length 60 of the second layer 38. The first width 46 of the first layer 36 can be substantially similar to the second width 62 of the second layer 38. The first layer 36 can have two transverse edges, 48 and 50, and the second layer 38 can have two transverse edges, 64 and 66. In the non-limiting example, transverse edge 66 of the second layer 38 can be substantially aligned with transverse edge 50 of the first layer 36. In the non-limiting illustration of FIG. 12, first layer 36 can have at least one slit 96 located between transverse edges 48 and 50 of layer 36. The slits 96 can extend from a first surface 56 of the first layer 36 through to a second surface 58 of the first layer 36. The slits 96 can be in any configuration as desired, such as, for example, an arcuate configuration. It should be realized that the slits 96 can have any length 98 as desired and can be spaced apart from each other any distance as desired. As described herein, transverse edge 48 can be located at the insertion end 18 or the withdrawal end 20 of a resultant tampon 10. In an embodiment, the contact elements 88 of the absorbent structure 34 illustrated in FIG. 12 can be located at the insertion end 18 or the withdrawal end 20 of a resultant tampon 10. In the non-limiting embodiment illustrated in FIG. 12, the contact elements 88 can be oriented towards the insertion end 18 or the withdrawal end 20 of a resultant tampon 10. In an embodiment, a slit 96 can also be incorporated into second layer 38.

In an embodiment, a slit 96 can be associated with a transverse edge of a layer, such as, for example, transverse edge 48 of layer 36, and can extend from the transverse edge 48 in a direction towards the interior region of the layer, such as, for example, the interior region of layer 36. In such an embodiment, the slit 96 can extend from the transverse edge 48 of layer 36 in a direction towards the opposite transverse edge, edge 50, of layer 36. As described herein, in an embodiment, a slit 96 need not be associated with a transverse edge of a layer, such as transverse edge 48 of layer 36.

In an embodiment, such as, for example, an embodiment in which more than one slit 96 can be associated with a transverse edge of a layer, such as layer 36 or 38, a width 102 (illustrated in FIG. 13) can separate a slit 96 from the next successive slit 96. The width 102 can be any distance as deemed suitable. In an embodiment, the width 102 can range from about 1, 2, 3, 4, 5, 6 or 7 mm to about 8, 9, 10, 11, 12, 13, 14 or 15 mm. In an embodiment in which slits 96 are associated with a transverse edge of a layer, such as layer 36 or 38, as described herein, the width 102 can be the width of a contact element 88. Two successive slits 96 associated with a transverse edge can create a contact element 88.

FIG. 13-24 illustrate various embodiments of slits 96 incorporated into at least one layer, 36 and/or 38, of an absorbent structure 34 and associated with a transverse edge. As shown in the non-limiting examples of FIG. 13-24, the slits 96 can be incorporated into a layer(s), 36 and/or 38, such as, for example, by being cut through from a first surface to a second surface of at least one layer, such as layer 36 and/or 38. While particular embodiments are illustrated and described, it is to be understood that various changes and modifications can be made to the embodiments illustrated and described without departing from the spirit and scope of the disclosure.

Figure 13:
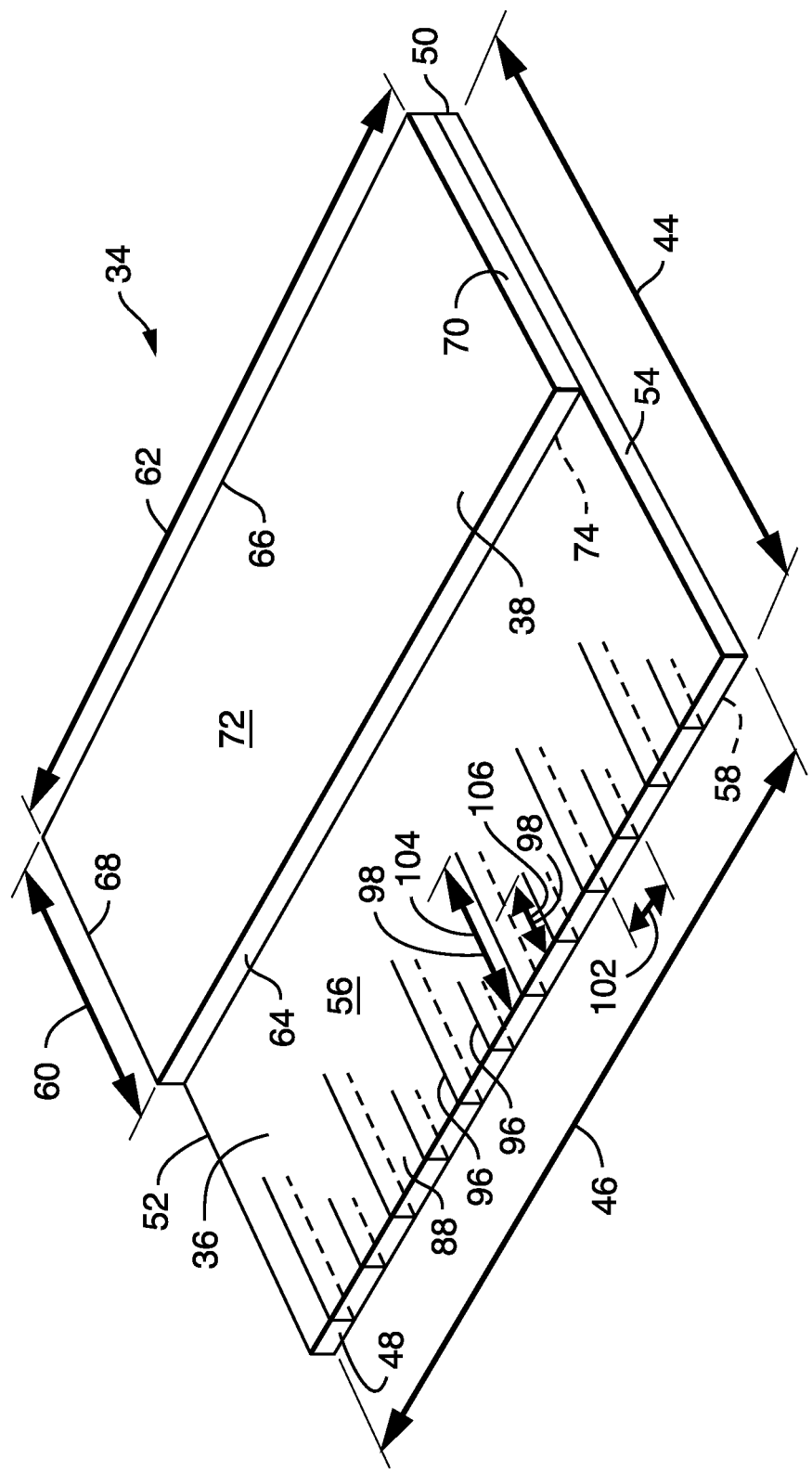
FIG. 13 is a perspective view of an embodiment of an absorbent structure with at least one contact element.

FIG. 13 provides a non-limiting example of an absorbent structure 34 which can have two layers, 36 and 38. The first layer 36 of the absorbent structure 34 can have a first length 44 which can be greater than the second length 60 of the second layer 38. The first width 46 of the first layer 36 can be substantially similar to the second width 62 of the second layer 38. The first layer 36 can have two transverse edges, 48 and 50, and the second layer 38 can have two transverse edges, 64 and 66. In the non-limiting example, transverse edge 66 of the second layer 38 can be substantially aligned with transverse edge 50 of the first layer 36. In the non-limiting illustration of FIG. 13, first layer 36 can have at least one slit 96 associated with transverse edge 48. The first layer 36 can have at least two successive slits 96 associated with transverse edge 48 and the two successive slits 96 can create a contact element 88. The slits 96 can extend from a first surface 56 of the first layer 36 through to a second surface 58 of the first layer 36. The slits 96 can extend from the transverse edge 48 in a direction away from the transverse edge 48 and towards an interior region of the first layer 36 of the absorbent structure 34 such that the slits 96 can extend in a direction toward the opposite transverse edge 50 of the first layer 36. It should be realized that the slits 96 can have any length 98 as desired as the slits 96 extend from transverse edge 48 in a direction towards the opposite transverse edge 50 of the first layer 36. As illustrated in FIG. 13 in a non-limiting embodiment, at least one of the slits 96 can have a first slit length 104 and at least one of the slits 96 can have a second slit length 106 wherein the first slit length 104 and the second slit length 106 are not the same. As illustrated in FIG. 13 in the non-limiting embodiment illustrated, the slits 96 may be incorporated into layer 36 in a pattern of alternating lengths. In an embodiment in which slits 96 having different lengths are incorporated into a layer, such as layer 36 and/or 38, the slits 96 having different lengths can be incorporated into the respective layer such that the different lengths of the slits 96 can be in a random sequence, in an alternating pattern, or in a repeating pattern. As illustrated in FIG. 13, the slits 96 do not necessarily extend the entire first length 44 of the first layer 36. While the second layer 38 is illustrated such that transverse edge 66 can be substantially aligned with transverse edge 50 of the first layer 36, it should be realized that transverse edge 66 of second layer 38 does not need to be substantially aligned with transverse edge 50 of the first layer 36. It should be realized that second layer 38 can be bonded to the first layer 36 at any position along the first length 44 of the first layer 36 as deemed suitable. It should be realized that transverse edge 64 of second layer 38 can also be positioned anywhere along the first length 44 of the first layer 36 as desired and the second length 60 of second layer 38 can be any dimension as desired. In an embodiment, layer 38 can at least partially or completely overlay the contact elements 88 incorporated into layer 36. As described herein, transverse edge 48 can be located at the insertion end 18 or the withdrawal end 20 of a resultant tampon 10. In an embodiment, the contact elements 88 of the absorbent structure 34 illustrated in FIG. 13 can be located at the insertion end 18 or the withdrawal end 20 of a resultant tampon 10. In the non-limiting embodiment illustrated in FIG. 13, the contact elements 88 can be oriented towards the insertion end 18 or the withdrawal end 20 of a resultant tampon 10. In an embodiment, a slit 96 can also be incorporated into second layer 38.

Figure 14:
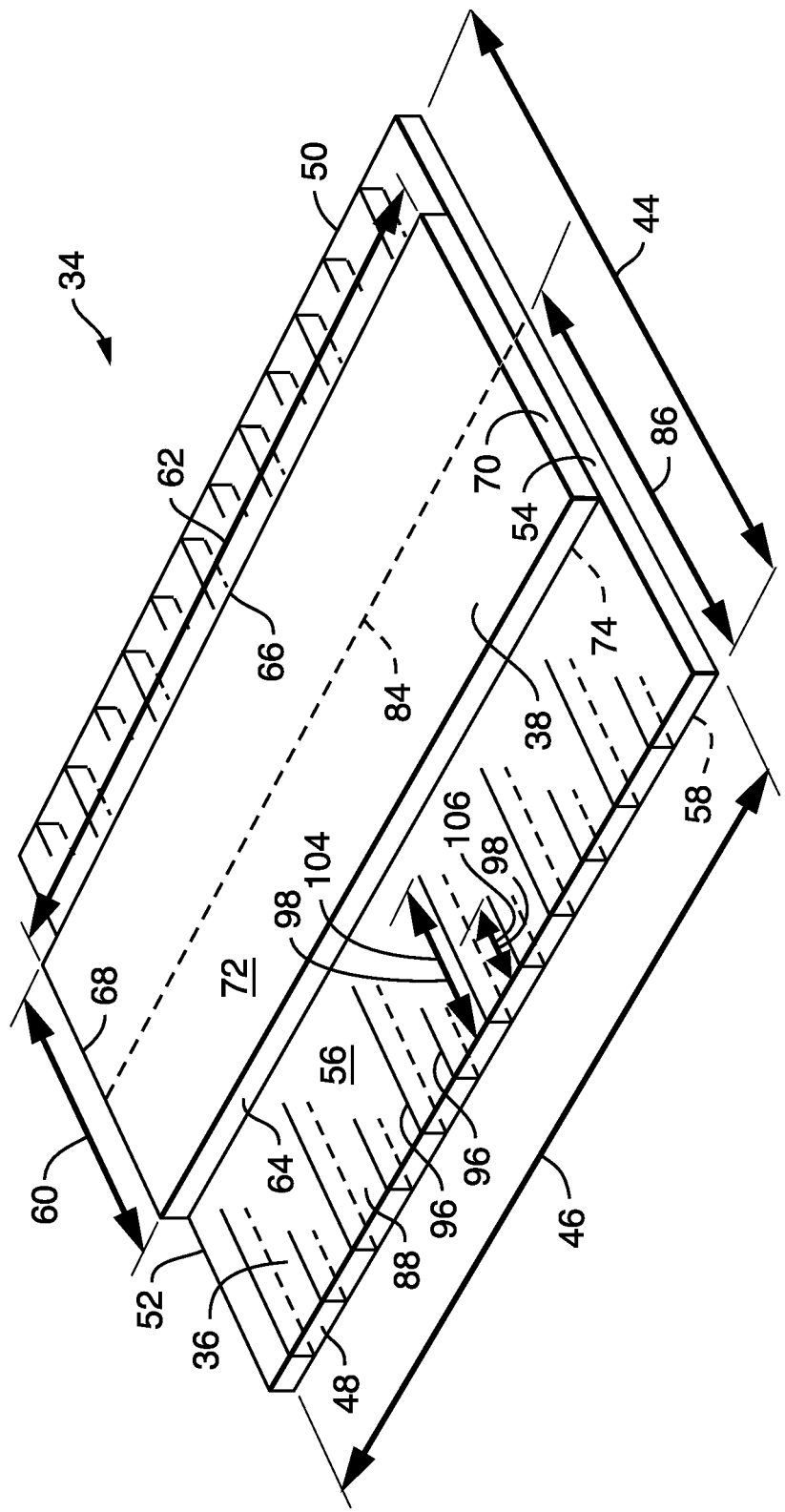
FIG. 14 is a perspective view of an embodiment of an absorbent structure with at least one contact element.

FIG. 14 provides an illustration of a non-limiting example of an embodiment of an absorbent structure 34 in which the first layer 36 can have a first length 44 greater than the second length 60 of the second layer 38. As illustrated in FIG. 14, the first width 46 of the first layer 36 can be substantially similar to the second width 62 of the second layer 38. In the non-limiting example illustrated in FIG. 14, the second layer 38 can be bonded to the first layer 36 in the central region of the first length 44 of the first layer 36. The central region of the first length 44 can be the area adjacent a center line 84 of the first length 44 of the first layer 36 of the absorbent structure 34. It is to be understood that the central region of the first length 44 does not need to be the exact center of the first layer 36, but can be located generally around the center line 84 of the first length 44. In an embodiment, the central region of the first layer 36 can be a position along the first length 44 which can be a distance 86 that can be about 0.35 to about 0.65 times the first length 44, as measured from either transverse edge, 48 or 50, of the first layer 36. In an embodiment, the second layer 38 does not have to be bonded to the first layer 36 in the central region of the first length 44, but rather could be bonded to the first layer 36 in an area adjacent to one of the transverse edges, 48 or 50, or at any other position along the first length 44 of the first layer 36 as deemed suitable. In the non-limiting illustration of FIG. 14, the first layer 36 can have at least one slit 96 associated with each of the transverse edges, 48 and 50, of first layer 36. The first layer 36 can have at least two successive slits 96 associated with transverse edges 48 and 50, respectively, and the two successive slits 96 associated with a transverse edge can create a contact element 88. The slits 96 can extend from a first surface 56 of the first layer 36 through to a second surface 58 of the first layer 36. The slits 96 can extend from the transverse edge, 48 or 50, respectively, in a direction towards an interior region of the first layer 36 of the absorbent structure 34 such that the slits 96 can extend from the associated transverse edge, 48 or 50, and in a direction toward the opposite transverse edge, 48 or 50, respectively, of the first layer 36. It should be realized that the slits 96 can have any length 98 as desired as the slits 96 extend from a transverse edge, 48 or 50, in a direction towards the opposite transverse edge, 48 or 50, of the first layer 36. As illustrated in FIG. 14 in a non-limiting embodiment, at least one of the slits 96 can have a first slit length 104 and at least one of the slits 96 can have a second slit length 106 wherein the first slit length 104 and the second slit length 106 are not the same. As illustrated in FIG. 14 in a non-limiting embodiment, the slits 96 may be incorporated into layer 36 in a pattern of alternating lengths. In an embodiment in which slits 96 having different lengths are incorporated into a layer, such as layer 36 and/or 38, the slits 96 having different lengths can be incorporated into the respective layer such that the different lengths of the slits 96 can be in a random sequence, in an alternating pattern, or in a repeating pattern. As illustrated in FIG. 14, the slits 96 do not necessarily extend the entire first length 44 of the first layer 36. It should be realized that transverse edges, 64 and 66, of second layer 38 can be positioned anywhere along the first length 44 of the first layer 36 as desired and the second length 60 of second layer 38 can be any dimension as desired. In an embodiment, layer 38 can at least partially or completely overlay the contact elements 88 incorporated into layer 36. As described herein, the transverse edges, 48 and 50, can be located at the insertion end 18 and the withdrawal end 20 of a resultant tampon 10. Thus, in an embodiment, the contact elements 88 of the absorbent structure 34 illustrated in FIG. 14 can be located at the insertion end 18 and the withdrawal end 20 of a resultant tampon 10. In the non-limiting embodiment illustrated in FIG. 14, the contact elements 88 can be oriented towards the insertion end 18 and the withdrawal end 20 of a resultant tampon 10. In an embodiment, a slit 96 can also be incorporated into second layer 38.

Figure 15:
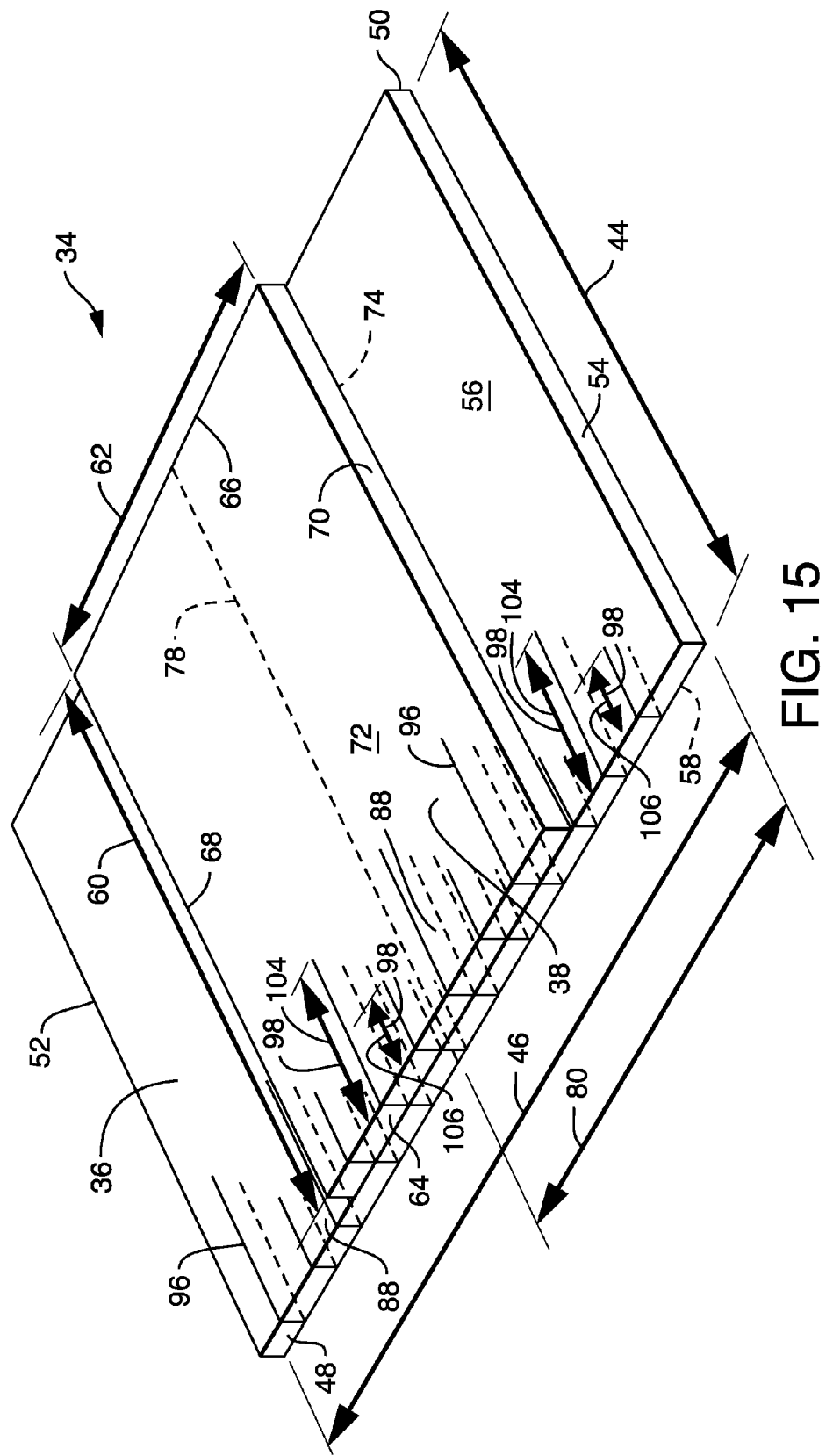
FIG. 15 is a perspective view of an embodiment of an absorbent structure with at least one contact element.

FIG. 15 provides an illustration of a non-limiting example of an embodiment of an absorbent structure 34 in which the first layer 36 can have a first width 46 greater than the second width 62 of the second layer 38. As illustrated in FIG. 15, the first length 44 of the first layer 36 can be substantially similar to the second length 60 of the second layer 38. In the non-limiting example illustrated in FIG. 15, the second layer 38 can be bonded to the central region of the first width 46 of the first layer 36. The central region of the first width 46 can be the area adjacent a center line 78 of the first width 46 of the first layer 36 of the absorbent structure 34. It is to be understood that the central region of the first width 46 does not need to be the exact center of the first layer 36, but can be located generally around the center line 78 of the first width 46. In an embodiment, the central region of the first width 46 of the first layer 36 can be a position along the first width 46 which can be a distance 80 that can be about 0.35 to about 0.65 times the first width 46, as measured from either longitudinal edge, 52 or 54, of the first layer 36. In an embodiment, the second layer 38 does not have to be bonded to the first layer 36 in the central region of the first width 46, but rather could be bonded to the first layer 36 in an area adjacent to one of the longitudinal edges, 52 or 54, or at any other position along the first width 46 of the first layer 36 as deemed suitable. In the non-limiting embodiment of FIG. 15, first layer 36 can have at least one slit 96 associated with transverse edge 48 and second layer 38 can have at least one slit 96 associated with transverse edge 64. Each layer, 36 and 38, can have at least two successive slits 96 associated with their respective transverse edges, 48 and 64, and the two successive slits 96 can create a contact element 88 in each layer, 36 and 38. With regards to the at least one slit 96 associated with the transverse edge 48 of the first layer 36, the slit 96 can extend from a first surface 56 of the first layer 36 through to a second surface 58 of the first layer 36. The slit 96 associated with transverse edge 48 can extend from the transverse edge 48 in a direction towards an interior region of the first layer 36 of the absorbent structure 34 such that the slit 96 can extend in a direction towards the opposite transverse edge 50 of the first layer 36. With regards to the at least one slit 96 associated with the transverse edge 64 of the second layer 38, the slit 96 can extend from a first surface 72 through to a second surface 74 of the second layer 38. The slit 96 associated with transverse edge 64 can extend from the transverse edge 64 in a direction towards an interior region of the second layer 38 of the absorbent structure 34 such that the slit 96 can extend from the transverse edge 64 in a direction towards the opposite transverse edge 66 of the second layer 38. While the slits 96 of the first layer 36 and the slits 96 of the second layer 38 are illustrated in a manner in which the slits 96 of the second layer 38 can be positioned to substantially align with the slits 96 of the first layer 36, it should be realized that the slits 96 of the second layer 38 can be offset from the slits 96 of the first layer 36. An offset of the slits 96 of the second layer 38 from the slits 96 of the first layer 36 can be in any amount as deemed suitable. It should be realized that the slits 96 of each of the layers, 36 and 38, can have any length 98 as desired as the slits 96 extend from a transverse edge, 48 or 64, in a direction towards the opposite transverse edge, 50 or 66, of the first layer 36 or second layer 38, respectively. As illustrated in FIG. 15 in a non-limiting embodiment, at least one of the slits 96 of layer 36 and/or 38 can have a first slit length 104 and at least one of the slits 96 of the same layer, 36 and/or 38, can have a second slit length 106 wherein the first slit length 104 and the second slit length 106 are not the same. As illustrated in FIG. 15 in a non-limiting embodiment, the slits 96 may be incorporated into layer 36 and layer 38 in a pattern of alternating lengths. In an embodiment in which slits 96 having different lengths are incorporated into a layer, such as layer 36 and/or 38, the slits 96 having different lengths can be incorporated into the respective layer such that the different lengths of the slits 96 can be in a random sequence, in an alternating pattern, or in a repeating pattern. As illustrated in FIG. 15, the slits 96 do not necessarily extend the entire length, 44 or 60, of the first layer 36 or the second layer 38, respectively. As described herein, the transverse edges, 48, 50, 64, and 66, can be located at the insertion end 18 or the withdrawal end 20 of a resultant tampon 10. Thus, in an embodiment, the contact elements 88 of the absorbent structure 34 illustrated in FIG. 15 can be located at the insertion end 18 or the withdrawal end 20 of a resultant tampon 10. In the non-limiting embodiment illustrated in FIG. 15, the contact elements 88 of layers 36 and 38 can be oriented towards the insertion end 18 or the withdrawal end 20 of a resultant tampon 10. In an embodiment, at least one of the layers, 36 and/or 38, can also have at least one slit 96 associated with the opposite transverse edge, 50 and/or 66, respectively. It should be realized that in the non-limiting embodiment illustrated in FIG. 15, the contact elements 88 of the first layer 36 and the contact elements 88 of the second layer 38 need not be bonded to each other. Thus, it should be realized that the two layers, 36 and 38, do not need to be bonded to each other in any region wherein a contact element 88 is present.

Figure 16:
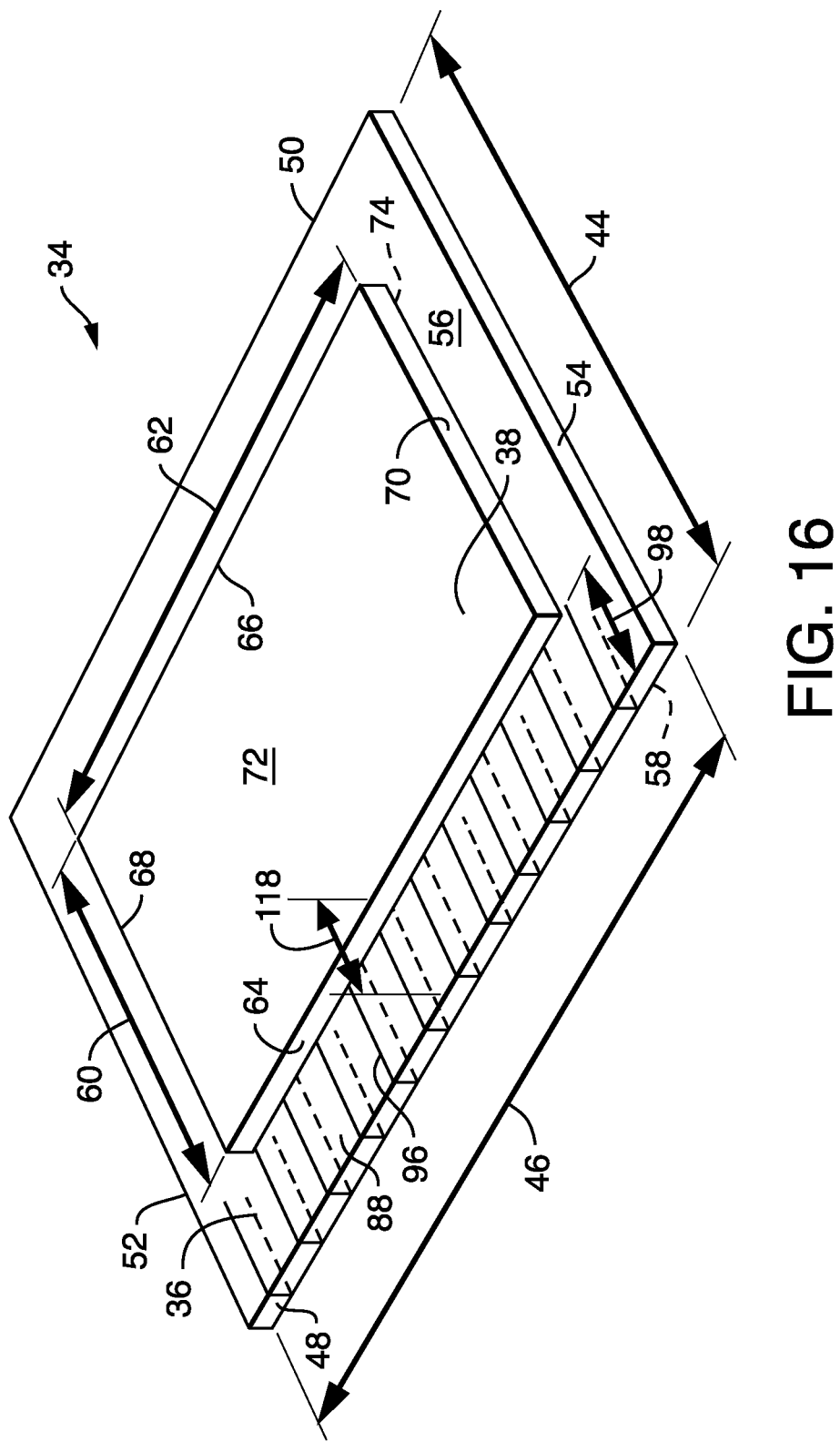
FIG. 16 is a perspective view of an embodiment of an absorbent structure with at least one contact element.

FIG. 16 provides an illustration of a non-limiting example of an embodiment of an absorbent structure 34 in which the first layer 36 can have a first length 44 and a first width 46 that can each be greater than the second length 60 and the second width 62 of the second layer 38. In the non-limiting illustration of FIG. 16, first layer 36 can have at least one slit 96 associated with a transverse edge such as transverse edge 48. The first layer 36 can have at least two successive slits 96 associated with transverse edge 48 and the two successive slits 96 can create a contact element 88. The slits 96 can extend from a first surface 56 of the first layer 36 through to a second surface 58 of the first layer 36. The slits 96 can extend from the transverse edge 48 in a direction away from the transverse edge 48 and towards an interior region of the first layer 36 of the absorbent structure 34 such that the slits 96 can extend in a direction toward the opposite transverse edge 50 of the first layer 36. It should be realized that the slits 96 can have any length 98 as desired as the slits 96 extend from transverse edge 48 in a direction towards the opposite transverse edge 50 of the first layer 36. As illustrated in FIG. 16 in a non-limiting embodiment, each slit 96 can have a length 98 substantially similar to the length 98 of each other slit 96 present. In an embodiment, the slits 96 can have varying lengths 98. As illustrated in FIG. 16, the slits 96 do not necessarily extend the entire first length 44 of the first layer 36. In an embodiment, the slits 96 can extend a length 98 that is substantially similar to, less than or greater than a distance 118 between transverse edge 48 and transverse edge 64. It should be realized that second layer 38 can be bonded to the first layer 36 at any position along the first length 44 and/or first width 46 of the first layer 36 as deemed suitable and can have any size dimension as deemed suitable. It should be realized that the two layers, 36 and 38, do not need to be bonded to each other in any region wherein a contact element 88 is present. As described herein, the transverse edge 48 can be located at the insertion end 18 or the withdrawal end 20 of a resultant tampon 10. Thus, in an embodiment, the contact elements 88 of the absorbent structure 34 illustrated in FIG. 16 can be located at the insertion end 18 or the withdrawal end 20 of a resultant tampon 10. In the non-limiting embodiment illustrated in FIG. 16, the contact elements 88 can be oriented towards the insertion end 18 or the withdrawal end 20 of a resultant tampon 10. In embodiment, at least one slit 96 can also be incorporated into second layer 38.

Figure 17:
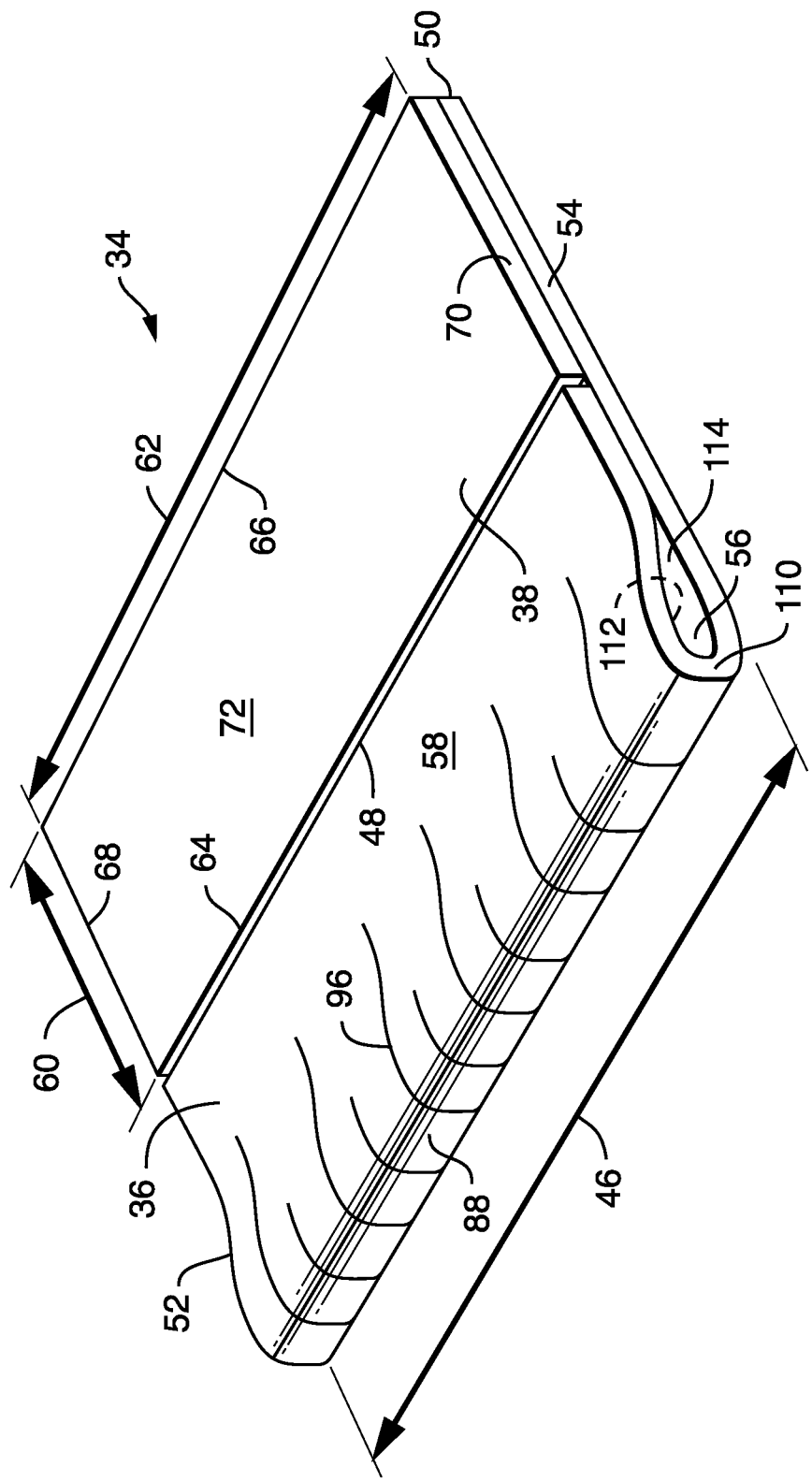
FIG. 17 is a perspective view of an embodiment of an absorbent structure with at least one contact element.

FIG. 17 provides an illustration of a non-limiting example of an embodiment of an absorbent structure 34 which can have two layers, 36 and 38. As illustrated, first layer 36 can have a first width 46 that can be substantially similar to a second width 62 of the second layer 38. As illustrated, first layer 36 can have at least one fold 110 incorporated therein. In such an embodiment in which a fold 110 is present, the first layer 36 can be bent upon itself such that a first portion of at least one of the surfaces, 56 or 58, can be in communication with a second portion of the same surface, 56 or 58. As a non-limiting example, as illustrated in FIG. 17, the first layer 36 can contain a single fold 110 bringing a first portion 112 of the first surface 56 into communication with a second portion 114 of the first surface 56. In the non-limiting embodiment illustrated in FIG. 17, the fold 110 can bring transverse edge 48 of first layer 36 into communication with transverse edge 64 of the second layer 38. It should be realized that layer 36 can have a first length 44 greater than a second length 60 of layer 38 and fold 110 can occur at any desired location along the first length 44 of layer 36. In an embodiment, a fold 110 can bring transverse edge 48 of layer 36 into communication with transverse edge 64 of layer 38, into communication with a portion of second layer 38 located between transverse edges 64 and 66, into communication with transverse edge 66 of second layer 38, into a configuration wherein transverse edge 48 can extend beyond transverse edge 66, or to a location of first layer 36 such that transverse edge 48 is not in communication with the second layer 38. As illustrated, first layer 36 can have at least one slit 96 which can be cut through from a second surface 58, through the first and second portions, 112 and 114, of the first surface 56, and to the opposite second surface 58 of the first layer 36. The first layer 36 can have at least two successive slits 96 and the two successive slits 96 can create a contact element 88. As illustrated, the slit(s) 96 can be associated with the fold 110 of the first layer 36. The slit(s) 96 can extend from the fold 110 of the first layer 36 in a direction away from the fold 110 and towards the interior region of the absorbent structure 34 such that the slits 96 can extend from the fold 110 of first layer 36 in a direction towards transverse edge 50 of layer 36. The slit(s) 96 can be incorporated into the first layer 36 prior to or after fold 110 has been incorporated into layer 36. It should be realized that, in an embodiment, at least one slit 96 can be incorporated into second layer 38. In an embodiment, at least one of the layers, 36 and/or 38, can have at least one slit 96 associated with the transverse edges, 48, 50, 64 and/or 66, respectively. As described herein, the fold 110 can be located at the insertion end 18 or the withdrawal end 20 of a resultant tampon 10. Thus, in an embodiment, the contact elements 88 of the absorbent structure 34 illustrated in FIG. 17 can be located at the insertion end 18 or the withdrawal end 20 of a resultant tampon 10. In the non-limiting embodiment illustrated in FIG. 17, the contact elements 88 can be oriented towards the insertion end 18 or the withdrawal end 20 of a resultant tampon 10.

Figure 18:
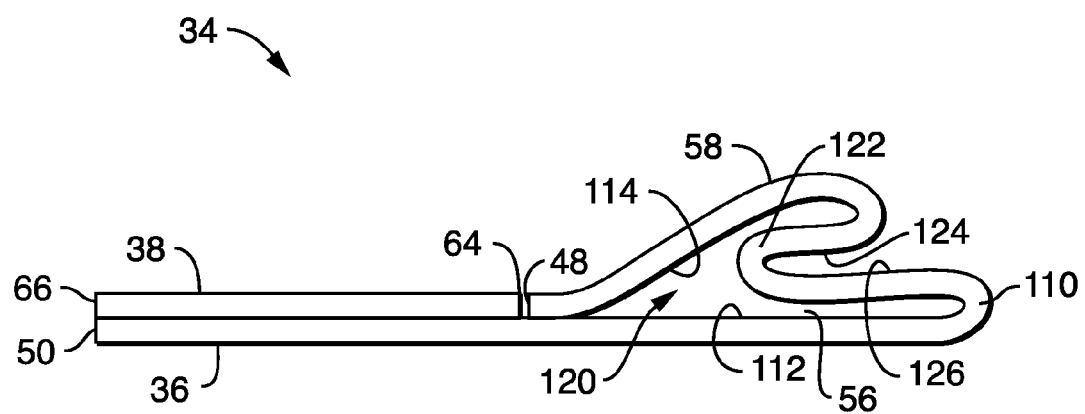
FIG. 18 is a side view of an embodiment of an absorbent structure.

FIG. 18 provides an illustration of a non-limiting example of an embodiment of an absorbent structure 34 which can have two layers 36 and 38. As illustrated, the first layer 36 can have two transverse edges, 48 and 50, and the second layer 38 can have two transverse edges, 64 and 66. In an embodiment, the first layer 36 can have more than one fold, such as folds 110 and 122, incorporated therein. In such an embodiment, the first fold 110 can bring transverse edge 48 of first layer 36 into communication with transverse edge 64 of the second layer 38. In an embodiment, fold 110 can bring transverse edge 48 of layer 36 into communication with transverse edge 64 of layer 38, into communication with a portion of layer 38 located between transverse edges 64 and 66, into communication with transverse edge 66 of layer 38, into a configuration wherein transverse edge 48 can extend beyond transverse edge 66, or to a location of layer 36 such that transverse edge 48 is not in communication with layer 38. In such an embodiment, a first portion 112 of first surface 56 of the first layer 36 can be brought into a face-to-face relationship with a second portion 114 of first surface 56 of the first layer 36. In an embodiment, the fold 110 can be utilized to bring the two portions, 112 and 114, into a facing relationship and, in some embodiments, a space 120 can exist between the two portions, 112 and 114, while they are in a facing relationship. In an embodiment, such as illustrated in the non-limiting embodiment of FIG. 18, a second fold 122 can be incorporated into layer 36. In the non-limiting illustration, the second fold 122 can be incorporated into layer 36 at any location of the first layer 36 such as, for example, at a location between the transverse edge 48 and the first fold 110. The second fold 122 can be configured such that the second fold 122 can position a portion of the first layer 36 into the space 120 created by the first fold 110. The second fold 122 can bring a first portion 124 of the second surface 58 into a facing relationship with a second portion 126 of the second surface 58 of the first layer 36. The first layer 36 can have at least one slit 96 incorporated therein (not shown). The at least one slit 96 can be incorporated into layer 36 before or after the incorporation of either of the folds, 110 and/or 122. The at least one slit 96 can be associated with either or both of the folds 110 and/or 122. In an embodiment in which slits 96 are associated with only one of the folds, 110 or 122, the contact element(s) 88 formed by the incorporation of the slits 96 can be in an at least partially overlapping relationship with a portion of the folded first layer 36 not containing any slits 96 or contact elements 88. In an embodiment in which slits 96 are associated with each of the folds, 110 and 122, the contact element(s) 88 formed by the incorporation of the slits 96 can be in an at least partially overlapping relationship. As described herein, the folds 110 and 122 can be located at the insertion end 18 or the withdrawal end 20 of a resultant tampon 10. Thus, in an embodiment, the contact elements 88 of the absorbent structure 34 illustrated in FIG. 18 can be located at the insertion end 18 or the withdrawal end 20 of a resultant tampon 10. In the non-limiting embodiment illustrated in FIG. 18, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 19:
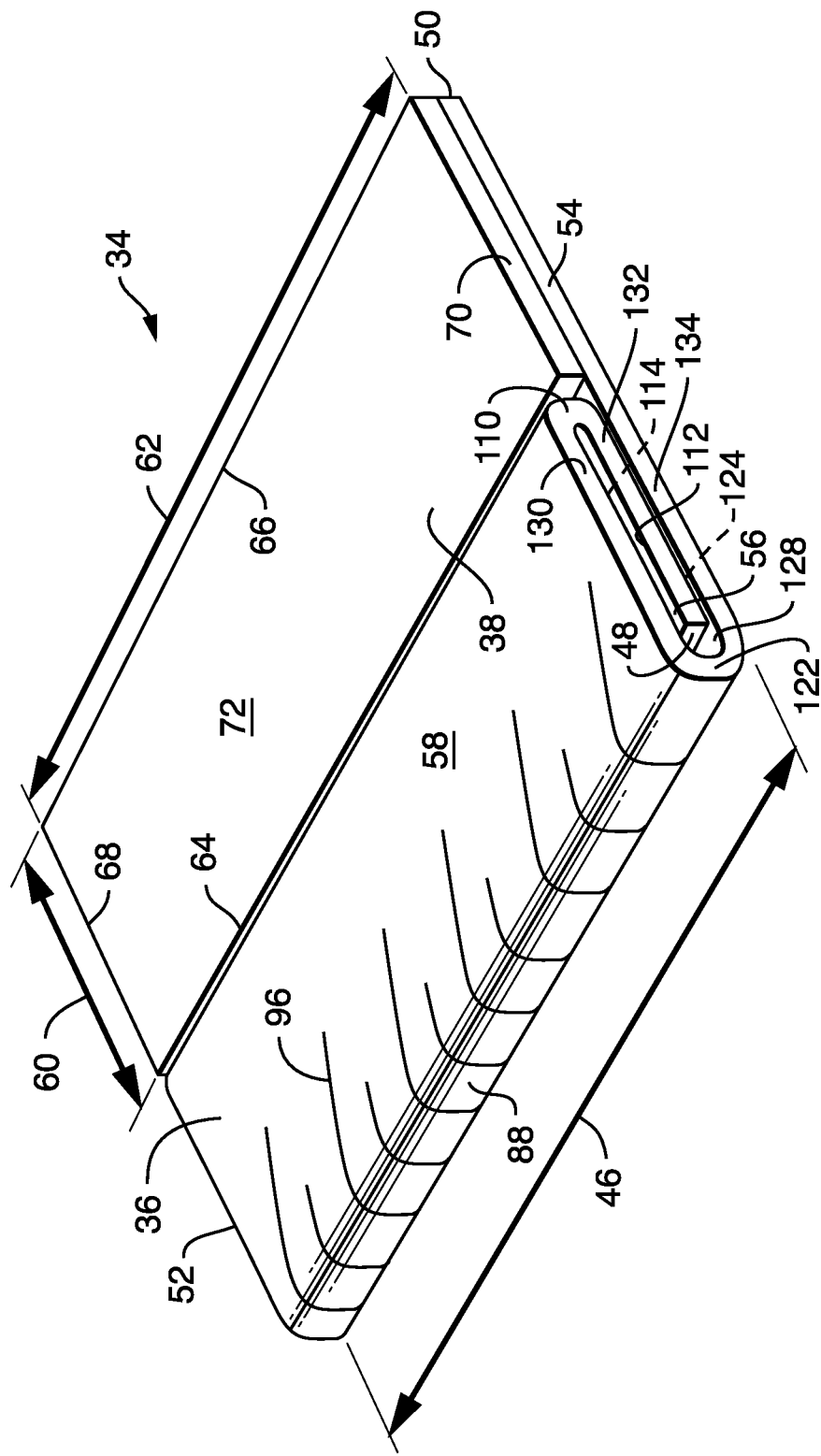
FIG. 19 is a perspective view of an embodiment of an absorbent structure with at least one contact element.

FIG. 19 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, first layer 36 can have at least two folds, 110 and 122, incorporated therein. In such an embodiment in which two folds, 110 and 122, are present, the layer 36 can be bent upon itself such that a first portion of one surface, 56 or 58, of the layer 36 can be in a facing relationship with a second portion of the same surface, 56 or 58, and a third portion of one surface, 56 or 58, of the layer 36 can be in a facing relationship with a first portion of the other surface, 56 or 58. As a non-limiting example, as illustrated in FIG. 19, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a third portion 128 of the first surface 56 into a facing relationship with a first portion 124 of the second surface 58 of layer 36. The second fold 122 can be created by bending layer 36 at a location along the first length 44 of layer 36 between the transverse edge 48 of layer 36 and the transverse edge 64 of layer 38. As illustrated in FIG. 19, following the folding of layer 36 with fold 122, transverse edge 48 need not be in communication with second layer 38 of the absorbent structure 34. In an embodiment, each fold 110 and 122 can result in layer 36 having multiple layers, such as layers 130, 132, and 134. In an embodiment, layer 36 can have at least one slit 96 extending through the layers, 130, 132 and 134, of the layer 36. The first layer 36 can have at least two successive slits 96 and the two successive slits 96 can create a contact element 88. As illustrated, the at least one slit 96 can extend from the second surface 58 of layer 36, through the first and second portions, 112 and 114, of the first surface 56 of layer 36, through the first portion 124 of the second surface 58 of layer 36 and the third portion 128 of the first surface 56 of layer 36, and to the opposite second surface 58 of the first layer 36. As illustrated, the slit(s) 96 can be associated with the second fold 122 of the first layer 36. The slit(s) 96 can extend from the fold 122 of the first layer 36 in a direction away from the fold 122 and towards the interior region of the absorbent structure 34 such that the slits 96 can extend from the fold 122 of first layer 36 in a direction towards transverse edge 50 of layer 36. The at least one slit 96 can be incorporated into layer 36 prior to or after layer 36 has been folded. As described herein, the fold 122 can be located at the insertion end 18 or the withdrawal end 20 of a resultant tampon 10. Thus, in an embodiment, the contact elements 88 of the absorbent structure 34 illustrated in FIG. 19 can be located at the insertion end 18 or the withdrawal end 20 of a resultant tampon 10. In the non-limiting embodiment illustrated in FIG. 19, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 20:
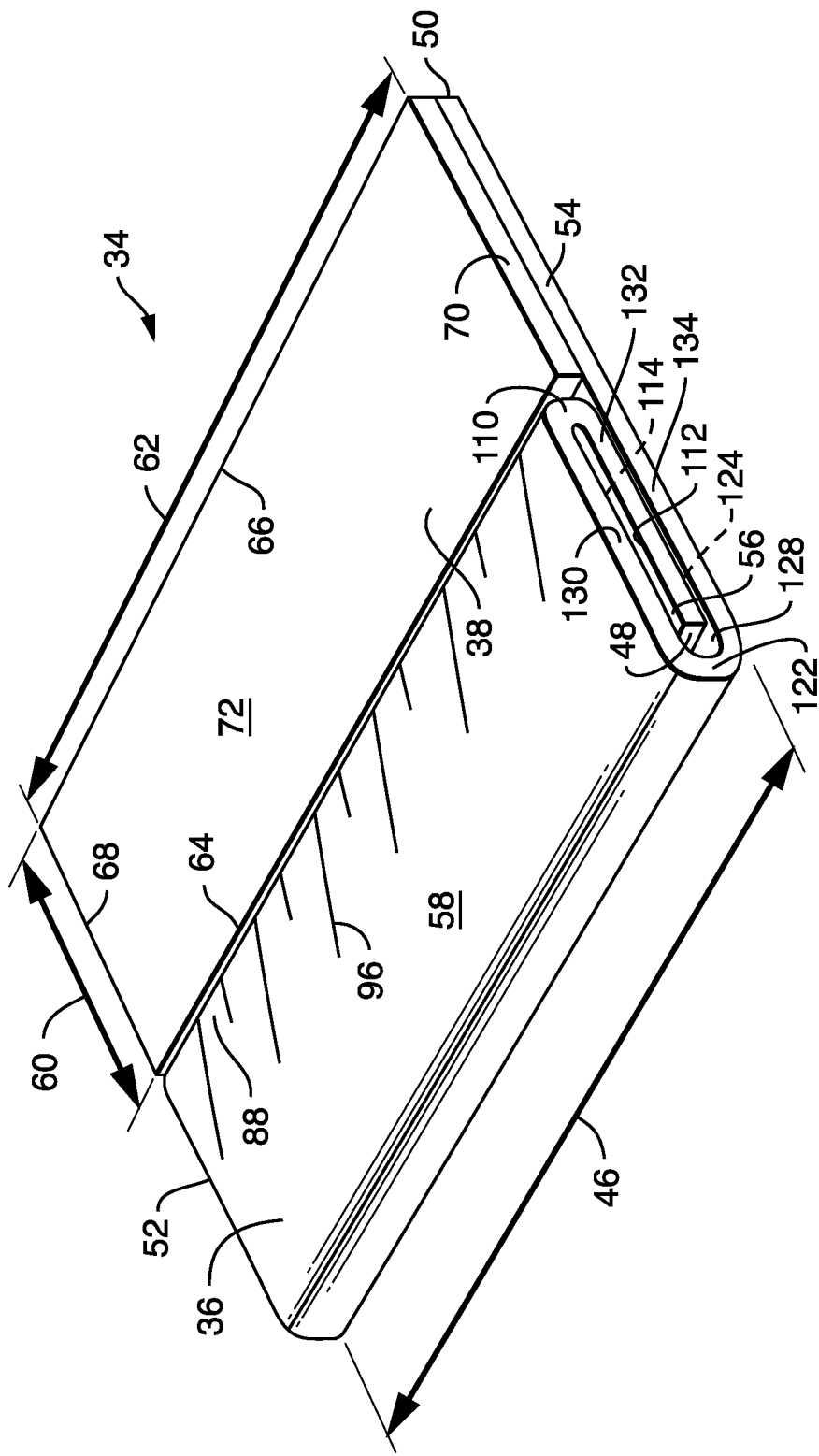
FIG. 20 is a perspective view of an embodiment of an absorbent structure with at least one contact element.

FIG. 20 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, first layer 36 can have at least two folds, 110 and 122, incorporated therein. In such an embodiment in which two folds, 110 and 122, are present, the layer 36 can be bent upon itself such that a first portion of one surface, 56 or 58, of the layer 36 can be in a facing relationship with a second portion of the same surface, 56 or 58, and a third portion of one surface, 56 or 58, of the layer 36 can be in a facing relationship with a first portion of the other surface, 56 or 58. As a non-limiting example, as illustrated in FIG. 20, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a third portion 128 of the first surface 56 into a facing relationship with a first portion 124 of the second surface 58 of layer 36. The second fold 122 can be created by bending layer 36 at a location along the first length 44 of layer 36 between the transverse edge 48 of layer 36 and the transverse edge 64 of layer 38. As illustrated in FIG. 20, following the folding of layer 36 with fold 122, transverse edge 48 need not be in communication with second layer 38 of the absorbent structure 34. In an embodiment, each fold 110 and 122 can result in layer 36 having multiple layers, such as layers 130, 132, and 134. In an embodiment, layer 36 can have at least one slit 96 extending through the layers, 130 and 132, of the layer 36. The first layer 36 can have at least two successive slits 96 extending through the layers, 130 and 132, and the two successive slits 96 can create a contact element 88. As illustrated, the at least one slit 96 can extend from the second surface 58 of layer 36 and through the first and second portions, 112 and 114, of the first surface 56 of layer 36 to the first portion 124 of the second surface 58 of layer 36. As illustrated, the slit(s) 96 can be associated with the first fold 110 of the first layer 36. The slit(s) 96 can extend from the fold 110 of the first layer 36 in a direction away from the fold 110 and towards the second fold 122 of the first layer 36. The at least one slit 96 can be incorporated into layer 36 prior to or after layer 36 has been folded with the first fold 110. As described herein, the fold 110 can be located at a location between the insertion end 18 and the withdrawal end 20 of a resultant tampon 10. Thus, in an embodiment, the contact elements 88 of the absorbent structure 34 illustrated in FIG. 20 can be located at a location between the insertion end 18 and the withdrawal end 20 of a resultant tampon 10. In the non-limiting embodiment illustrated in FIG. 20, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 21:
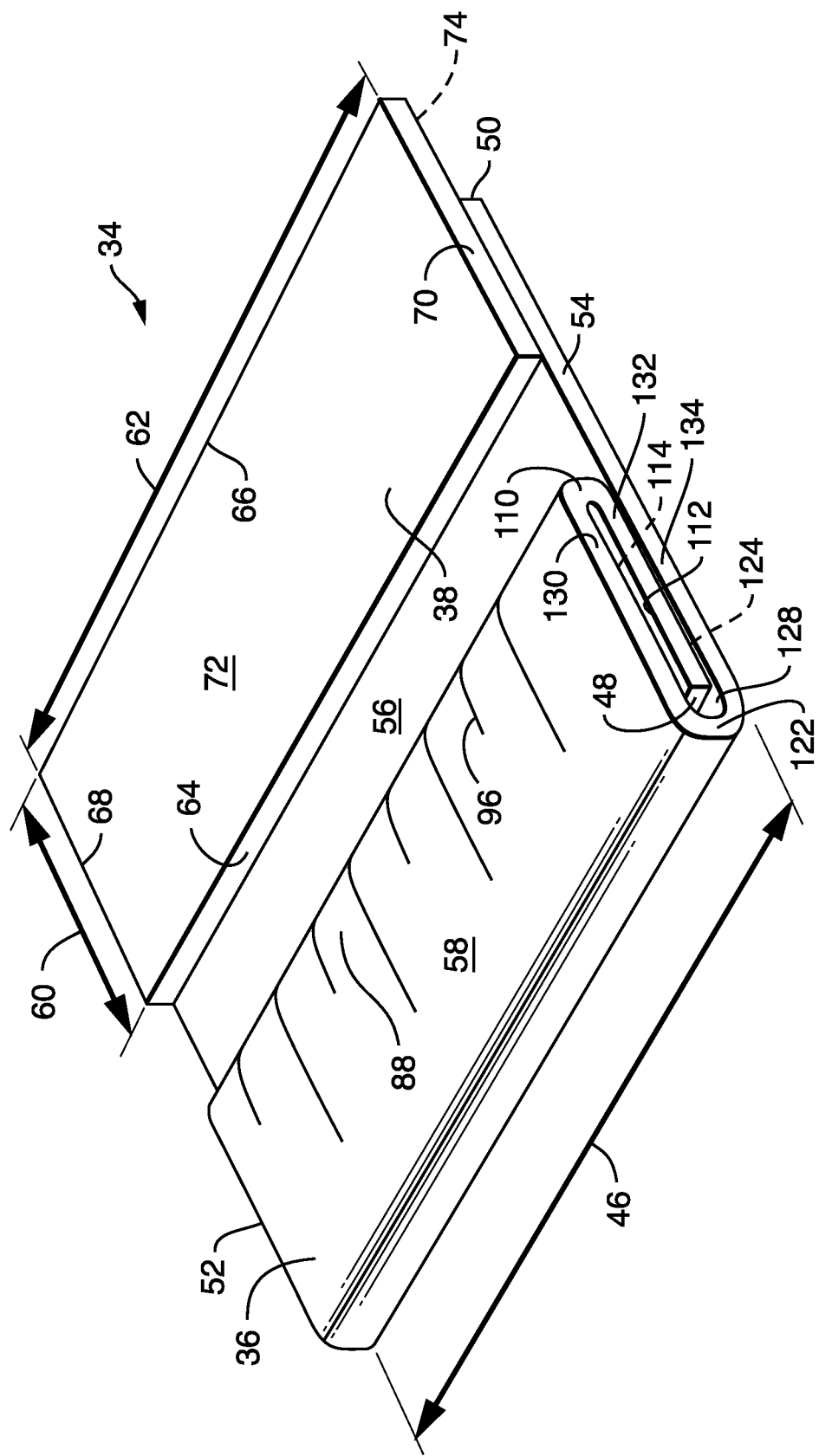
FIG. 21 is a perspective view of an embodiment of an absorbent structure with at least one contact element.

FIG. 21 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, less than 100% of surface 74 of second layer 38 can be in a face to face relationship with surface 56 of first layer 36. As illustrated, first layer 36 can have at least two folds, 110 and 122, incorporated therein. In such an embodiment in which two folds 110 and 122 are present, the layer 36 can be bent upon itself such that a first portion of one surface, 56 or 58, of the layer 36 can be in a facing relationship with a second portion of the same surface, 56 or 58, and a third portion of one surface, 56 or 58, of the layer 36 can be in a facing relationship with a first portion of the other surface, 56 or 58. As a non-limiting example, as illustrated in FIG. 21, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a third portion 128 of the first surface 56 into a facing relationship with a first portion 124 of the second surface 58 of layer 36. The second fold 122 can be created by bending layer 36 at a location along the first length 44 of layer 36 between the transverse edge 48 of layer 36 and the transverse edge 64 of layer 38. As illustrated in FIG. 21, following the folding of layer 36 with fold 122, transverse edge 48 need not be in communication with second layer 38 of the absorbent structure 34. In an embodiment, each fold 110 and 122 can result in layer 36 having multiple layers, such as layers 130, 132, and 134. In an embodiment, layer 36 can have at least one slit 96 extending through the layers, 130 and 132, of the layer 36. The first layer 36 can have at least two successive slits 96 extending through the layers, 130 and 132, and the two successive slits 96 can create a contact element 88. As illustrated, the at least one slit 96 can extend from the second surface 58 of layer 36 and through the first and second portions, 112 and 114, of the first surface 56 of layer 36 to the first portion 124 of the second surface 58 of layer 36. As illustrated, the slit(s) 96 can be associated with the first fold 110 of the first layer 36. The slit(s) 96 can extend from the fold 110 of the first layer 36 in a direction away from the fold 110 and towards the second fold 122 of the first layer 36. The at least one slit 96 can be incorporated into layer 36 prior to or after layer 36 has been folded with the first fold 110. As described herein, the fold 110 can be located at a location between the insertion end 18 and the withdrawal end 20 of a resultant tampon 10. Thus, in an embodiment, the contact elements 88 of the absorbent structure 34 illustrated in FIG. 21 can be located at a location between the insertion end 18 and the withdrawal end 20 of a resultant tampon 10. In the non-limiting embodiment illustrated in FIG. 21, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 22:
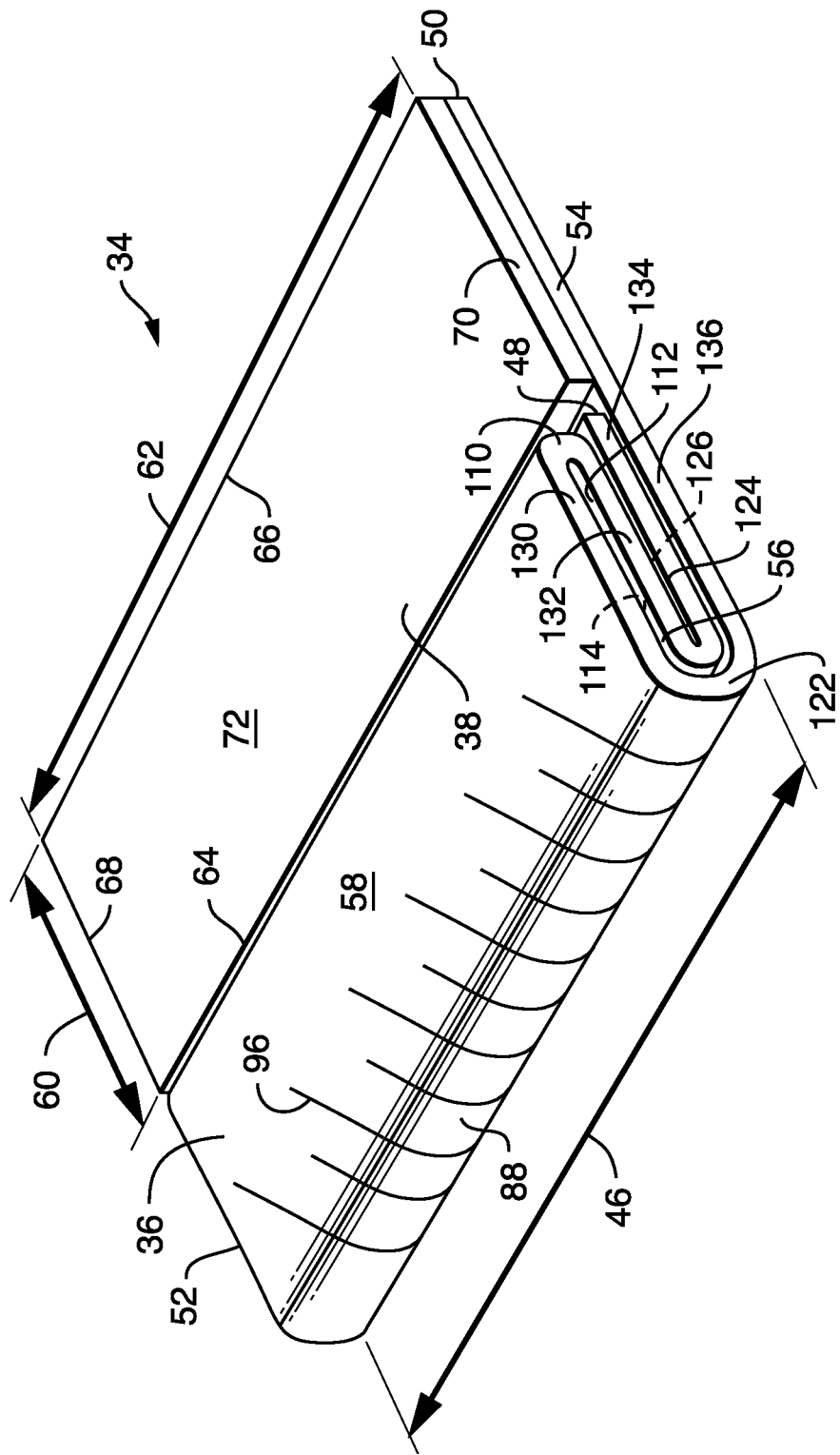
FIG. 22 is a perspective view of an embodiment of an absorbent structure with at least one contact element.

FIG. 22 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, first layer 36 can have at least two folds, 110 and 122, incorporated therein. In such an embodiment as illustrated in FIG. 22 in which two folds, 110 and 122, are present, the layer 36 can be bent upon itself such that a first portion of one surface, 56 or 58, of the layer 36 can be in a facing relationship with a second portion of the same surface, 56 or 58, and a first portion of the other surface, 56 or 58, of the layer 36 can be in a facing relationship with a second portion of the same surface, 56 or 58. As a non-limiting example, as illustrated in FIG. 22, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a first portion 124 of the second surface 58 into a facing relationship with a second portion 126 of the second surface 58 of layer 36. The second fold 122 can be created by bending layer 36 at a location along the first length 44 of layer 36 between the transverse edge 48 of layer 36 and the first fold 110 of layer 36. As illustrated in FIG. 22, transverse edge 48 of layer 36 can be in communication with transverse edge 64 of the second layer 38 of the absorbent structure 34. In an embodiment, each fold 110 and 122 can result in layer 36 having multiple layers, such as layers 130, 132, 134 and 136. In an embodiment, layer 36 can have at least one slit 96 extending through the layers, 130, 132, 134 and 136, of the layer 36. The first layer 36 can have at least two successive slits 96 extending through the layers, 130, 132, 134, and 136, and the two successive slits 96 can create a contact element 88. As illustrated, the at least one slit 96 can extend from the second surface 58 of layer 36, through the first and second portions, 112 and 114, of the first surface 56 of layer 36, through the first and second portions, 124 and 126, of the second surface 58 of layer 36, through opposite first and second portions, 112 and 114, of the first surface 56 of layer 36, and to the opposite second surface 58 of the first layer 36. As illustrated, the slit(s) 96 can be associated with the second fold 122 of the first layer 36. The slit(s) 96 can extend from the fold 122 of the first layer 36 in a direction away from the fold 122 and towards the interior region of the absorbent structure 34 such that the slits 96 can extend from the fold 122 of first layer 36 in a direction towards transverse edge 50 of layer 36. The at least one slit 96 can be incorporated into layer 36 prior to or after layer 36 has been folded. As described herein, the fold 122 can be located at the insertion end 18 or the withdrawal end 20 of a resultant tampon 10. Thus, in an embodiment, the contact elements 88 of the absorbent structure 34 illustrated in FIG. 22 can be located at the insertion end 18 or the withdrawal end 20 of a resultant tampon 10. In the non-limiting embodiment illustrated in FIG. 22, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 23:
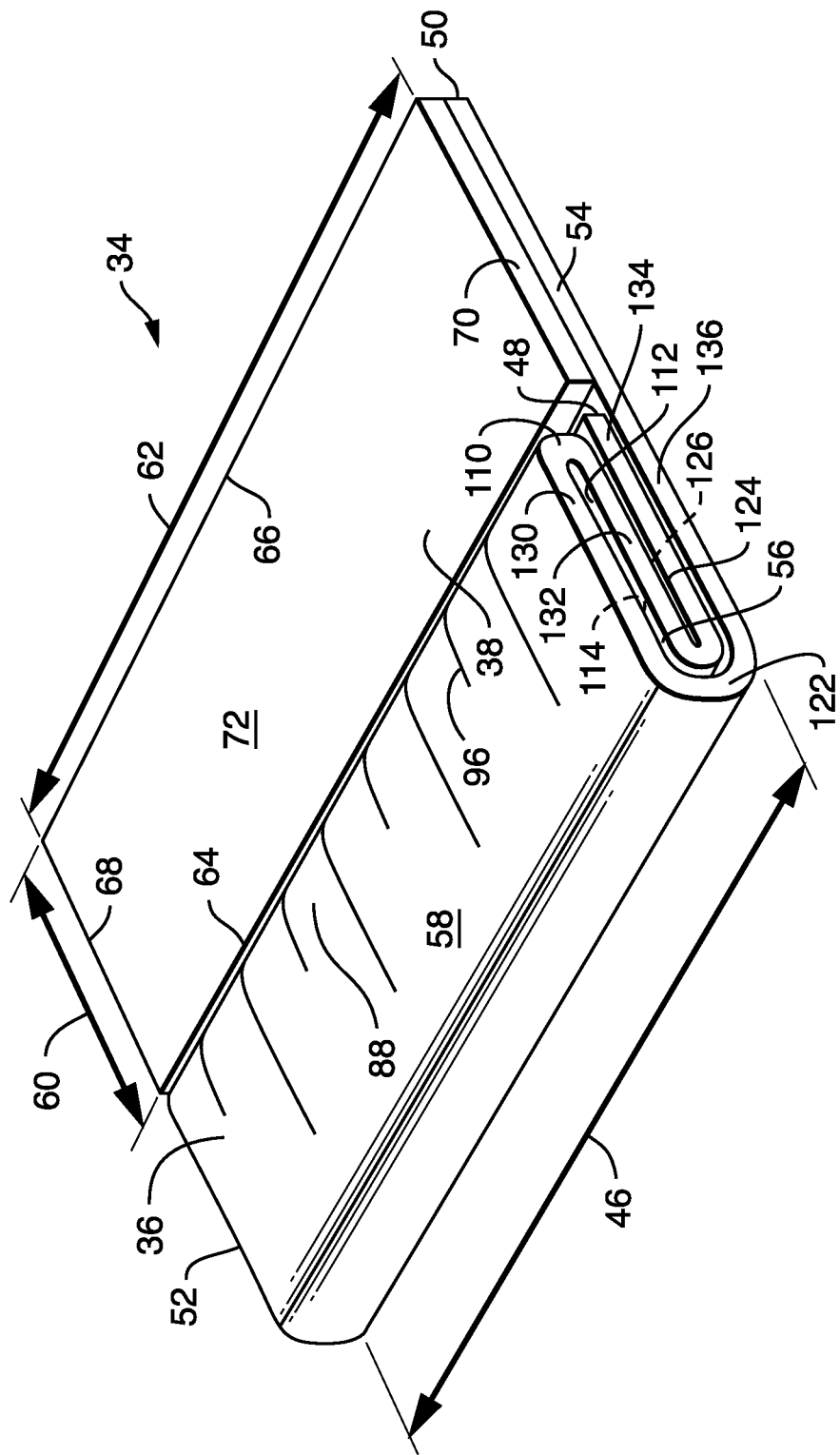
FIG. 23 is a perspective view of an embodiment of an absorbent structure with at least one contact element.

FIG. 23 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, first layer 36 can have at least two folds, 110 and 122, incorporated therein. In such an embodiment as illustrated in FIG. 23 in which two folds, 110 and 122, are present, the layer 36 can be bent upon itself such that a first portion of one surface, 56 or 58, of the layer 36 can be in a facing relationship with a second portion of the same surface, 56 or 58, and a first portion of the other surface, 56 or 58, of the layer 36 can be in a facing relationship with a second portion of the same surface, 56 or 58. As a non-limiting example, as illustrated in FIG. 23, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a first portion 124 of the second surface 58 into a facing relationship with a second portion 126 of the second surface 58 of layer 36. The second fold 122 can be created by bending layer 36 at a location along the first length 44 of layer 36 between the transverse edge 48 of layer 36 and the first fold 110 of layer 36. As illustrated in FIG. 23, transverse edge 48 of layer 36 can be in communication with transverse edge 64 of the second layer 38 of the absorbent structure 34. In an embodiment, each fold 110 and 122 can result in layer 36 having multiple layers, such as layers 130, 132, 134 and 136. In an embodiment, layer 36 can have at least one slit 96 extending through the layers, such as layers 130 and 132, of the layer 36. The first layer 36 can have at least two successive slits 96 extending through the layers, 130 and 132, and the two successive slits 96 can create a contact element 88. As illustrated, the at least one slit 96 can extend from the second surface 58 of layer 36, through the first and second portions, 112 and 114, of the first surface 56 of layer 36, and to the second portion 126 of the second surface 58 of layer 36. As illustrated, the slit(s) 96 can be associated with the first fold 110 of the first layer 36. The slit(s) 96 can extend from the fold 110 of the first layer 36 in a direction away from the fold 110 and towards the second fold 122 of first layer 36. The at least one slit 96 can be incorporated into layer 36 prior to or after layer 36 has been folded. As described herein, the fold 110 can be located between the insertion end 18 and the withdrawal end 20 of a resultant tampon 10. Thus, in an embodiment, the contact elements 88 of the absorbent structure 34 illustrated in FIG. 23 can be located between the insertion end 18 and the withdrawal end 20 of a resultant tampon 10. In the non-limiting embodiment illustrated in FIG. 23, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 24:
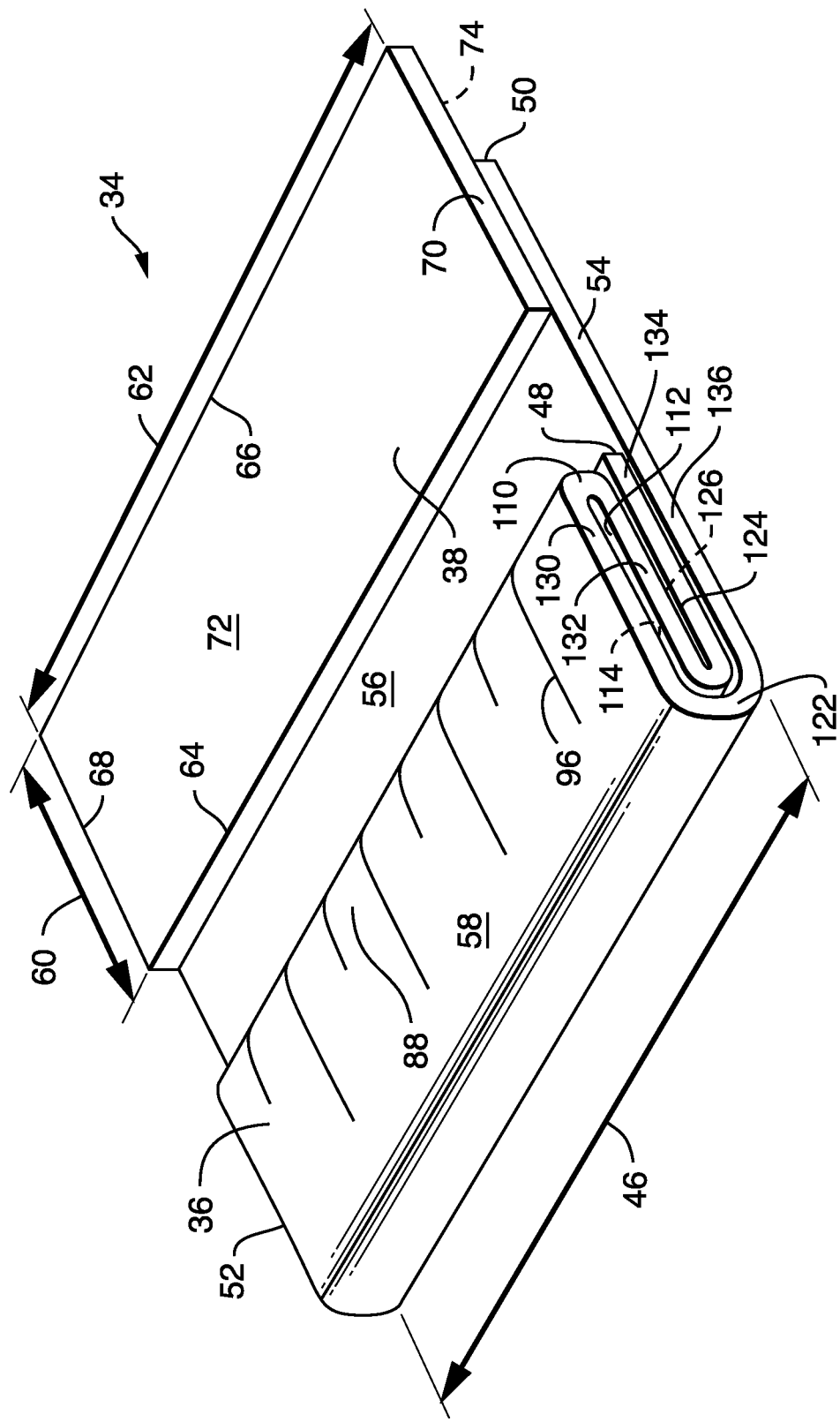
FIG. 24 is a perspective view of an embodiment of an absorbent structure with at least one contact element.

FIG. 24 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, less than 100% of surface 74 of second layer 38 can be in a face to face relationship with surface 56 of first layer 36. As illustrated, first layer 36 can have at least two folds, 110 and 122, incorporated therein. In such an embodiment as illustrated in FIG. 24 in which two folds 110 and 122 are present, the layer 36 can be bent upon itself such that a first portion of one surface, 56 or 58, of the layer 36 can be in a facing relationship with a second portion of the same surface, 56 or 58, and a first portion of the other surface, 56 or 58, of the layer 36 can be in a facing relationship with a second portion of the same surface, 56 or 58. As a non-limiting example, as illustrated in FIG. 24, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a first portion 124 of the second surface 58 into a facing relationship with a second portion 126 of the second surface 58 of layer 36. The second fold 122 can be created by bending layer 36 at a location along the first length 44 of layer 36 between the transverse edge 48 of layer 36 and the first fold 110 of layer 36. As illustrated in FIG. 24, transverse edge 48 of layer 36 does not have to be, but can be, in communication with transverse edge 64 of the second layer 38 of the absorbent structure 34. In an embodiment, each fold 110 and 122 can result in layer 36 having multiple layers, such as layers 130, 132, 134 and 136. In an embodiment, layer 36 can have at least one slit 96 extending through the layers, 130 and 132, of the layer 36. The first layer 36 can have two successive slits 96 extending through the layers, 130 and 132, and the two successive slits 96 can create a contact element 88. As illustrated, the at least one slit 96 can extend from the second surface 58 of layer 36, through the first and second portions, 112 and 114, of the first surface 56 of layer 36, and to the second portion 126 of the second surface 58 of layer 36. As illustrated, the slit(s) 96 can be associated with the first fold 110 of the first layer 36. The slit(s) 96 can extend from the fold 110 of the first layer 36 in a direction away from the fold 110 and towards the second fold 122 of first layer 36. The at least one slit 96 can be incorporated into layer 36 prior to or after layer 36 has been folded. As described herein, the fold 110 can be located between the insertion end 18 and the withdrawal end 20 of a resultant tampon 10. Thus, in an embodiment, the contact elements 88 of the absorbent structure 34 illustrated in FIG. 24 can be located between the insertion end 18 and the withdrawal end 20 of a resultant tampon 10. In the non-limiting embodiment illustrated in FIG. 24, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

As described herein, the nonwoven ribbon 32 of an absorbent structure 34 can be separated into individual units of fleece 30 which can have the same absorbent structure 34 as was present in the nonwoven ribbon 32. The fleece 30 can be formed into a blank 28 which can then be compressed into a pledget 12 of a tampon 10. In various embodiments, the tampon 10 can have a cover 138 and a withdrawal aid 14.

In various embodiments a cover 138 can be provided. As used herein, the term "cover" relates to materials that are in communication with and cover or enclose surfaces of a pledget 12 to prevent the fibrous materials of the absorbent structure 34 from directly contacting the inner walls of a woman's vagina and to reduce the ability of portions (e.g., fibers and the like) from becoming separated from the pledget 12 or the tampon 10 and being left behind upon removal of the tampon 10 from the woman's vagina. In various embodiments, the cover 138 can be a fluid-permeable cover 138. By "fluid-permeable" it is meant that body fluid is able to pass through the cover 138. The cover 138 can be hydrophobic or hydrophilic. By "hydrophilic" it is meant that the cover 138 has an affinity for absorbing or tending to combine with water. By "hydrophobic" it is meant that the cover 138 is antagonistic to or tending not to combine with water. The cover 138 can also be treated with a surfactant or other material to make it hydrophilic or to make it more hydrophilic.

The cover 138 can be bonded with: the nonwoven ribbon 32 prior to separation into individual units of fleece 30, an individual unit of fleece 30, a blank 28 which has been formed from a fleece 30, or to the pledget 12 following compression of the blank 28. In an embodiment in which the cover 138 is bonded with a pledget 12 following compression of a blank 28, the cover 138 can be extensible such that the tampon 10 can expand within the vaginal cavity. In an embodiment in which the absorbent structure 34 is multi-layered, the cover 138 can be bonded with at least one layer of the absorbent structure 34 before, after, or while the layer of the absorbent structure 34 is bonded to another layer of the absorbent structure 34. The absorbent structure 34 can be in a nonwoven ribbon 32 or can be in a fleece 30.

In various embodiments, the cover 138 can be formed from nonwoven materials or apertured films. The nonwoven materials can include, but are not limited to, materials such as natural fibers, synthetic fibers, or blends of natural and synthetic fibers. Natural fibers include, but are not limited to, rayon, cotton, wood pulp, flax, and hemp. Synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. The cover 138 can be made by any number of suitable techniques such as, for example, being spunbonded, carded, hydroentangled, thermally bonded, and resin bonded. In an embodiment, the cover 138 can be formed from an apertured thermoplastic film having either a two-dimensional or a three-dimensional thickness. In an embodiment, the cover 138 can be a 12 gsm smooth calendared material made from bicomponent, polyethylene sheath and polyester core, fibers such as Sawabond 4189 available from Sandler AG, Schwarzenbach, Germany. In an embodiment, the cover 138 can be formed from a single piece of material. In an embodiment, the cover 138 can be formed from multiple discrete pieces of material which are bonded together. In an embodiment, the cover 138 can be bleached. In an embodiment, the cover 138 can have a color.

In an embodiment, the cover 138 can be treated with an aqueous solution to reduce frictional drag, to give the tampon 10 a permanent wettability, to enhance the ease of insertion into and withdrawal from a woman's vagina, and combinations thereof. In an embodiment, the cover 138 can be treated either before being rolled or folded up with the fleece 30 into a blank 28 or after the blank 28 has been formed and the cover 138 has been bonded with the blank 28.

Figure 25:
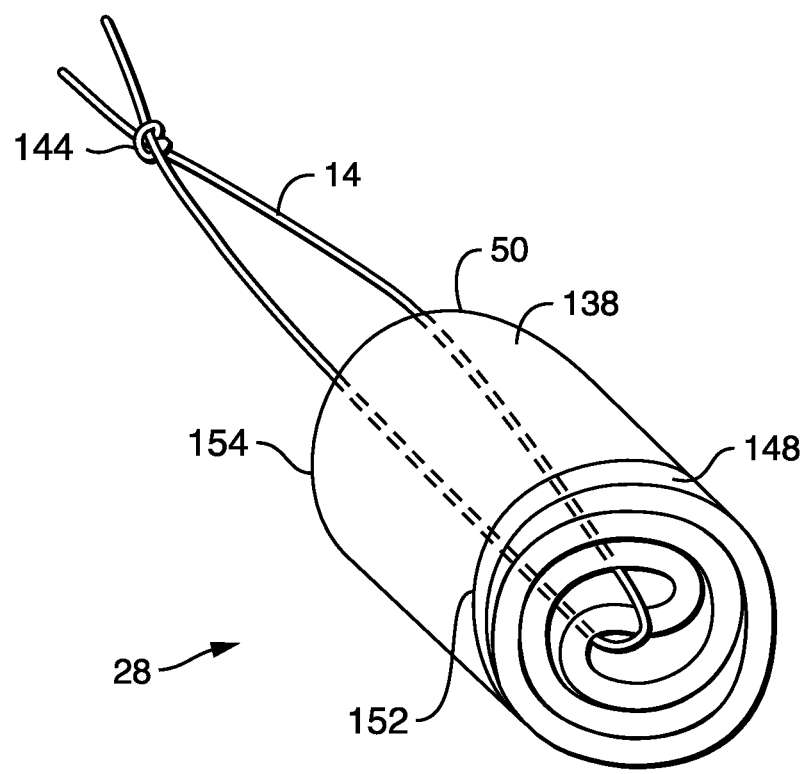
FIG. 25 is a perspective view of an embodiment in which a cover is bonded to a blank.
Figure 26A:
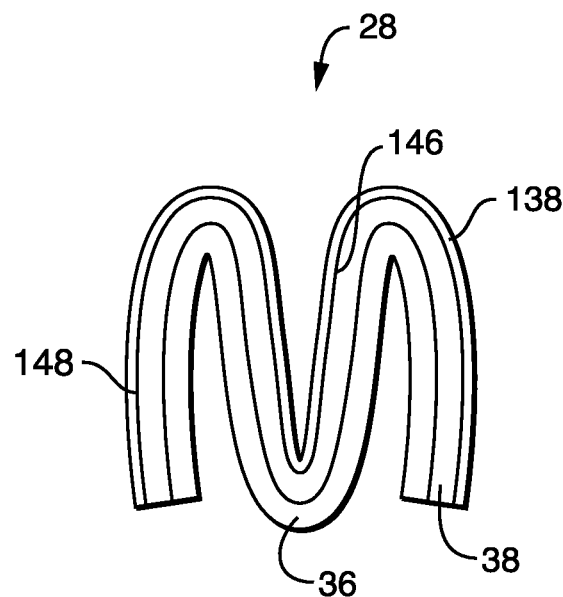
FIG. 26A is an end view of an embodiment in which a cover is bonded to a blank.
Figure 26B:
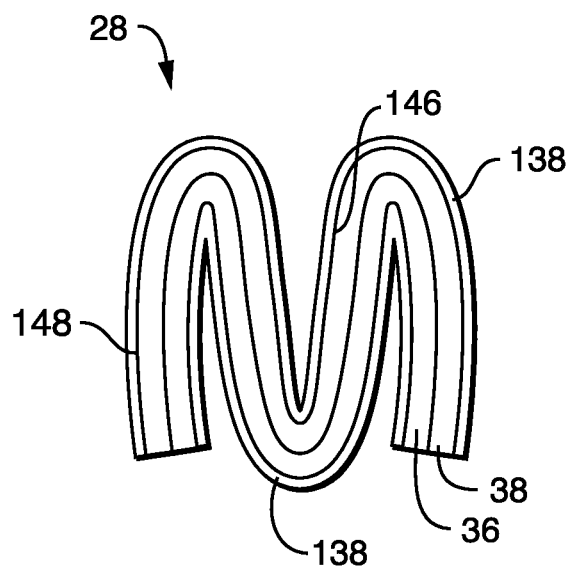
FIG. 26B is an end view of an embodiment in which a cover is bonded to a blank.
Figure 27:
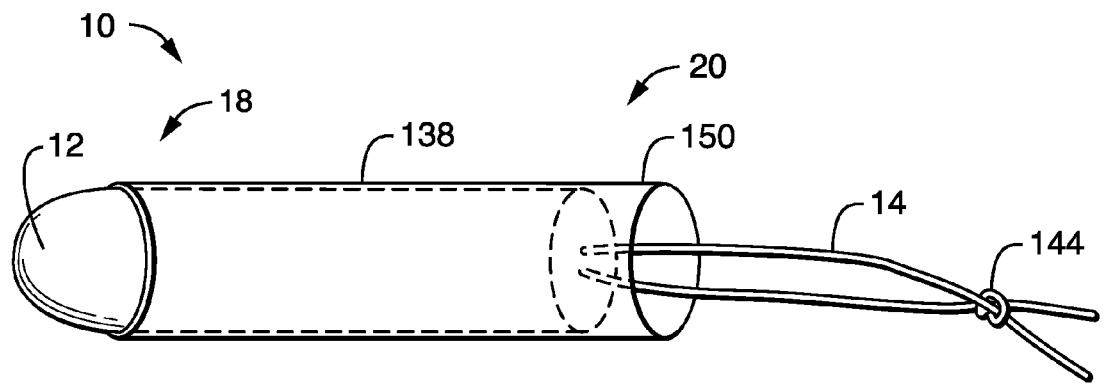
FIG. 27 is a side view of an embodiment of a tampon wherein the cover defines a skirt.

In various embodiments, at least a portion of a cover 138 can cover a body facing surface 148, a portion of an interior surface 146, or combinations thereof of a blank 28. FIG. 25 provides an illustration of a non-limiting embodiment in which at least a portion of a cover 138 can cover a portion of a body facing surface 148 of a blank 28, such as a softwind. As illustrated in FIG. 26A, in an embodiment, at least a portion of a cover 138 can cover a portion of an interior surface 146 of a blank 28 when a fleece 30 is compressed, such as, for example, via side compression. As illustrated in FIG. 26A, in an embodiment, at least a portion of the cover 138 can cover a combination of the body facing surface 148 and the interior surface 146 of a blank 28. The interior surface 146 of the blank 28 can result from folding, rolling, or otherwise manipulating the fleece 30 into the blank 28. It is to be understood that in an embodiment, the interior surface 146 of the pledget 12 may come into contact with the vaginal walls as the tampon 10 can expand when contacted by body fluids. The expansion of the tampon 10 can, therefore, cause exposure of the interior surface 146 of the pledget 12 to the vaginal walls and body fluid. As illustrated in FIG. 26B, in an embodiment two covers 138 can be in communication with a fleece 30 which can be compressed, such as, for example, via side compression, into a blank 28. As illustrated in FIG. 26B, in such an embodiment, at least a portion of each of the covers 138 can cover a portion of an interior surface 146 of a blank 28 of a pledget 12. In such an embodiment, at least a portion of each of the covers 138 can cover a combination of the body facing surface 148 and the interior surface 146 of a blank 28 of a pledget 12. In various embodiments, the cover 138 can extend beyond the withdrawal end 20 of the pledget 12 to form a skirt 150 as illustrated in FIG. 27. It is to be understood that, in an embodiment, the cover 138 can extend beyond the insertion end 18 of a pledget 12.

In an embodiment, the cover 138 can have two edges, 152 and 154. As noted above, the cover 138 can be bonded to a nonwoven ribbon 32, a fleece 30, a blank 28, or a pledget 12. In an embodiment, during the bonding process, at least one of the edges, 152 or 154, of the cover 138 can be substantially aligned with one of the transverse edges, such as transverse edges 48 and 50 or 64 or 66. In an embodiment, during the bonding process, the cover 138 can be bonded to the nonwoven ribbon 32, the fleece 30, the blank 28, or the pledget 12 so as to produce a spiral or helical pattern on the resulting pledget 12. In an embodiment, the two edges, 152 and 154, can be perpendicular to the longitudinal axis 16 of a pledget 12. In an embodiment, the two edges, 152 and 154, can be positioned in a direction parallel to the longitudinal axis 16 of a pledget 12 or at any other angle to the longitudinal axis 16 of a pledget 12 such as may occur if the cover 138 is spirally wound about the pledget 12. Thus, while the cover 138 and the edges, 152 and 154, may be discussed herein in an orientation perpendicular to the longitudinal axis 16 of a pledget 12, one of ordinary skill will be able to recognize how to provide a cover 138 and edges, 152 and 154, in an orientation parallel with the longitudinal axis 16 of a pledget 12 or in an orientation having any other angle in relation to the longitudinal axis 16 of a pledget 12.

In an embodiment, the cover 138 can have uniform properties. In an embodiment, the cover 138 can have non-uniform properties. In such an embodiment, the cover 138 can have regions with differing properties which can be coordinated to increase or decrease absorbency and/or level of expansion of the tampon 10. For example, a region can be more hydrophilic or hydrophobic in comparison to another region of the cover 138. In an embodiment, the hydrophilic region of the cover 138 could substantially cover the portion of the tampon 10 that would contact the menses first to increase menses absorption and as a result increase expansion of that portion of the tampon 10.

The regions of the cover 138 with differing properties may be produced by various methods. One example of a method is by treating the regions of the cover 138 with chemical finishes, such as hydrophilic or hydrophobic finishes that make the regions either more hydrophilic or more hydrophobic, respectively. The regions can also be mechanically altered. Any method known in the art of mechanically altering nonwovens or films can be used. Mechanically altering includes, but is not limited to, processes such as ring-rolling, corrugating, SELFing, and aperturing.

The composition of the cover 138 can also provide for differing properties of the cover 138. Different regions of the cover 138 can be produced from different materials. For example, one region of the cover 138 may have a higher concentration of rayon than another section of the cover 138 to make that region more hydrophilic. Materials could be selected for any property desired for a cover 138 known in the art, such as a selection of a material to provide a region of the cover 138 with greater extensibility. In an embodiment, the cover 138 may include multiple discrete pieces that are bonded together to form a single cover 138. The discrete pieces can have differing properties such as described above. In an embodiment, the discrete pieces of the cover 138 may form the different regions of the cover 138 such as described above. In such an embodiment, one discrete piece may form one region and another discrete piece may form a different region of the cover 138. The discrete pieces can be bonded by any method known to one of ordinary skill in the art, such as sewing, adhesive, thermal bonding, fusion bonding, or combinations thereof.

Figure 28:
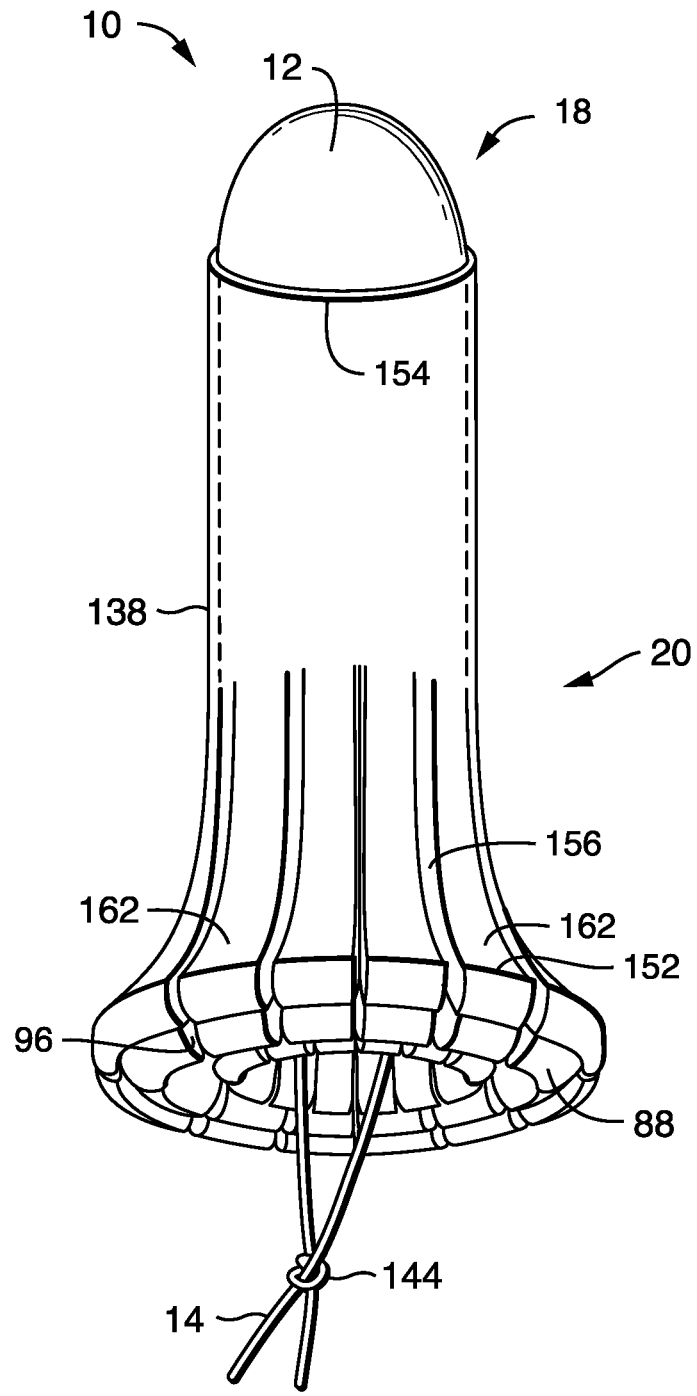
FIG. 28 is a perspective view of an embodiment of a tampon in an activated configuration.

As illustrated in FIG. 28, in an embodiment, the cover 138 can have at least one slit 156. In an embodiment, the slit(s) 156 can be located between the two edges, 152 and 154, of the cover 138. In such an embodiment, the slit 156 can form a cover contact element 162. In an embodiment, the slit(s) 156 can be associated with at least one of the edges, 152 and/or 154. In an embodiment, at least one slit 156 can be associated with at least one of the edges, 152 and/or 154, and at least one slit 156 can be located between the two edges, 152 and 154. In an embodiment in which slits 156 are associated with at least one of the edges, 152 and 154, the cover 138 can have at least two slits 156 which can form a cover contact element 162. The cover contact element 162 can come into contact with the walls of the vagina and can direct fluid flow towards the tampon 10. In an embodiment, the cover 138 can have at least one cover contact element 162. In an embodiment, the cover 138 can have at least 1, 2, 3, 4, 5, 6, 7, 8, 9, or 10 cover contact elements 162. In an embodiment, the cover 138 can have from about 1, 2, 3, 4, 5, 6, 7, 8, 9, or 10 to about 11, 12, 13, 14, 15, 16, 17, 18, 19 or 20 cover contact elements 162. In an embodiment, a cover contact element 162 can be oriented perpendicular to the longitudinal axis 16 of a tampon 10. In an embodiment, a cover contact element 162 can be oriented parallel with the longitudinal axis 16 of a tampon 10. In an embodiment, a cover contact element 162 can be oriented at any angle as desired to the longitudinal axis 16 of a tampon 10.

In an embodiment, a slit 156 of the cover 138 can be substantially aligned with a slit 96 of a layer(s), such as layer(s) 36 and/or 38. In an embodiment, a slit 156 can be offset from a slit 96 of a layer(s), such as layer(s) 36 and/or 38. In an embodiment, a slit 156 of a cover 138 can be substantially aligned with a slit 96 of a layer(s), such as layer(s) 36 and/or 38, and a slit 156 of a cover 138 can be offset from a slit 96 of a layer(s), such as layer(s) 36 and/or 38. In the non-limiting embodiment illustrated in FIG. 28, the slits 156 of the cover 138 can be substantially aligned with the slits 96 of a layer of the absorbent structure 34. In such an embodiment, a slit 156 in the cover 138 can allow the contact element 88 to expand in a direction away from the tampon 10 and to deform and flex away from the tampon 10. In an embodiment, the length of a slit 156 in the cover 138 can be any length deemed suitable. In an embodiment, the length of a slit 156 in the cover 138 can be substantially similar to the length 98 of a slit 96 in a layer(s), such as layer(s) 36 and/or 38. In an embodiment, a width between two successive slits 156 in the cover 138 can be any width as deemed suitable. In an embodiment, the width between two successive slits 156 in the cover 138 can be substantially similar to the width 102 between two successive slits 96 in one of the layers, 36 and/or 38. In an embodiment, the length of a slit 156 and the width between two successive slits 156 in the cover 138 can be substantially similar to or different from the length 98 of a slit 96 and the width 102 between slits 96 in a layer(s), such as layer(s) 36 and/or 38, when the slits 156 in a cover 138 substantially align with the slits 96 in a layer(s), such as layer(s) 36 and/or 38, or when the slits 156 in a cover 138 are offset from the slits 96 in a layer(s), such as layer(s) 36 and/or 38. In an embodiment, a cover contact element 162 can substantially align with a contact element 88 of a layer(s), such as layer(s) 36 and/or 38.

In an embodiment, a cover contact element 162 can be offset from a contact element 88 of a layer(s), such as layer(s) 36 and/or 38.

In various embodiments, the pledget 12 may be subject to further processing to result in a finished tampon. For example, the pledget 12 may be joined with a withdrawal aid 14 and/or applicator.

Figure 29:
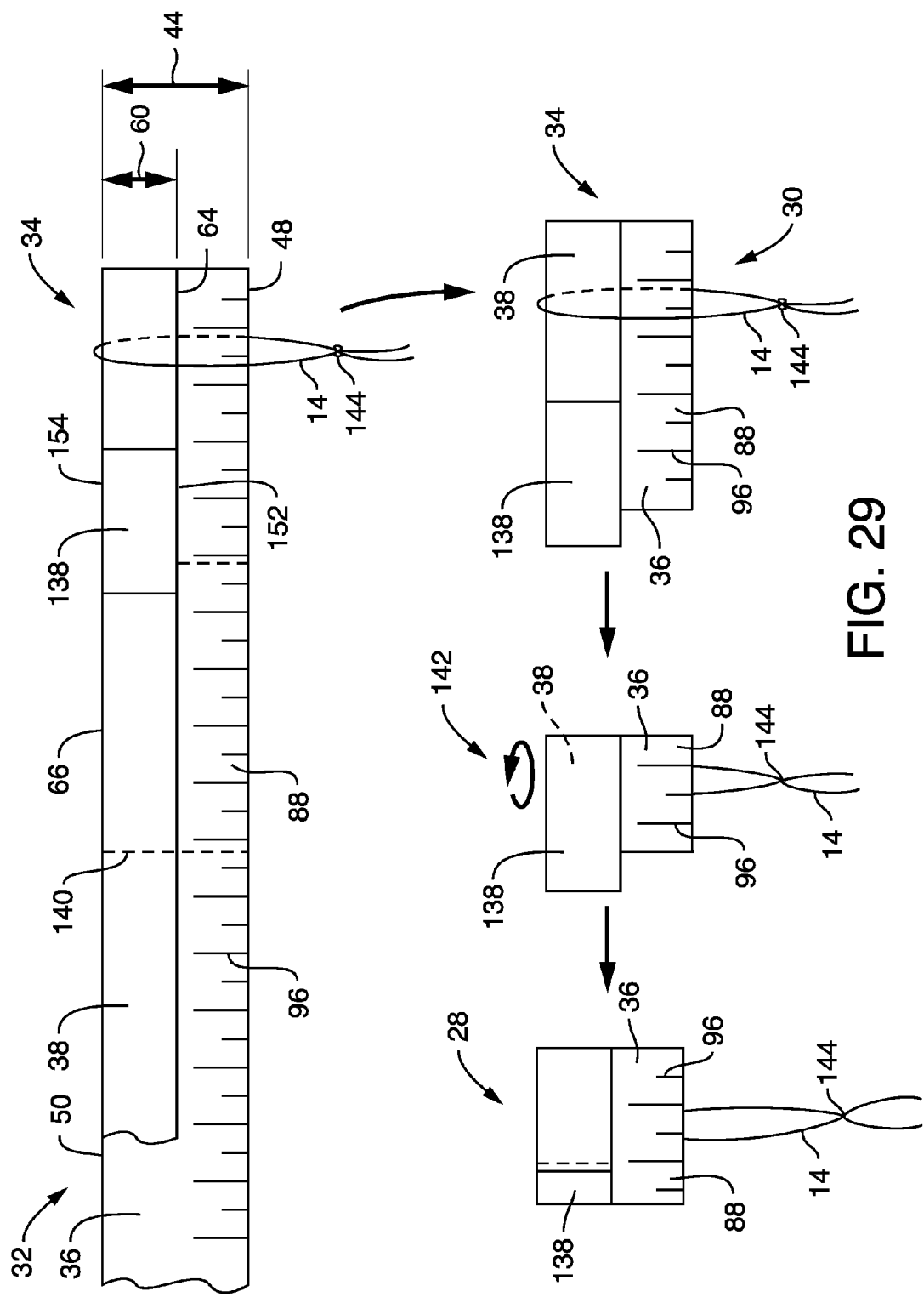
FIG. 29 is a perspective view of an embodiment of a method of manufacturing an absorbent structure.

The withdrawal aid 14 may be attached to the pledget 12 in any suitable manner. For example, an opening can be formed through the pledget 12 (and cover 138 if provided) so as to provide a means for attaching a withdrawal aid 14. In various embodiments, the withdrawal aid 14 can be attached to the fibrous material before or after it is compressed into the pledget 12. The withdrawal aid 14 can be attached to the fibrous material and then looped upon itself. As illustrated in FIG. 29, the withdrawal aid 14 can be associated with the nonwoven ribbon 32 and can further be associated with the fleece 30. In such an embodiment, the withdrawal aid 14 can be, as illustrated, wound with the fleece 30 in the formation of a blank 28. A knot 144 can be formed near the free ends of the withdrawal aid 14 to assure that the withdrawal aid 14 does not separate from the fibrous material. The knot 144 can also serve to prevent fraying of the withdrawal aid 14 and to provide a location where a woman can grasp the withdrawal aid 14 when she is ready to remove the tampon 10 from her vagina.

The withdrawal aid 14 can be constructed from various types of threads or ribbons. A thread or ribbon can be made from 100% cotton fibers and/or other materials in whole or part. The withdrawal aid 14 can be bonded to the absorbent fibers with or without tying. The withdrawal aid 14 can have any suitable length and/or the withdrawal aid 14 can be dyed and/or treated with an anti-wicking agent, such as wax, before being secured to the pledget 12.

FIG. 29 provides a non-limiting illustration of an embodiment of a method of manufacturing a blank 28 of the present disclosure. A nonwoven ribbon 32 which can have an absorbent structure 34, can ultimately result in a blank 28. In an embodiment, the absorbent structure 34 of the nonwoven ribbon 32 can be a single layer. In an embodiment, the absorbent structure of the nonwoven ribbon 32 can be multi-layered. The absorbent structure 34 of the nonwoven ribbon 32, can be manufactured via a multi-bank laydown process, a process whereby pre-formed fibrous material layers are bonded together, or a combination thereof. During the manufacture of the absorbent structure 34 of the nonwoven ribbon 32, the absorbent structure 34 can have any configuration of layers as desired. During the manufacture of a multi-layered absorbent structure 34 of a nonwoven ribbon 32, the layers can be configured into any desired configuration, such as, but not limited to, the configurations described and illustrated herein. The nonwoven ribbon 32 illustrated in FIG. 29 can have an absorbent structure 34 which can have two layers, 36 and 38, which can be placed into communication with each other. In an embodiment, the two layers, 36 and 38, can be bonded to each other after they are placed into communication with each other. Each of the layers, 36 and 38, can have transverse edges, such as transverse edges 48 and 50 of layer 36 and 64 and 66 of layer 38. In the non-limiting illustration of FIG. 29, transverse edge 50 of first layer 36 can be substantially aligned with transverse edge 66 of second layer 38. As illustrated in the non-limiting illustration of FIG. 29, the first layer 36 can have a first length 44 which can be longer than a second length 60 of second layer 38. As noted herein, the two layers, 36 and 38, can be arranged into any desired configuration including, but not limited to, any of the configurations described and illustrated herein. As described herein, at least one slit 96 can be incorporated into at least one of the layers, 36 and/or 38, forming the absorbent structure 34 of the nonwoven ribbon 32. The slit(s) 96 can be incorporated into at least one of the layer(s), such as layer(s) 36 and/or 38, prior to, after, or while placing one of the layers of the absorbent structure 34 into communication with another layer of the absorbent structure 34. In the non-limiting illustration of FIG. 29, the slit(s) 96 can be associated with a transverse edge of one of the layers, 36 and/or 38, such as transverse edge 48 of layer 36. As described herein, in an embodiment, at least one slit 96 can be incorporated into at least one of the layers, 36 and/or 38, in such a configuration so as to not be associated with one of the transverse edges of either of the layers, 36 and/or 38. In the non-limiting embodiment illustrated, a first layer 36 having two transverse edges, 48 and 50, can be provided and a plurality of slits 96 can be associated with transverse edge 48 to form at least one contact element 88. As discussed herein, in an embodiment, a contact element 88 can be associated with any of the transverse edges or can be located between the transverse edges of a layer. As illustrated in the non-limiting embodiment shown in FIG. 29, the contact elements 88 can be associated with transverse edge 48 of layer 36. The nonwoven ribbon 32 can also be provided with a cover 138 and a withdrawal aid 14. As noted above, to create a blank 28, the nonwoven ribbon 32 can be separated into individual units of fleece 30. The separation of the nonwoven ribbon 32 into individual units of fleece 30 can occur by any suitable method such as stretching, perforating, or cutting such as with the use of a die cutter or a knife cutter, and the like. As illustrated in FIG. 29, the nonwoven ribbon 32 can be provided with perforation cuts 140 which can facilitate the separation of the nonwoven ribbon 32 into individual units of fleece 30. The cover 138 can be provided to the nonwoven ribbon 32 before the nonwoven ribbon 32 has been separated into an individual unit of fleece 30 and can be provided in such a way as to span at least a portion of the perforation cuts 140.

As noted above, the nonwoven ribbon 32 can be separated into individual units of fleece 30 which can be rolled, stacked, folded or otherwise manipulated into blanks 28 before the blanks 28 are formed into pledgets 12. For example, suitable menstrual tampons may include "cup" shaped pledgets like those disclosed in U.S. Publication No. 2008/0287902 to Edgett and U.S. Pat. No. 2,330,257 to Bailey; "accordion" or "W-folded" pledgets like those disclosed in U.S. Pat. No. 6,837,882 to Agyapong; "radially wound" pledgets like those disclosed in U.S. Pat. No. 6,310,269 to Friese; "sausage" type or "wad" pledgets like those disclosed in U.S. Pat. No. 2,464,310 to Harwood; "M-folded" tampon pledgets like those disclosed in U.S. Pat. No. 6,039,716 to Jessup; "stacked" tampon pledgets like those disclosed in U.S. 2008/0132868 to Jorgensen; or "bag" type tampon pledgets like those disclosed in U.S. Pat. No. 3,815,601 to Schaefer.

As illustrated in FIG. 29, the fleece 30 can be radially wound into a blank 28, such as a softwind. As illustrated in FIG. 29, the nonwoven ribbon 32 can be separated into individual units of fleece 30, which can undergo a radial winding process, illustrated by the partially wound unit 142, to result in a blank 28. A suitable method for making "radial wound" pledgets is disclosed in U.S. Pat. No. 4,816,100 to Friese. The radial winding method can also include a method for forming the blank into a pledget like that disclosed in U.S. Pat. No. 6,310,269 to Friese. Suitable methods for making "W-folded" pledgets are disclosed in U.S. Pat. No. 6,740,070 to Agyapong; U.S. Pat. No. 7,677,189 to Kondo; and U.S. 2010/0114054 to Mueller. A suitable method for making "cup" pledgets and "stacked" pledgets is disclosed in U.S. 2008/0132868 to Jorgensen.

In various embodiments, the blank 28 can be formed into a pledget 12. In an embodiment, forming the blank 28 into a pledget 12 can include a compressing step which can utilize any suitable means and apparatus. For example, the compressing step may utilize a plurality of dies which reciprocate relative to one another so as to form a mold cavity therebetween. When the blank 28 (e.g., a softwind) is positioned within the mold cavity, the dies may be actuated so as to move towards one another and compress the blank 28. The blank 28 may be compressed any suitable amount. For example, the blank 28 may be compressed at least about 25%, 50%, or 75% of the initial dimensions. For example, a blank 28 can be reduced in diameter to approximately ¼ of the original diameter. The cross-sectional configuration of the resultant pledget 12 may be circular, ovular, rectangular, hexagonal, or any other suitable shape.

In various embodiments, the compressing step may not include any additional heat applied to the pledget 12. In other words, the blank 28 can be compressed into a pledget 12 without external heat being applied to the compression equipment or the blank 28. In various embodiments, the compressing step may incorporate or may be followed by one or more additional stabilization steps. This secondary stabilization can serve to maintain the compressed shape of the pledget 12. In general, the secondary stabilization step can create hydrogen bonds between the absorbent fibers and/or may further strengthen the entanglement of the absorbent fibers to maintain the shape of the compressed pledget 12.

Figure 30:
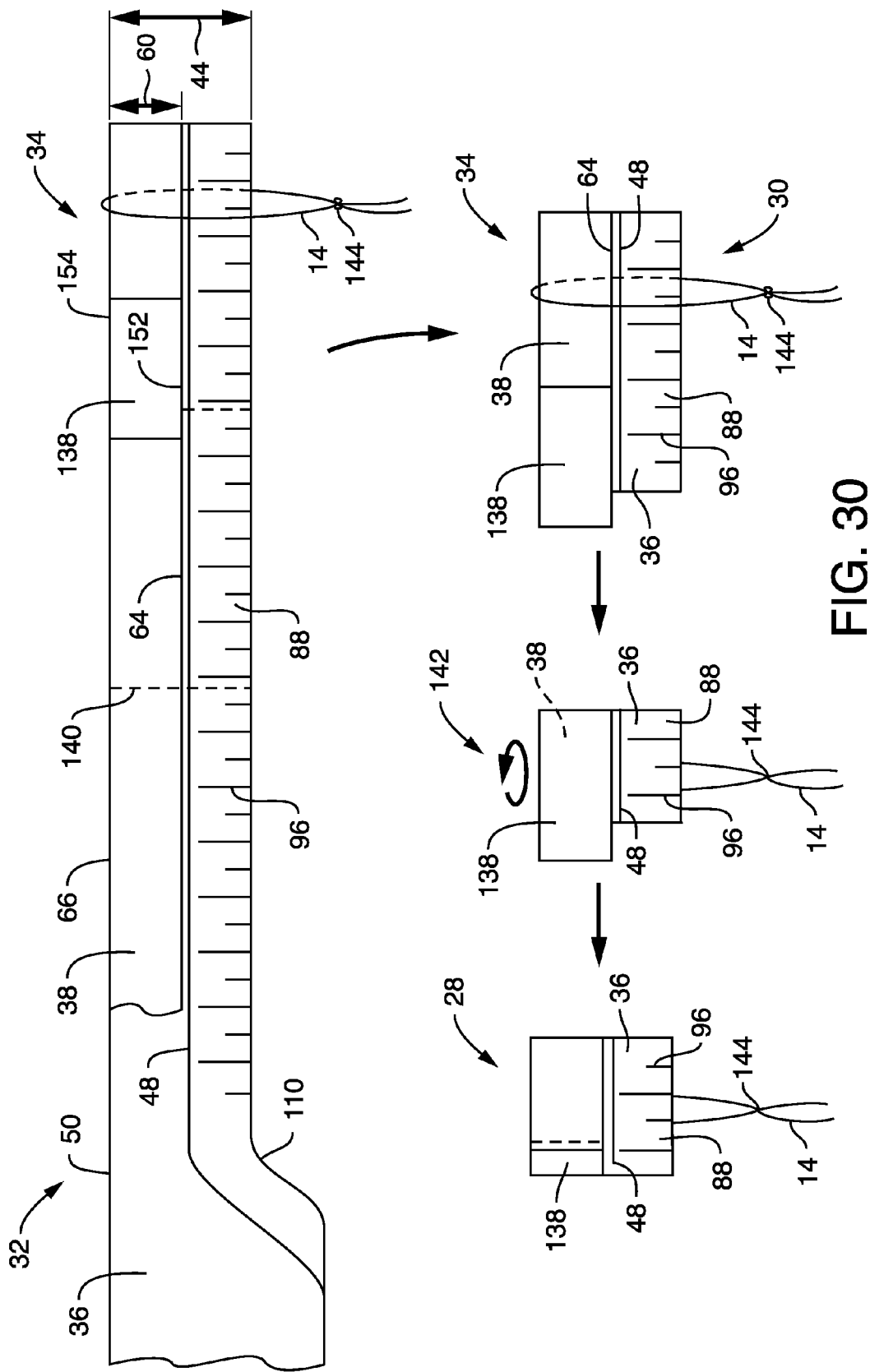
FIG. 30 is a perspective view of an embodiment of a method of manufacturing an absorbent structure.

FIG. 30 provides a non-limiting illustration of an embodiment of a method of manufacturing a nonwoven ribbon 32 of the present disclosure. A nonwoven ribbon 32 which can have an absorbent structure 34, can ultimately result in a blank 28. In an embodiment, the absorbent structure 34 of the nonwoven ribbon 32 can be a single layer. In an embodiment, the absorbent structure of the nonwoven ribbon 32 can be multi-layered. As described herein, the absorbent structure 34 of the nonwoven ribbon 32, can be manufactured via a multi-bank laydown process, a process whereby pre-formed fibrous material layers are bonded together, or a combination thereof. During the manufacture of the absorbent structure 34 of the nonwoven ribbon 32, the absorbent structure 34 can have any configuration of layers as desired. During the manufacture of a multi-layered absorbent structure 34 of a nonwoven ribbon 32, the layers can be configured into any desired configuration, such as, but not limited to, the configurations described and illustrated herein. The nonwoven ribbon 32 illustrated in FIG. 30 can have an absorbent structure 34 which can have two layers, 36 and 38, which can be placed into communication with each other. In an embodiment, the two layers, 36 and 38, can be bonded to each other after having been placed into communication with each other. Each of the layers, 36 and 38, can have transverse edges, such as transverse edges 48 and 50 of layer 36 and 64 and 66 of layer 38. In the non-limiting illustration of FIG. 30, transverse edge 50 of first layer 36 can be substantially aligned with transverse edge 66 of second layer 38. As illustrated in the non-limiting illustration of FIG. 30, the first layer 36 can have a first length 44 which can be longer than a second length 60 of second layer 38. As noted herein, the two layers, 36 and 38, can be arranged into any desired configuration including, but not limited to, any of the configurations described and illustrated herein. In the non-limiting embodiment illustrated, a fold 110 can be incorporated into first layer 36. The fold 110 can bring transverse edge 48 of layer 36 into communication with transverse edge 64 of layer 38. As discussed herein, additional folds can be incorporated into the absorbent structure 34 as desired and into any configuration as desired. As described herein, at least one slit 96 can be incorporated into at least one of the layers, 36 and/or 38, forming the absorbent structure 34 of the nonwoven ribbon 32. The slit(s) 96 can be incorporated into at least one of the layer(s), such as layers 36 and/or 38, prior to, after, or while placing one of the layers of the absorbent structure 34 into communication with another layer of the absorbent structure 34. In the non-limiting illustration of FIG. 30, the slit(s) 96 can be associated with the fold 110 of first layer 36. As illustrated in FIG. 30, a plurality of slits 96 can be associated with the fold 110 of first layer 36 to form at least one contact element 88. As discussed herein, in an embodiment, a contact element 88 can be associated with any of the transverse edges, a fold, or can be located between the transverse edges of a layer. As described herein, in an embodiment, at least one slit 96 can be incorporated into at least one of the layers, 36 and/or 38, in such a configuration so as to not be associated with one of the transverse edges of either of the layers, 36 and/or 38. The nonwoven ribbon 32 can also be provided with a cover 138 and a withdrawal aid 14. As noted above, to create a blank 28, the nonwoven ribbon 32 can be separated into individual units of fleece 30. The separation of the nonwoven ribbon 32 into individual units of fleece 30 can occur by any suitable method such as stretching, perforating, or cutting such as with the use of a die cutter or a knife cutter, and the like. As illustrated in FIG. 30, the nonwoven ribbon 32 can be provided with perforation cuts 140 which can facilitate the separation of the nonwoven ribbon 32 into individual units of fleece 30. The cover 138 can be provided to the nonwoven ribbon 32 before the nonwoven ribbon 32 has been separated into an individual unit of fleece 30 and can be provided in such a way as to span at least a portion of the perforation cuts 140.

As illustrated in FIG. 30, the fleece 30 can be radially wound into a blank 28, such as a softwind. As illustrated in FIG. 30, the nonwoven ribbon 32 can be separated into individual units of fleece 30, which can undergo a radial winding process, illustrated by the partially wound unit 142, to result in a blank 28. As described herein, in various embodiments, the blank 28 can be formed into a pledget 12.

In various embodiments, the pledget 12 may be subject to further processing to result in a finished tampon. For example, the pledget 12 may be joined with a withdrawal aid 14, such as described herein, and/or applicator.

The withdrawal aid 14 may be attached to the pledget 12 in any suitable manner. For example, an opening can be formed through the pledget 12 (and cover 138 if provided) so as to provide a means for attaching a withdrawal aid 14. In various embodiments, the withdrawal aid 14 can be attached to the fibrous material before or after it is compressed into the pledget 12. The withdrawal aid 14 can be attached to the fibrous material and then looped upon itself. As illustrated in FIGS. 29 and 30, the withdrawal aid 14 can be associated with the nonwoven ribbon 32 and can further be associated with the fleece 30. In such an embodiment, the withdrawal aid 14 can be, as illustrated, wound with the fleece 30 in the formation of a blank 28. A knot 144 can then be formed near the free ends of the withdrawal aid 14 to assure that the withdrawal aid 14 does not separate from the fibrous material. The knot 144 can also serve to prevent fraying of the withdrawal aid 14 and to provide a place or point where a woman can grasp the withdrawal aid 14 when she is ready to remove the tampon 10 from her vagina.

In various embodiments, the tampon 10 may also include one or more additional features. For example, the tampon 10 may include a "protection" feature as exemplified by U.S. Pat. No. 6,840,927 to Hasse, U.S. 2004/0019317 to Takagi, U.S. Pat. No. 2,123,750 to Schulz, and the like. In some embodiments, the tampon 10 may include an "anatomical" shape as exemplified by U.S. Pat. No. 5,370,633 to Villalta, an "expansion" feature as exemplified by U.S. Pat. No. 7,387,622 to Pauley, an "acquisition" feature as exemplified by U.S. 2005/0256484 to Chase, an "insertion" feature as exemplified by U.S. Pat. No. 2,112,021 to Harris, a "placement" feature as exemplified by U.S. Pat. No. 3,037,506 to Penska, or a "removal" feature as exemplified by U.S. Pat. No. 6,142,984 to Brown.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pledget comprising:
    a. an absorbent structure comprising:
        i. a first layer comprising a first surface, a second surface, a first contact element at least partially bounded by a base and at least partially bounded by a free edge, and a second contact element at least partially bounded by a base and at least partially bounded by a free edge, wherein the second contact element is at least partially separated from the first contact element by a slit;
        ii. a second layer comprising a first surface and a second surface;
    wherein at least one of the first surface and the second surface of the first layer is in a face to face relationship with at least one of the first surface and the second surface of the second layer;
    wherein the first layer further comprises a first transverse edge to be located at an insertion end of the pledget and a second transverse edge to be located at a withdrawal end of the pledge and the second layer further comprises a first transverse edge to be located at the insertion end of the pledget and a second transverse edge to be located at the withdrawal end of the pledget;
    wherein each of the contact elements of the first layer is associated with the first transverse edge of the first layer to be located at the insertion end of the pledget and the slit is associated with and extends in a longitudinal direction from the first transverse edge of the first layer; and wherein the pledget further comprises a cover comprising at least two slits which form at least one cover contact element which is coextensive with at least one of the contact elements of the first layer.

2. The pledget of claim 1 wherein the first layer further comprises a fold.

3. The pledget of claim 2 wherein the first layer further comprises a first portion of at least one of the first surface and the second surface of the first layer in communication with a second portion of at least one of the first surface and the second surface of the first layer.

4. The pledget of claim 1 wherein at least one of the transverse edges of the first layer aligns with at least one of the transverse edges of the second layer.

5. The pledget of claim 1 wherein at least one of the transverse edges of the first layer extends beyond at least one of the transverse edges of the second layer.

6. A pledget comprising an absorbent structure comprising a first layer radially wound with a second layer and a first contact element, which is at least partially bounded by a base and at least partially bounded by a free edge, incorporated in the first layer at least partially separated from a second contact element, which is at least partially bounded by a base and at least partially bounded by a free edge, incorporated in the first layer, wherein the first contact element and the second contact element are at least partially separated by a slit, wherein the first layer further comprises a first transverse edge to be located at an insertion end of the pledget and a second transverse edge to be located at a withdrawal end of the pledget and the second layer further comprises a first transverse edge to be located at the insertion end of the pledget and a second transverse edge to be located at the withdrawal end of the pledget; wherein each of the contact elements of the first layer is associated with the first transverse edge of the first layer to be located at the insertion end of the pledget and the slit is associated with and extends in a longitudinal direction from the first transverse edge of the first layer; and wherein the pledget further comprises a cover comprising at least two slits which form at least one cover contact element which is coextensive with at least one of the contact elements of the first layer.

7. The pledget of claim 6 wherein the first layer further comprises a fold.

8. The pledget of claim 6 wherein at least one of the transverse edges of the first layer aligns with at least one of the transverse edges of the second layer.

9. The pledget of claim 6 wherein at least one of the transverse edges of the first layer extends beyond at least one of the transverse edges of the second layer.

10. A pledget comprising:
 a. an absorbent structure comprising:
  i. a first layer comprising a first surface, a second surface, a first contact element at least partially bounded by a base and at least partially bounded by a free edge, and a second contact element at least partially bounded by a base and at least partially bounded by a free edge, wherein the second contact element is at least partially separated from the first contact element by a slit;
  ii. a second layer comprising a first surface and a second surface;
 wherein at least one of the first surface and the second surface of the first layer is in a face to face relationship with at least one of the first surface and the second surface of the second layer;

wherein the first layer further comprises a first transverse edge to be located at an insertion end of the pledget and a second transverse edge to be located at a withdrawal end of the pledge and the second layer further comprises a first transverse edge to be located at an insertion end of the pledget and a second transverse edge to be located at a withdrawal end of the pledget;

wherein each of the contact elements of the first layer is associated with the second transverse edge of the first layer to be located at the withdrawal end of the pledget and the slit is associated with and extends in a longitudinal direction from the second transverse edge of the first layer; and wherein the pledget further comprises a cover comprising at least two slits which form at least one cover contact element which is coextensive with at least one of the contact elements of the first layer.

11. The pledget of claim 10 wherein the first layer further comprises a fold.

12. The pledget of claim 11 wherein the first layer further comprises a first portion of at least one of the first surface and the second surface of the first layer in communication with a second portion of at least one of the first surface and the second surface of the first layer.

13. The pledget of claim 10 wherein at least one of the transverse edges of the first layer aligns with at least one of the transverse edges of the second layer.

14. The pledget of claim 10 wherein at least one of the transverse edges of the first layer extends beyond at least one of the transverse edges of the second layer.

15. A pledget comprising an absorbent structure comprising a first layer radially wound with a second layer and a first contact element, which is at least partially bounded by a base and at least partially hounded by a free edge, incorporated in the first layer at least partially separated from a second contact element, which is at least partially bounded by a base and at least partially bounded by a free edge, incorporated in the first layer, wherein the first contact element and the second contact element are at least partially separated by a slit, wherein the first layer further comprises a first transverse edge to be located at an insertion end of the pledget and a second transverse edge to be located at a withdrawal end of the pledget and the second layer further comprises a first transverse edge to be located at the insertion end of the pledget and a second transverse edge to be located at the withdrawal end of the pledget; wherein each of the contact elements of the first layer is associated with the second transverse edge of the first layer to be located at the withdrawal end of the pledget and the slit is associated with and extends in a longitudinal direction from the second transverse edge of the first layer; and wherein the pledget further comprises a cover comprising at least two slits which form at least one cover contact element which is coextensive with at least one of the contact elements of the first layer.

16. The pledget of claim 15 wherein the first layer further comprises a fold.

17. The pledget of claim 15 wherein at least one of the transverse edges of the first layer aligns with at least one of the transverse edges of the second layer.

18. The pledget of claim 15 wherein at least one of the transverse edges of the first layer extends beyond at least one of the transverse edges of the second layer.

* * * * *